US010822615B2

(12) United States Patent
Wood et al.

(10) Patent No.: US 10,822,615 B2
(45) Date of Patent: Nov. 3, 2020

(54) SIMULTANEOUS GENE SILENCING AND SUPPRESSING GENE SILENCING IN THE SAME CELL

(71) Applicant: Commonwealth Scientific and Industrial Research Organisation, Acton, Australian Capital Territory (AU)

(72) Inventors: Craig Christopher Wood, Dickson (AU); Fatima Naim, Oxley (AU); Surinder Pal Singh, Downer (AU); Peter Michael Waterhouse, Paddington (AU)

(73) Assignee: Commonwealth Scientific and Industrial Research Organisation, Acton (AU)

( * ) Notice: Subject to any disclaimer, the term of this patent is extended or adjusted under 35 U.S.C. 154(b) by 633 days.

(21) Appl. No.: 14/369,579

(22) PCT Filed: Dec. 21, 2012

(86) PCT No.: PCT/AU2012/001594
§ 371 (c)(1),
(2) Date: Jun. 27, 2014

(87) PCT Pub. No.: WO2013/096992
PCT Pub. Date: Jul. 4, 2013

(65) Prior Publication Data
US 2014/0380528 A1 Dec. 25, 2014

Related U.S. Application Data

(60) Provisional application No. 61/580,574, filed on Dec. 27, 2011.

(51) Int. Cl.
*C12N 15/82* (2006.01)
*C12N 15/113* (2010.01)
*C12N 15/11* (2006.01)

(52) U.S. Cl.
CPC ........ *C12N 15/8245* (2013.01); *C12N 15/111* (2013.01); *C12N 15/113* (2013.01); *C12N 15/8216* (2013.01); *C12N 15/8218* (2013.01); *C12N 15/8247* (2013.01); *C12N 2310/14* (2013.01); *C12N 2320/50* (2013.01); *C12N 2750/12022* (2013.01); *C12N 2770/38022* (2013.01)

(58) Field of Classification Search
None
See application file for complete search history.

(56) References Cited

U.S. PATENT DOCUMENTS 7,217,854 B1 * 5/2007 Baulcombe .......... C12N 9/1205
800/278
2005/0059044 A1 * 3/2005 Graham ................ C12N 15/111
435/6.11

FOREIGN PATENT DOCUMENTS

| EP | 0465572 | 1/1992 |
|---|---|---|
| WO | WO 1997/20936 | 6/1997 |
| WO | WO 1999/32619 | 7/1999 |
| WO | WO 1999/49029 | 9/1999 |
| WO | WO 1999/53050 | 10/1999 |
| WO | WO 2001/34815 | 5/2001 |
| WO | WO 2004/009779 A2 | 1/2004 |
| WO | WO 2008/087562 A8 | 10/2008 |
| WO | WO 2010/057246 A1 | 5/2010 |
| WO | WO 2011/001434 A1 | 1/2011 |
| WO | WO 2011/100982 A2 | 8/2011 |

OTHER PUBLICATIONS

Lakatos et al (EMBO Journal, 2006, 25: 2768-2780).*
Glick et al (PNAS, 2008, 105(1):157-161).*
Muangsan et al (The Plant Journal, 2004, 38(6):1004-1014).*
Waterhouse et al (Nature Reviews, 2003, 4: 29-38).*
Fukunaga et al (EMBO Journal, 2009, 28:545-555).*
Geneseq AYB86753 (see alignment appended to the Office action; published online Jul. 2010).*
Qu et al (FEBS Letters, 2005, 579: 5958-5964).*
Fukunaga et al (EMBO, 2009, 28: 545-555; cited on IDS).*
Pre et al (Plant Physiology, 2008, 147: 1347-1357).*
Meister et al (Nature, 2004, 421: 343-349).*
Zrachya et al (Virology, 2007, 358, 159-165).*
Krysan et al (Plant Cell, 1999, 11: 2283-2290).*
Ilardi et al (GM Crops, 2011, 2:1, 24-33).*
Kumakura et al (FEBS Letters, 2009, 583: 1261-1266).*
Joon-Woo Ahn et al.: "Host-dependent suppression of RNA silencing mediated by the viral suppressor p19 in potato", Planta ; An International Journal of Plant Biology, Springer, Berlin, DE, vol. 234, No. 5, Jun. 30, 2011, pp. 1065-1072. p. 1070, right-hand column; p. 1071, right-hand column; figures 2 and 3.
E. Varallyay et al.: "Plant Virus-Mediated Induction of miR168 is associated with repression of ARGONAUTE1 accumulation", The EMBO Journal, vol. 29, Sep. 7, 2010, pp. 3507-3519.
Craig C. Wood et al.: "A leaf-based assay using interchangeable design principles to rapidly assemble multistep recombinant pathways", Plant Biotechnology Journal, vol. 7 No. 9, Oct. 13, 2009, pp. 914-924.
Lombardi, Raffaele et al.: "High-level HIV-1 Nef transient expression in Nicotiana benthamiana using the P19 gene silencing suppressor protein of Artichoke Mottled Crinckle Virus", BMC Biotechnology, Biomed Central LTD., London, GB, vol. 9 No. 1, Nov. 20, 2009, p. 96.

(Continued)

Primary Examiner — Stephen Uyeno
(74) Attorney, Agent, or Firm — Gary J. Gershik; John P. White; Cooper & Dunham LLP

(57) ABSTRACT

The present invention relates to genetically modified cells that are capable of optimal transgene expression by co-expressing a silencing suppressor whilst at the same time are also capable of silencing a gene, such as a naturally occurring gene of the cell. The present invention also relates to methods of producing the modified cells, as well as relates to processes for obtaining a genetically modified cell with a desired property.

Figure 1:
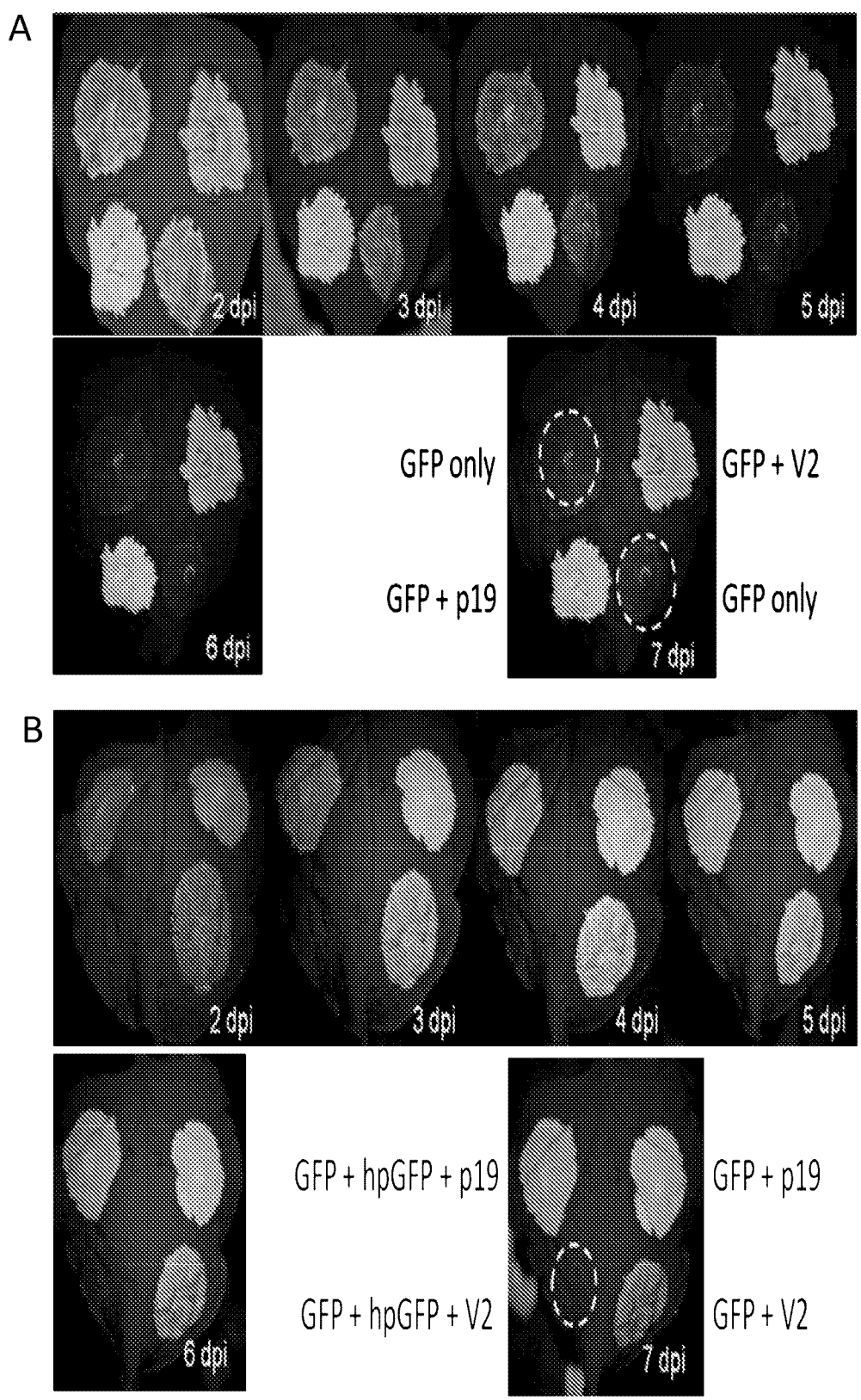

20 Claims, 12 Drawing Sheets
Specification includes a Sequence Listing.

(56) References Cited

OTHER PUBLICATIONS

Mallory A. C. et al.: "A viral suppressor of 1-18 RNA scilencing differentially regulated the accumulation of short interfering RNAs and micro-RNAs in tobacco", Proceedings of the National Academy of Sciences, National Academy of Sciences, US. vol. 99, No. 23, Nov. 12, 2002, pp. 15228-15233.
Fatima Naim et al.: "Advancing Engineering of Lipid Metabolism in Nicotiana benthamiana Using a Draft Genome and the V2 Viral Silencing-Suppressor Protein",Plos One, vol. 7, No. 12, Dec. 26, 2012, p. e52717.
Bassam Berry et al.: "Viral Suppressors of RNA Silencing Hinder Exogenous and Endogenous Small RNA Pathways in *Drosophila*", Plos One, vol. 4, No. 6, Jun. 10, 2009, p. e5866.
Supplementary European Search Report and Search Opinion, dated Jul. 31, 2015 in connection with European Patent Application No. 12863467.2, national stage of PCT International Application No. PCT/AU2012/001594, filed Dec. 21, 2012.
Berry, B. et al. (2009). Viral suppressors of RNA silencing hinder exogenous and endogenous small RNA pathways in *Drosophila*. *PLoS One*, 4(6), 1-10.
Takeda, A. et al. (2002). Identification of a novel RNA silencing suppressor, NSs protein of tomato spotted wilt virus. *FEBS Letters*, 532, 75-79.
Merai, Z. et al. (2005). Aureusvirus P14 is an efficient RNA silencing suppressor that binds double-stranded RNAs without size specificity. *Journal of Virology*, 79(11), 7217-7226.
Johansen, L. K. and Carrington, J. C. (2001). Silencing on the spot. Induction and suppression of RNA silencing in the agrobacterium-mediated transient expression system. *Plant Physiology*, 126(3), 930-938.
Chiu, M. H. et al. (2010). The silencing suppressor P25 of Potato virus X interacts with Argonaute1 and mediates its degradation through the proteasome pathway. *Molecular Plant Pathology*, 11(5), 641-649.
Notification of Transmittal of the International Search Report and the Written Opinion of the International Searching Authority, or the Declaration, including an International Search Report and Written Opinion of the International Searching Authority, dated Feb. 26, 2013 in connection with PCT International Application No. PCT/AU2012/001594, filed Dec. 21, 2012.
First Examination Report dated Aug. 10, 2016 corresponding to European Patent Application No. 12863467.2.
Notification Concerning Transmittal of International Preliminary Report on Patentability (Chapter I of the Patent Cooperation Treaty), including an International Preliminary Report on Patentability and Written Opinion of the International Searching Authority, dated Jul. 10, 2014 by The International Bureau of WIPO in connection with PCT International Application No. PCT/AU2012/001594, filed Dec. 21, 2012.
Feb. 20, 2017 Response to Examination Report filed in connection with counterpart European Patent Application No. 12863467.2.
Kasschau, K.D. et al., P1/HC-Pro, a viral suppressor of RNA silencing, interferes with *Arabidopsis* development and miRNA function, Developmental Cell, 4(2), 205-217.
First Examination Report issued for AU2012324003 dated Aug. 19, 2014.
Bakker et al. (2006) Proc. Natl. Acad. Sci. USA 103:7577-7582.
Beclin et al. (2002) Current Biology 12:684-688.
Elmayan et al. (1998) Plant Cell 10: 1747-1757.
Fukunaga and Doudna (2009) EMBO Journal 28:545-555.
Koziel et al. (1996) Plant Mol. Biol. 32:393-405.
Levy et al. (2008) Proc. Natl. Acad. Sci. USA 105:10131-10136.
Mourrain et al. (2000) Cell 101:533-542.
Petrie et al. (2010) Plant Methods 6:8.
Schwab et al. (2006) Plant Cell 18: 1121-1133.
Smith et al. (2000) Nature 407:319-320.
Taylor (1997) The Plant Cell 9:1245-1249.
Voinnet et al. (2003) Plant Journal 33:949-956.
Waterhouse et al (1998) Proc. Natl. Acad. Sci. USA 95:13959-13964.
Ye et al. (2003) Nature 426:874-878.
Examination Report dated Jun. 6, 2017 which issued in relation to corresponding European patent application 12863467.2.
Mar. 16, 2018 Response to Jun. 6, 2017 Communication pursuant to Article 94(3) EPC and Jan. 15, 2018 Communication pursuant to Rule 112(1) EPC filed in connection with European Patent Application No. EP 12863467.2.
Examination report dated Apr. 6, 2018 in connection with European Patent Application No. EP 12863467.2.
Nov. 9, 2018 First Examination Report dated which issued in connection with corresponding Canadian patent application 2,860,432.
May 8, 2020 Request for Reinstatement and Response to the Nov. 9, 2018 Examination Report filed in connection with corresponding Canadian Patent Application 2,860,432.

* cited by examiner

SEQUENCE LISTING

<160> NUMBER OF SEQ ID NOS: 53

<210> SEQ ID NO 1

```
<211> LENGTH: 116
<212> TYPE: PRT
<213> ORGANISM: tomato leaf yellow curl virus

<400> SEQUENCE: 1

Met Trp Asp Pro Leu Leu Asn Glu Phe Pro Glu Ser Val His Gly Phe
1               5                   10                  15

Arg Cys Met Leu Ala Ile Lys Tyr Leu Gln Ser Val Glu Glu Thr Tyr
            20                  25                  30

Glu Pro Asn Thr Leu Gly His Asp Leu Ile Arg Asp Leu Ile Ser Val
        35                  40                  45

Val Arg Ala Arg Asp Tyr Val Glu Ala Thr Arg Arg Tyr Asn His Phe
50                  55                  60

His Ala Arg Leu Glu Gly Ser Pro Lys Ala Glu Leu Arg Gln Pro Ile
65                  70                  75                  80

Gln Gln Pro Cys Cys Cys Pro His Cys Pro Arg His Lys Gln Ala Thr
                85                  90                  95

Ile Met Asp Val Gln Ala His Val Pro Glu Ala Gln Asn Ile Gln Asn
            100                 105                 110

Val Ser Lys Pro
        115

<210> SEQ ID NO 2
<211> LENGTH: 172
<212> TYPE: PRT
<213> ORGANISM: tomato bushy stunt virus

<400> SEQUENCE: 2

Met Glu Arg Ala Ile Gln Gly Asn Asp Ala Arg Glu Gln Ala Asn Ser
1               5                   10                  15

Glu Arg Trp Asp Gly Gly Ser Gly Gly Thr Thr Ser Pro Phe Lys Leu
            20                  25                  30

Pro Asp Glu Ser Pro Ser Trp Thr Glu Trp Arg Leu His Asn Asp Glu
        35                  40                  45

Thr Asn Ser Asn Gln Asp Asn Pro Leu Gly Phe Lys Glu Ser Trp Gly
50                  55                  60

Phe Gly Lys Val Val Phe Lys Arg Tyr Leu Arg Tyr Asp Arg Thr Glu
65                  70                  75                  80

Ala Ser Leu His Arg Val Leu Gly Ser Trp Thr Gly Asp Ser Val Asn
                85                  90                  95

Tyr Ala Ala Ser Arg Phe Phe Gly Phe Asp Gln Ile Gly Cys Thr Tyr
            100                 105                 110

Ser Ile Arg Phe Arg Gly Val Ser Ile Thr Val Ser Gly Gly Ser Arg
        115                 120                 125

Thr Leu Gln His Leu Cys Glu Met Ala Ile Arg Ser Lys Gln Glu Leu
130                 135                 140

Leu Gln Leu Ala Pro Ile Glu Val Glu Ser Asn Val Ser Arg Gly Cys
145                 150                 155                 160

Pro Glu Gly Thr Glu Thr Phe Glu Lys Glu Ser Glu
                165                 170

<210> SEQ ID NO 3
<211> LENGTH: 351
<212> TYPE: DNA
<213> ORGANISM: tomato leaf yellow curl virus

<400> SEQUENCE: 3
```

```
atgtgggatc cacttctaaa tgaatttcct gaatctgttc acggatttcg ttgtatgtta      60
gctattaaat atttgcagtc cgttgaggaa acttacgagc ccaatacatt gggccacgat     120
ttaattaggg atcttatatc tgttgtaagg gcccgtgact atgtcgaagc gaccaggcga     180
tataatcatt ccacgcccg cctcgaaggt tcgccgaagg ctgaacttcg acagcccata      240
cagcagccgt gctgctgtcc ccattgtcca aggcacaaac aagcgacgat catgacgta      300
caggcccatg taccggaagc ccagaatata cagaatgtat cgaagccctg a              351

<210> SEQ ID NO 4
<211> LENGTH: 519
<212> TYPE: DNA
<213> ORGANISM: tomato bushy stunt virus

<400> SEQUENCE: 4
atggaacgag ctatacaagg aaacgacgct agggaacaag ctaacagtga acgttgggat      60
ggaggatcag gaggtaccac ttctcccttc aaacttcctg acgaaagtcc gagttggact     120
gagtggcggc tacataacga tgagacgaat tcgaatcaag ataatcccct tggtttcaag     180
gaaagctggg gtttcgggaa agttgtattt aagagatatc tcagatacga caggacggaa     240
gcttcactgc acagagtcct ggatcttgg acgggagatt cggttaacta tgcagcatct      300
cgattttttcg gtttcgacca gatcggatgt acctatagta ttcggtttcg aggagttagt     360
atcaccgttt ctggagggtc gcgaactctt cagcatctct gtgagatggc aattcggtct     420
aagcaagaac tgctacagct tgccccaatc gaagtggaaa gtaatgtatc aagaggatgc     480
cctgaaggta ctgagacctt cgaaaaagaa agcgagtaa                            519

<210> SEQ ID NO 5
<211> LENGTH: 145
<212> TYPE: PRT
<213> ORGANISM: Sesamum indicum

<400> SEQUENCE: 5

Met Ala Glu His Tyr Gly Gln Gln Gln Gln Thr Arg Ala Pro His Leu
1               5                   10                  15

Gln Leu Gln Pro Arg Ala Gln Arg Val Val Lys Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Gln
            100                 105                 110

Leu Glu Ser Ala Lys Thr Lys Leu Ala Ser Lys Ala Arg Glu Met Lys
        115                 120                 125

Asp Arg Ala Glu Gln Phe Ser Gln Gln Pro Val Ala Gly Ser Gln Thr
    130                 135                 140

Ser
145

<210> SEQ ID NO 6
<211> LENGTH: 438
```

<212> TYPE: DNA
<213> ORGANISM: Sesamum indicum

<400> SEQUENCE: 6

```
atggctgagc attatggtca acaacagcag accagggcgc ctcacctgca gctgcagccg        60
cgcgcccagc gggtagtgaa ggcggccacc gccgtgacag ccggcggctc gcttctcgtc       120
ctctctggcc tcactttagc cggaactgtt attgcgctca ccatcgccac tccgctgctt       180
gtgatcttta gccccgttct ggtgccggcg gtcataacca tttttcttgct gggtgcgggt       240
tttctggcat ccggaggctt cggcgtggcg gcgctgagtg tgctgtcgtg gatttacaga       300
tatctgacag gaaacaccc gccggggcg gatcagctgg aatcggcaaa gacgaagctg         360
gcgagcaagg cgcgagagat gaaggatagg gcagagcagt tctcgcagca gcctgttgcg       420
gggtctcaaa cttcttga                                                     438
```

<210> SEQ ID NO 7
<211> LENGTH: 506
<212> TYPE: PRT
<213> ORGANISM: Arabidopsis thaliana

<400> SEQUENCE: 7

```
Met Thr Ser Val Asn Val Lys Leu Leu Tyr Arg Tyr Val Leu Thr Asn
  1               5                  10                  15

Phe Phe Asn Leu Cys Leu Phe Pro Leu Thr Ala Phe Leu Ala Gly Lys
             20                  25                  30

Ala Ser Arg Leu Thr Ile Asn Asp Leu His Asn Phe Leu Ser Tyr Leu
         35                  40                  45

Gln His Asn Leu Ile Thr Val Thr Leu Leu Phe Ala Phe Thr Val Phe
     50                  55                  60

Gly Leu Val Leu Tyr Ile Val Thr Arg Pro Asn Pro Val Tyr Leu Val
 65                  70                  75                  80

Asp Tyr Ser Cys Tyr Leu Pro Pro His Leu Lys Val Ser Val Ser
                 85                  90                  95

Lys Val Met Asp Ile Phe Tyr Gln Ile Arg Lys Ala Asp Thr Ser Ser
            100                 105                 110

Arg Asn Val Ala Cys Asp Asp Pro Ser Ser Leu Asp Phe Leu Arg Lys
        115                 120                 125

Ile Gln Glu Arg Ser Gly Leu Gly Asp Glu Thr Tyr Ser Pro Glu Gly
    130                 135                 140

Leu Ile His Val Pro Pro Arg Lys Thr Phe Ala Ala Ser Arg Glu Glu
145                 150                 155                 160

Thr Glu Lys Val Ile Ile Gly Ala Leu Glu Asn Leu Phe Glu Asn Thr
                165                 170                 175

Lys Val Asn Pro Arg Glu Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205

Leu Arg Ser Asn Ile Lys Ser Phe Asn Leu Gly Gly Met Gly Cys Ser
    210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Gln Gly
                245                 250                 255

Ile Tyr Ala Gly Glu Asn Arg Ser Met Met Val Ser Asn Cys Leu Phe
            260                 265                 270
```

```
Arg Val Gly Gly Ala Ala Ile Leu Leu Ser Asn Lys Ser Gly Asp Arg
            275                 280                 285

Arg Arg Ser Lys Tyr Lys Leu Val His Thr Val Arg Thr His Thr Gly
        290                 295                 300

Ala Asp Asp Lys Ser Phe Arg Cys Val Gln Gln Glu Asp Asp Glu Ser
305                 310                 315                 320

Gly Lys Ile Gly Val Cys Leu Ser Lys Asp Ile Thr Asn Val Ala Gly
                325                 330                 335

Thr Thr Leu Thr Lys Asn Ile Ala Thr Leu Gly Pro Leu Ile Leu Pro
            340                 345                 350

Leu Ser Glu Lys Phe Leu Phe Phe Ala Thr Phe Val Ala Lys Lys Leu
        355                 360                 365

Leu Lys Asp Lys Ile Lys His Tyr Tyr Val Pro Asp Phe Lys Leu Ala
370                 375                 380

Val Asp His Phe Cys Ile His Ala Gly Gly Arg Ala Val Ile Asp Glu
385                 390                 395                 400

Leu Glu Lys Asn Leu Gly Leu Ser Pro Ile Asp Val Glu Ala Ser Arg
                405                 410                 415

Ser Thr Leu His Arg Phe Gly Asn Thr Ser Ser Ser Ile Trp Tyr
            420                 425                 430

Glu Leu Ala Tyr Ile Glu Ala Lys Gly Arg Met Lys Lys Gly Asn Lys
        435                 440                 445

Ala Trp Gln Ile Ala Leu Gly Ser Gly Phe Lys Cys Asn Ser Ala Val
            450                 455                 460

Trp Val Ala Leu Arg Asn Val Lys Ala Ser Ala Asn Ser Pro Trp Gln
465                 470                 475                 480

His Cys Ile Asp Arg Tyr Pro Val Lys Ile Asp Ser Asp Leu Ser Lys
                485                 490                 495

Ser Lys Thr His Val Gln Asn Gly Arg Ser
            500                 505

<210> SEQ ID NO 8
<211> LENGTH: 1842
<212> TYPE: DNA
<213> ORGANISM: Arabidopsis thaliana

<400> SEQUENCE: 8
gaattcggta ccccgggttc gaaatcgata agcttggatc tcgatcccgc gaaattaata    60
cgactcacta tagggagacc acaacggttt ccctctgggt aaatttctag ttttctcct   120 tcatttctt ggttaggacc cttttctctt tttatttttt tgagctttga tctttcttta   180
aactgatcta ttttttaatt gattggttat ggtgtaaata ttacatagct ttaactgata   240
atctgattac tttatttcgt gtgtctatga tgatgatgat agttacagaa ccggcggccg   300
ccgaattcga taaacagagc aatgacgtcc gttaacgtta agctccttta ccgttacgtc   360
ttaaccaact ttttcaacct ctgtttgttc ccgttaacgg cgttcctcgc cggaaaagcc   420
tctcggctta ccataaacga tctccacaac ttcctttcct atctccaaca aaccttata   480 acagtaactt tactctttgc tttcactgtt ttcggtttgg ttctctacat cgtaacccga   540
cccaatccgg tttatctcgt tgactactcg tgttaccttc caccaccgca tctcaaagtt   600
agtgtctcta agtcatgga tatttttctac caaataagaa aagctgatac ttcttcacgg   660
aacgtggcat gtgatgatcc gtcctcgctc gatttcctga ggaagattca agagcgttca   720
ggtctaggtg atgagacgta cagtcctgag ggactcattc acgtaccacc gcggaagact   780
```

```
tttgcagcgt cacgtgaaga gacagagaag gttatcatcg gtgcgctcga aaatctattc    840
gagaacacca aagttaaccc tagagagatt ggtatacttg tggtgaactc aagcatgttt    900
aatccaactc cttcgctatc cgctatggtc gttaatactt tcaagctccg aagcaacatc    960
aaaagcttta atctaggagg aatgggttgt agtgctggtg ttattgccat tgatttggct   1020
aaagacttgt tgcatgttca taaaaacact tatgctcttg tggtgagcac tgagaacatc   1080
acacaaggca tttatgctgg agaaaataga tcaatgatgg ttagcaattg cttgtttcgt   1140
gttggtgggg ccgcgatttt gctctctaac aagtcgggag accggagacg tccaagtac    1200 aagctagttc acacggtccg aacgcatact ggagctgatg acaagtcttt tcgatgtgtg   1260
caacaagaag acgatgagag cggcaaaatc ggagtttgtc tgtcaaagga cataaccaat   1320
gttgcgggga caacttac gaaaaatata gcaacattgg gtccgttgat tcttcctttta    1380 agcgaaaagt ttcttttttt cgctaccttc gtcgccaaga aacttctaaa ggataaaatc   1440
aagcattact atgttccgga tttcaagctt gctgttgacc atttctgtat tcatgccgga   1500
ggcagagccg tgatcgatga gctagagaag aacttaggac tatcgccgat cgatgtggag   1560
gcatctagat caacgttaca tagatttggg aatacttcat ctagctcaat ttggtatgaa   1620
ttagcataca tagaggcaaa gggaagaatg aagaaaggga ataaagcttg gcagattgct   1680
ttaggatcag ggtttaagtg taatagtgcg gtttgggtgg ctctacgcaa tgtcaaggca   1740
tcggcaaata gtccttggca acattgcatc gatagatatc cggttaaaat tgattctgat   1800
ttgtcaaagt caaagactca tgtccaaaac ggtcggtcct aa                      1842
```

<210> SEQ ID NO 9
<211> LENGTH: 520
<212> TYPE: PRT
<213> ORGANISM: Arabidopsis thaliana

<400> SEQUENCE: 9

```
Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Gly Arg Gly Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125

Lys Gln Ser His Ala Gly Leu Phe Asn Leu Cys Val Val Val Leu Ile
    130                 135                 140

Ala Val Asn Ser Arg Leu Ile Ile Glu Asn Leu Met Lys Tyr Gly Trp
145                 150                 155                 160

Leu Ile Arg Thr Asp Phe Trp Phe Ser Ser Arg Ser Leu Arg Asp Trp
                165                 170                 175

Pro Leu Phe Met Cys Cys Ile Ser Leu Ser Ile Phe Pro Leu Ala Ala
```

```
                180                 185                 190
Phe Thr Val Glu Lys Leu Val Leu Gln Lys Tyr Ile Ser Glu Pro Val
            195                 200                 205

Val Ile Phe Leu His Ile Ile Ile Thr Met Thr Glu Val Leu Tyr Pro
        210                 215                 220

Val Tyr Val Thr Leu Arg Cys Asp Ser Ala Phe Leu Ser Gly Val Thr
225                 230                 235                 240

Leu Met Leu Leu Thr Cys Ile Val Trp Leu Lys Leu Val Ser Tyr Ala
                245                 250                 255

His Thr Ser Tyr Asp Ile Arg Ser Leu Ala Asn Ala Ala Asp Lys Ala
            260                 265                 270

Asn Pro Glu Val Ser Tyr Tyr Val Ser Leu Lys Ser Leu Ala Tyr Phe
        275                 280                 285

Met Val Ala Pro Thr Leu Cys Tyr Gln Pro Ser Tyr Pro Arg Ser Ala
290                 295                 300

Cys Ile Arg Lys Gly Trp Val Ala Arg Gln Phe Ala Lys Leu Val Ile
305                 310                 315                 320

Phe Thr Gly Phe Met Gly Phe Ile Ile Glu Gln Tyr Ile Asn Pro Ile
                325                 330                 335

Val Arg Asn Ser Lys His Pro Leu Lys Gly Asp Leu Leu Tyr Ala Ile
            340                 345                 350

Glu Arg Val Leu Lys Leu Ser Val Pro Asn Leu Tyr Val Trp Leu Cys
        355                 360                 365

Met Phe Tyr Cys Phe Phe His Leu Trp Leu Asn Ile Leu Ala Glu Leu
370                 375                 380

Leu Cys Phe Gly Asp Arg Glu Phe Tyr Lys Asp Trp Trp Asn Ala Lys
385                 390                 395                 400

Ser Val Gly Asp Tyr Trp Arg Met Trp Asn Met Pro Val His Lys Trp
                405                 410                 415

Met Val Arg His Ile Tyr Phe Pro Cys Leu Arg Ser Lys Ile Pro Lys
            420                 425                 430

Thr Leu Ala Ile Ile Ile Ala Phe Leu Val Ser Ala Val Phe His Glu
        435                 440                 445

Leu Cys Ile Ala Val Pro Cys Arg Leu Phe Lys Leu Trp Ala Phe Leu
450                 455                 460

Gly Ile Met Phe Gln Val Pro Leu Val Phe Ile Thr Asn Tyr Leu Gln
465                 470                 475                 480

Glu Arg Phe Gly Ser Thr Val Gly Asn Met Ile Phe Trp Phe Ile Phe
                485                 490                 495

Cys Ile Phe Gly Gln Pro Met Cys Val Leu Leu Tyr Tyr His Asp Leu
            500                 505                 510

Met Asn Arg Lys Gly Ser Met Ser
        515                 520

<210> SEQ ID NO 10
<211> LENGTH: 1563
<212> TYPE: DNA
<213> ORGANISM: Arabidopsis thaliana

<400> SEQUENCE: 10
atggcgattt tggattctgc tggcgttact acggtgacgg agaacggtgg cggagagttc       60
gtcgatcttg ataggcttcg tcgacggaaa tcgagatcgg attcttctaa cggacttctt      120
ctctctggtt ccgataataa ttctccttcg gatgatgttg agctcccgc cgacgttagg       180
```

```
gatcggattg attccgttgt taacgatgac gctcagggaa cagccaattt ggccggagat    240
aataacggtg gtggcgataa taacggtggt ggaagaggcg gcggagaagg aagaggaaac    300
gccgatgcta cgtttacgta tcgaccgtcg gttccagctc atcggagggc gagagagagt    360
ccacttagct ccgacgcaat cttcaaacag agccatgccg gattattcaa cctctgtgta    420
gtagttctta ttgctgtaaa cagtagactc atcatcgaaa atcttatgaa gtatggttgg    480
ttgatcagaa cggatttctg gtttagttca agatcgctgc gagattggcc gcttttcatg    540
tgttgtatat ccctttcgat cttccttttg gctgccttta cggttgagaa attggtactt    600
cagaaataca tatcagaacc tgttgtcatc tttcttcata ttattatcac catgacagag    660
gttttgtatc cagtttacgt caccctaagg tgtgattctg cttttttatc aggtgtcact    720
ttgatgctcc tcacttgcat tgtgtggcta aagttggttt cttatgctca tactagctat    780
gacataagat ccctagccaa tgcagctgat aaggccaatc ctgaagtctc ctactacgtt    840
agcttgaaga gcttggcata tttcatggtc gctcccacat tgtgttatca gccaagttat    900
ccacgttctg catgtatacg aagggttgg gtggctcgtc aatttgcaaa actggtcata    960
ttcaccggat tcatgggatt tataatagaa caatatataa atcctattgt caggaactca    1020
aagcatcctt tgaaaggcga tcttctatat gctattgaaa gagtgttgaa gctttcagtt    1080
ccaaatttat atgtgtggct ctgcatgttc tactgcttct ccacctttg gttaaacata    1140 ttggcagagc ttctctgctt cggggatcgt gaattctaca aagattggtg gaatgcaaaa    1200
agtgtgggag attactggag aatgtggaat atgcctgttc ataaatggat ggttcgacat    1260
atatacttcc cgtgcttgcg cagcaagata ccaaagacac tcgccattat cattgctttc    1320
ctagtctctg cagtctttca tgagctatgc atcgcagttc cttgtcgtct cttcaagcta    1380
tgggcttttc ttgggattat gtttcaggtg cctttggtct tcatcacaaa ctatctacag    1440
gaaaggtttg gctcaacggt ggggaacatg atcttctggt tcatcttctg cattttcgga    1500
caaccgatgt gtgtgcttct ttattaccac gacctgatga accgaaaagg atcgatgtca    1560
tga                                                                 1563
```

<210> SEQ ID NO 11
<211> LENGTH: 383
<212> TYPE: PRT
<213> ORGANISM: Arabidopsis thaliana

<400> SEQUENCE: 11

```
Met Gly Ala Gly Gly Asn Met Ser Leu Val Thr Ser Lys Thr Gly Glu
1               5                   10                  15

Lys Lys Asn Pro Leu Glu Lys Val Pro Thr Ser Lys Pro Pro Phe Thr
            20                  25                  30

Val Gly Asp Ile Lys Lys Ala Ile Pro Pro His Cys Phe Gln Arg Ser
        35                  40                  45

Leu Val Arg Ser Phe Ser Tyr Val Val Tyr Asp Leu Leu Val Ser
    50                  55                  60

Val Phe Tyr Tyr Ile Ala Thr Thr Tyr Phe His Leu Leu Pro Ser Pro
65                  70                  75                  80

Tyr Cys Tyr Leu Ala Trp Pro Ile Tyr Trp Ile Cys Gln Gly Cys Val
                85                  90                  95

Cys Thr Gly Ile Trp Val Ile Ala His Glu Cys Gly His His Ala Phe
            100                 105                 110

Ser Asp Tyr Gln Trp Val Asp Asp Thr Val Gly Leu Ile Leu His Ser
        115                 120                 125
```

Ala Leu Met Val Pro Tyr Phe Ser Trp Lys Tyr Ser His Arg Arg His
        130                 135                 140

His Ser Asn Thr Gly Ser Leu Glu Arg Asp Glu Val Phe Val Pro Lys
145                 150                 155                 160

Pro Lys Ser Gln Leu Gly Trp Tyr Ser Lys Tyr Leu Asn Asn Pro Pro
                165                 170                 175

Gly Arg Val Ile Ser Leu Thr Ile Thr Leu Thr Leu Gly Trp Pro Leu
            180                 185                 190

Tyr Leu Ala Phe Asn Val Ser Gly Arg His Tyr Asp Arg Phe Ala Cys
        195                 200                 205

His Tyr Asp Pro Tyr Gly Pro Ile Tyr Asn Asp Arg Glu Arg Leu Gln
    210                 215                 220

Ile Phe Leu Ser Asp Ala Gly Val Ile Gly Ala Gly Tyr Leu Leu Tyr
225                 230                 235                 240

Arg Ile Ala Leu Val Lys Gly Leu Ala Trp Leu Val Cys Met Tyr Gly
                245                 250                 255

Val Pro Leu Leu Ile Val Asn Gly Phe Leu Val Leu Ile Thr Tyr Leu
            260                 265                 270

Gln His Thr His Pro Ser Leu Pro His Tyr Asp Ser Ser Glu Trp Asp
        275                 280                 285

Trp Leu Arg Gly Ala Leu Ala Thr Val Asp Arg Asp Tyr Gly Ile Leu
    290                 295                 300

Asn Lys Val Phe His Asn Ile Thr Asp Thr His Val Val His His Leu
305                 310                 315                 320

Phe Ser Thr Met Pro His Tyr Asn Ala Met Glu Ala Thr Lys Ala Val
                325                 330                 335

Lys Pro Leu Leu Gly Asp Tyr Tyr Gln Phe Asp Gly Thr Pro Val Phe
            340                 345                 350

Lys Ala Met Trp Arg Glu Ala Lys Glu Cys Ile Tyr Val Glu Lys Asp
        355                 360                 365

Glu Ala Ser Gln Gly Lys Gly Val Phe Trp Tyr Lys Asn Lys Phe
    370                 375                 380

<210> SEQ ID NO 12
<211> LENGTH: 661
<212> TYPE: DNA
<213> ORGANISM: Artificial Sequence
<220> FEATURE:
<223> OTHER INFORMATION: dsRNA hairpin targetting N. benthamiana FAD2

<400> SEQUENCE: 12
tagaacagat ggtgcacgac gtgagtatcg gtgatgttgt ggaagacctt gtttagaatg      60
ccatagtctc tgtcgacggt tgccaaagct cccttagcc aatcccattc ggatgaatcg      120
tagtgaggca atgacgggtg agtgtgctgc aaataagtga tcaagacgag gaagccgttc      180
acgattagga gtggtacgcc atacatacac acgagccaag ctagcccttt taccaaggca      240
atacgatata gtagataacc agctccaata actccagcat cagaaaggaa gatctgtagc      300
ctctcgcggt cattgtagat tgggccgtaa gggtcatagt gacatgcaaa gcgatcataa      360
tgtcggccag aaacattgaa agccaagtac aaaggccagc caagagtaag ggtgatcgta      420
agtgaaataa cccggcctgg tggattgttc aagtacttgg aataccatcc gagttgtgat      480
ttcggcttag gcacaaaaac ctcatcgcgc tcgagtgagc cagtgttgga gtggtggcga      540
cgatgactat atttccaaga gaagtagggc accatcagag cagagtggag gataagcccg      600

```
acagtgtcat caacccactg gtagtcacta aaggcatggt ggccacattc gtgcgcaata    660
a                                                                   661
```

```
<210> SEQ ID NO 13
<211> LENGTH: 26
<212> TYPE: DNA
<213> ORGANISM: Artificial Sequence
<220> FEATURE:
<223> OTHER INFORMATION: forward primer

<400> SEQUENCE: 13
tcattgcgca cgaatgtggc caccat                                         26

<210> SEQ ID NO 14
<211> LENGTH: 22
<212> TYPE: DNA
<213> ORGANISM: Artificial Sequence
<220> FEATURE:
<223> OTHER INFORMATION: reverse primer

<400> SEQUENCE: 14
cgagaacaga tggtgcacga cg                                             22

<210> SEQ ID NO 15
<211> LENGTH: 32
<212> TYPE: DNA
<213> ORGANISM: Artificial Sequence
<220> FEATURE:
<223> OTHER INFORMATION: forward primer

<400> SEQUENCE: 15
aacgcgttcg acgaattaat tccaatccca ca                                  32

<210> SEQ ID NO 16
<211> LENGTH: 26
<212> TYPE: DNA
<213> ORGANISM: Artificial Sequence
<220> FEATURE:
<223> OTHER INFORMATION: reverse primer

<400> SEQUENCE: 16
acgcgtctgc tgagcctcga catgtt                                         26

<210> SEQ ID NO 17
<211> LENGTH: 25
<212> TYPE: DNA
<213> ORGANISM: Artificial Sequence
<220> FEATURE:
<223> OTHER INFORMATION: forward primer

<400> SEQUENCE: 17
tttatgggag ctggtggtaa tatgt                                          25

<210> SEQ ID NO 18
<211> LENGTH: 28
<212> TYPE: DNA
<213> ORGANISM: Artificial Sequence
<220> FEATURE:
<223> OTHER INFORMATION: reverse primer

<400> SEQUENCE: 18
ccctcagaat ttgtttttgt accagaaa                                       28

<210> SEQ ID NO 19
<211> LENGTH: 30
```

```
<212> TYPE: DNA
<213> ORGANISM: Artificial Sequence
<220> FEATURE:
<223> OTHER INFORMATION: forward primer

<400> SEQUENCE: 19
ttactagtat ggatgctgca catggtatct                                    30

<210> SEQ ID NO 20
<211> LENGTH: 36
<212> TYPE: DNA
<213> ORGANISM: Artificial Sequence
<220> FEATURE:
<223> OTHER INFORMATION: reverse primer

<400> SEQUENCE: 20
ttactagttc aatcatccat gaaggaatat gcagaa                             36

<210> SEQ ID NO 21
<211> LENGTH: 468
<212> TYPE: PRT
<213> ORGANISM: Gossypium hirsutum

<400> SEQUENCE: 21
```

Met Asp Ala Ala His Gly Ile Leu Gly Lys His Ser Val Pro Pro
1               5                   10                  15

Ser Pro Lys Asn Met Ser Pro Ser Leu Pro Lys Asn Met Ser Pro Ser
            20                  25                  30

Phe Met Glu Thr Thr Ala Arg Leu Phe Val Thr Lys Phe Phe Gln Gln
        35                  40                  45

Tyr Ile Ser Met Gly Cys Val Ile Phe Leu Glu Gly Gly Arg Ile
    50                  55                  60

Phe Thr Phe Lys Gly Asn Met Glu Lys Cys Pro Leu Lys Thr Val Leu
65                  70                  75                  80

Lys Val His Asn Pro Gln Phe Tyr Trp Arg Ile Met Lys Glu Ala Asp
                85                  90                  95

Ile Gly Leu Ala Asp Ala Tyr Ile His Gly Asp Phe Ser Phe Leu Asp
            100                 105                 110

Glu Asn Glu Gly Leu Leu Asn Leu Phe Arg Ile Leu Val Ala Asn Lys
        115                 120                 125

Glu Asn Ser Ala Ala Ser Gly Ser Thr Lys Arg Arg Thr Trp Trp Ser
    130                 135                 140

Pro Ala Leu Leu Thr Ala Ser Ile Ser Ser Ala Lys Tyr Phe Val Lys
145                 150                 155                 160

His Leu Leu Arg Gln Asn Thr Ile Thr Gln Ala Arg Arg Asn Ile Ser
                165                 170                 175

Arg His Tyr Asp Leu Ser Asn Glu Leu Phe Ser Leu Tyr Leu Gly Lys
            180                 185                 190

Met Met Gln Tyr Ser Ser Gly Val Phe Arg Thr Gly Glu Glu His Leu
        195                 200                 205

Asp Val Ala Gln Arg Arg Lys Ile Ser Ser Leu Ile Glu Lys Thr Arg
    210                 215                 220

Ile Glu Lys Trp His Glu Val Leu Asp Ile Gly Cys Gly Trp Gly Ser
225                 230                 235                 240

Leu Ala Ile Glu Thr Val Lys Arg Thr Gly Cys Lys Tyr Thr Gly Ile
                245                 250                 255

Thr Leu Ser Glu Gln Gln Leu Lys Tyr Ala Gln Glu Lys Val Lys Glu
            260                 265                 270

```
Ala Gly Leu Glu Asp Asn Ile Lys Ile Leu Leu Cys Asp Tyr Arg Gln
            275                 280                 285

Leu Pro Lys Glu His Gln Phe Asp Arg Ile Ile Ser Val Glu Met Val
        290                 295                 300

Glu His Val Gly Glu Glu Tyr Ile Glu Phe Tyr Arg Cys Cys Asp
305                 310                 315                 320

Gln Leu Leu Lys Glu Asp Gly Leu Phe Val Leu Gln Phe Ile Ser Ile
                325                 330                 335

Pro Glu Glu Leu Ser Lys Glu Ile Gln Gln Thr Ala Gly Phe Leu Lys
                340                 345                 350

Glu Tyr Ile Phe Pro Gly Gly Thr Leu Leu Ser Leu Asp Arg Asn Leu
            355                 360                 365

Ser Ala Met Ala Ala Thr Arg Phe Ser Val Glu His Val Glu Asn
370                 375                 380

Ile Gly Met Ser Tyr Tyr His Thr Leu Arg Trp Trp Arg Lys Leu Phe
385                 390                 395                 400

Leu Lys Asn Thr Ser Lys Val Leu Ala Leu Gly Phe Asp Glu Lys Phe
                405                 410                 415

Met Arg Thr Trp Glu Tyr Tyr Phe Asp Tyr Cys Ala Ala Gly Phe Lys
            420                 425                 430

Thr Gly Thr Leu Ile Asp Tyr Gln Val Val Phe Ser Arg Ala Gly Asn
        435                 440                 445

Phe Gly Thr Leu Gly Asp Pro Tyr Lys Gly Phe Pro Ser Ala Tyr Ser
    450                 455                 460

Phe Met Asp Asp
465

<210> SEQ ID NO 22
<211> LENGTH: 873
<212> TYPE: PRT
<213> ORGANISM: Gossypium hirsutum

<400> SEQUENCE: 22

Met Glu Val Ala Val Ile Gly Gly Gly Ile Lys Gly Leu Leu Ser Ala
1               5                   10                  15

Tyr Val Leu Val Lys Ala Gly Val Asp Val Val Tyr Glu Lys Glu
        20                  25                  30

Glu Gln Leu Gly Gly His Ala Lys Thr Val Asn Phe Asp Ala Val Asp
            35                  40                  45

Leu Asp Leu Gly Phe Leu Phe Leu Asn Pro Ala Arg Tyr Ala Thr Leu
    50                  55                  60

Leu His Met Phe Asp Ser Leu Gly Val Asp Val Glu Thr Ser Asp Val
65                  70                  75                  80

Ser Phe Ser Ile Ser His Asp Lys Gly Asn Asn Gly Tyr Glu Trp Cys
                85                  90                  95

Ser Gln Tyr Gly Phe Ser Asn Tyr Phe Ala Gln Lys Lys Lys Leu Leu
            100                 105                 110

Asn Pro Phe Asn Trp Gln Ser Leu Arg Glu Ile Ile Lys Phe Gly Asn
        115                 120                 125

Asp Val Glu Ser Tyr Leu Gly Ser Leu Glu Asn Asn Pro Asp Ile Asp
    130                 135                 140

Arg Thr Glu Thr Leu Gly Gln Phe Ile Asn Ser Lys Gly Tyr Ser Glu
145                 150                 155                 160

Asn Phe Gln Asn Thr Tyr Leu Ala Pro Ile Cys Gly Ser Met Trp Ser
```

```
                165                 170                 175
Ser Ser Lys Glu Asp Val Thr Ser Phe Ser Ala Phe Ser Ile Leu Ser
            180                 185                 190

Phe Cys Arg Thr His His Leu Tyr Gln Leu Phe Gly Gln Ser Gln Trp
            195                 200                 205

Leu Thr Ile Lys Gly His Ser His Phe Val Lys Val Arg Glu Val
210                 215                 220

Leu Glu Thr Lys Gly Cys Gln Phe Lys Leu Gly Cys Glu Val Gln Ser
225                 230                 235                 240

Val Leu Pro Val Asp Asn Gly Thr Ala Met Val Cys Gly Asp Gly Phe
            245                 250                 255

Gln Glu Thr Tyr Asn Gly Cys Ile Met Ala Val Asp Ala Pro Thr Ala
            260                 265                 270

Leu Lys Leu Leu Gly Asn Gln Ala Thr Phe Glu Glu Thr Arg Val Leu
            275                 280                 285

Gly Ala Phe Gln Tyr Ala Thr Ser Asp Ile Phe Leu His Gln Asp Ser
            290                 295                 300

Thr Leu Met Pro Gln Asn Lys Ser Ala Trp Ser Ala Leu Asn Phe Leu
305                 310                 315                 320

Asn Ser Ser Lys Asn Asn Ala Phe Leu Thr Tyr Trp Leu Asn Ala Leu
                325                 330                 335

Gln Asn Ile Gly Lys Thr Ser Glu Pro Phe Phe Val Thr Val Asn Pro
            340                 345                 350

Asp His Thr Pro Lys Asn Thr Leu Leu Lys Trp Ser Thr Gly His Ala
            355                 360                 365

Ile Pro Ser Val Ala Ala Ser Lys Ala Ser Leu Glu Leu Gly Gln Ile
370                 375                 380

Gln Gly Lys Arg Gly Ile Trp Phe Cys Gly Tyr Asp Phe Asn Gln Asp
385                 390                 395                 400

Glu Leu Lys Ala Gly Met Asp Ala Ala His Gly Ile Leu Gly Lys His
            405                 410                 415

Ser Ser Val Pro Pro Ser Pro Lys Asn Met Ser Pro Ser Leu Pro Lys
            420                 425                 430

Asn Met Ser Pro Ser Phe Met Glu Thr Thr Ala Arg Leu Phe Val Thr
            435                 440                 445

Lys Phe Phe Gln Gln Tyr Ile Ser Met Gly Cys Val Ile Phe Leu Glu
            450                 455                 460

Glu Gly Gly Arg Ile Phe Thr Phe Lys Gly Asn Met Glu Lys Cys Pro
465                 470                 475                 480

Leu Lys Thr Val Leu Lys Val His Asn Pro Gln Phe Tyr Trp Arg Ile
                485                 490                 495

Met Lys Glu Ala Asp Ile Gly Leu Ala Asp Ala Tyr Ile His Gly Asp
            500                 505                 510

Phe Ser Phe Leu Asp Glu Asn Glu Gly Leu Leu Asn Leu Phe Arg Ile
            515                 520                 525

Leu Val Ala Asn Lys Glu Asn Ser Ala Ala Ser Gly Ser Thr Lys Arg
            530                 535                 540

Arg Thr Trp Trp Ser Pro Ala Leu Leu Thr Ala Ser Ile Ser Ser Ala
545                 550                 555                 560

Lys Tyr Phe Val Lys His Leu Leu Arg Gln Asn Thr Ile Thr Gln Ala
                565                 570                 575

Arg Arg Asn Ile Ser Arg His Tyr Asp Leu Ser Asn Glu Leu Phe Ser
            580                 585                 590
```

Leu Tyr Leu Gly Lys Met Met Gln Tyr Ser Ser Gly Val Phe Arg Thr
            595                 600                 605

Gly Glu Glu His Leu Asp Val Ala Gln Arg Arg Lys Ile Ser Ser Leu
        610                 615                 620

Ile Glu Lys Thr Arg Ile Glu Lys Trp His Glu Val Leu Asp Ile Gly
625                 630                 635                 640

Cys Gly Trp Gly Ser Leu Ala Ile Glu Thr Val Lys Arg Thr Gly Cys
                645                 650                 655

Lys Tyr Thr Gly Ile Thr Leu Ser Glu Gln Gln Leu Lys Tyr Ala Gln
            660                 665                 670

Glu Lys Val Lys Glu Ala Gly Leu Glu Asp Asn Ile Lys Ile Leu Leu
        675                 680                 685

Cys Asp Tyr Arg Gln Leu Pro Lys Glu His Gln Phe Asp Arg Ile Ile
    690                 695                 700

Ser Val Glu Met Val Glu His Val Gly Glu Glu Tyr Ile Glu Glu Phe
705                 710                 715                 720

Tyr Arg Cys Cys Asp Gln Leu Leu Lys Glu Asp Gly Leu Phe Val Leu
                725                 730                 735

Gln Phe Ile Ser Ile Pro Glu Glu Leu Ser Lys Glu Ile Gln Gln Thr
            740                 745                 750

Ala Gly Phe Leu Lys Glu Tyr Ile Phe Pro Gly Gly Thr Leu Leu Ser
        755                 760                 765

Leu Asp Arg Asn Leu Ser Ala Met Ala Ala Thr Arg Phe Ser Val
    770                 775                 780

Glu His Val Glu Asn Ile Gly Met Ser Tyr Tyr His Thr Leu Arg Trp
785                 790                 795                 800

Trp Arg Lys Leu Phe Leu Lys Asn Thr Ser Lys Val Leu Ala Leu Gly
                805                 810                 815

Phe Asp Glu Lys Phe Met Arg Thr Trp Glu Tyr Tyr Phe Asp Tyr Cys
            820                 825                 830

Ala Ala Gly Phe Lys Thr Gly Thr Leu Ile Asp Tyr Gln Val Val Phe
        835                 840                 845

Ser Arg Ala Gly Asn Phe Gly Thr Leu Gly Asp Pro Tyr Lys Gly Phe
    850                 855                 860

Pro Ser Ala Tyr Ser Phe Met Asp Asp
865                 870

<210> SEQ ID NO 23
<211> LENGTH: 1407
<212> TYPE: DNA
<213> ORGANISM: Gossypium hirsutum

<400> SEQUENCE: 23
atggatgctg cacatggtat cttgggaaag cattcttctg ttccgcccag tccaaagaat    60
atgtcaccct ctttaccaaa gaatatgtca ccctcttttca tggaaacaac ggcacgcctc   120
tttgttacca aattctttca acaatatata tctatgggct gcgtaatttt tttagaggaa   180
ggaggcagaa ttttcacttt caaaggaaac atggaaaagt gtcctcttaa aacagttctg   240
aaagtgcata atcctcagtt ttactggagg atcatgaaag aagctgatat aggccttgca   300
gacgcatata tccatggaga ttttttcttt cttgatgaaa atgaaggcct tcttaatctt   360
ttccggattc ttgttgccaa taagagaaac tcagctgcct cagggtcgac taaagaagg   420 acttggtggt cgcctgctct gttaacagct agtatatcat ctgccaagta ttttgtgaag   480

| | |
|---|---|
| catctcttaa gacaaaatac tattacacaa gctcgtagga acatttctcg tcattatgat | 540 |
| ctgagtaatg aacttttctc tctatacttg ggcaaaatga tgcaatactc ttctggagtc | 600 |
| tttaggacag gagaagaaca tttggacgtt gcacagcgaa gaaaaatcag ttctctaatt | 660 |
| gagaaaacaa ggatagagaa atggcatgaa gttctagaca ttgggtgcgg ttggggaagc | 720 |
| ttagctattg aaactgtgaa aagaacagga tgcaaatata ctggcatcac tctatcagaa | 780 |
| cagcaactga atatgctcca agaaaaagtg aaggaagctg gactcgagga taacatcaaa | 840 |
| atacttctct gtgactatcg ccagttacct aaggaacacc aatttgacag aatcatatct | 900 |
| gtagagatgg tagaacatgt tggtgaagaa tatattgagg aattttacag atgctgtgat | 960 |
| caattactga aagaagatgg acttttcgtt cttcagttca tatctatccc agaggagctt | 1020 |
| tccaaagaaa tccagcaaac agctggtttt cttaaggaat atatattccc tggtggaacc | 1080 |
| ctgctttctt tggataggaa tttatcagcc atggctgctg caacaagatt cagtgtggag | 1140 |
| catgtggaaa acataggaat gagttattac cacacactga gatggtggag aaaacttttc | 1200 |
| ctgaaaaaca caagcaaagt tctggctttg gggttcgacg agaagttcat gcggacatgg | 1260 |
| gaatactatt tcgattactg tgctgctggt tttaagacag gaacccttat agattaccag | 1320 |
| gttgtatttt ctcgagccgg taatttcggt acacttggag atccatacaa aggtttccct | 1380 |
| tctgcatatt ccttcatgga tgattga | 1407 |

<210> SEQ ID NO 24
<211> LENGTH: 2622
<212> TYPE: DNA
<213> ORGANISM: Gossypium hirsutum

<400> SEQUENCE: 24

| | |
|---|---|
| atggaagtgg ccgtgatcgg aggtgggata aaagggttgc tttcggccta cgtactggtc | 60 |
| aaagccggcg tggacgtggt ggtttacgag aaagaagaac aattaggcgg ccatgcaaag | 120 |
| actgttaact tcgacgccgt tgatttagac cttggcttct tgtttctcaa tccagcaaga | 180 |
| tatgcaacac tattgcatat gttcgacagc cttggtgttg atgtagaaac atccgatgtt | 240 |
| tcattctcta taagccatga caaaggcaac aatggctatg aatggtgcag ccaatatgga | 300 |
| ttttccaatt actttgctca aaagaagaaa ctgttgaacc ctttcaattg gcaaagcctc | 360 |
| agagagatca tcaaattcgg caatgatgtc gaaagttacc ttggatcact tgagaacaac | 420 |
| ccagacattg atcgtactga gaccttggga cagtttataa actcaagggg ctactctgaa | 480 |
| aattttcaaa acacttatct ggctcctata tgtggttcaa tgtggtcaag ctccaaggaa | 540 |
| gatgttacga gcttttcagc ttttttccatc ctttcatttt gccgtactca tcatttgtac | 600 |
| cagctatttg ggcagtcaca gtggttgact atcaaagggc actcacattt tgttaaaagg | 660 |
| gttagggaag tgctggagac taaaggttgt caatttaaac tcggttgtga agtacaatct | 720 |
| gttttgcccg ttgataatgg taccgccatg gtctgtggag atggtttcca agaaacttac | 780 |
| aatggatgca taatggctgt tgatgctccc actgccctaa aattattagg aaaccaagca | 840 |
| acatttgaag aaacaagagt actgggtgct ttccaatatg ctaccagtga tattttcctt | 900 |
| caccaggaca gtactttaat gccacaaaac aaatcagctt ggagtgcatt gaattttctc | 960 |
| aatagtagca aaaataatgc attcttaaca tactggctca atgcactaca gaatattggg | 1020 |
| aaaacaagtg agccatttttt tgtgactgtc aatccagacc ataccccgaa gaatacctta | 1080 |
| cttaagtggt caaccggcca tgcaattccc tctgttgctg catcaaaagc ttcacttgag | 1140 |
| cttggtcaga ttcagggaaa gagaggaatc tggttctgtg gctatgactt caatcaggat | 1200 |

```
gaactaaagg ctggtatgga tgctgcacat ggtatcttgg gaaagcattc ttctgttccg    1260
cccagtccaa agaatatgtc accctcttta ccaaagaata tgtcaccctc tttcatggaa    1320
acaacggcac gcctctttgt taccaaattc tttcaacaat atatatctat gggctgcgta    1380 attttttag aggaaggagg cagaattttc actttcaaag gaaacatgga aaagtgtcct    1440
cttaaaacag ttctgaaagt gcataatcct cagttttact ggaggatcat gaaagaagct    1500
gatataggcc ttgcagacgc atatatccat ggagattttt cttttcttga tgaaaatgaa    1560
ggccttctta atcttttccg gattcttgtt gccaataaag agaactcagc tgcctcaggg    1620
tcgactaaaa gaaggacttg gtggtcgcct gctctgttaa cagctagtat atcatctgcc    1680
aagtattttg tgaagcatct cttaagacaa atactatta cacaagctcg taggaacatt    1740
tctcgtcatt atgatctgag taatgaactt ttctctctat acttgggcaa atgatgcaa    1800 tactcttctg gagtctttag acaggagaa gaacatttgg acgttgcaca gcgaagaaaa    1860
atcagttctc taattgagaa acaaggata gagaaatggc atgaagttct agacattggg    1920
tgcggttggg gaagcttagc tattgaaact gtgaaaagaa caggatgcaa atatactggc    1980
atcactctat cagaacagca actgaaatat gctcaagaaa aagtgaagga agctggactc    2040
gaggataaca tcaaaatact tctctgtgac tatcgccagt tacctaagga acaccaattt    2100
gacagaatca tatctgtaga gatggtagaa catgttggtg aagaatatat tgaggaattt    2160
tacagatgct gtgatcaatt actgaaagaa gatggacttt cgttcttca gttcatatct    2220 atcccagagg agctttccaa agaaatccag caaacagctg gttttcttaa ggaatatata    2280
ttccctggtg gaaccctgct ttctttggat aggaatttat cagccatggc tgctgcaaca    2340
agattcagtg tggagcatgt ggaaaacata ggaatgagtt attaccacac actgagatgg    2400
tggagaaaac ttttcctgaa aaacacaagc aaagttctgg ctttggggtt cgacgagaag    2460
ttcatgcgga catgggaata ctatttcgat tactgtgctg ctggttttaa gacaggaacc    2520
cttatagatt accaggttgt attttctcga gccggtaatt tcggtacact tggagatcca    2580
tacaaaggtt tcccttctgc atattccttc atggatgatt ga                       2622
```

<210> SEQ ID NO 25
<211> LENGTH: 380
<212> TYPE: PRT
<213> ORGANISM: Escherichia coli

<400> SEQUENCE: 25

```
Met Ser Ser Ser Cys Ile Glu Glu Val Ser Val Pro Asp Asp Asn Trp
1               5                   10                  15

Tyr Arg Ile Ala Asn Glu Leu Leu Ser Arg Ala Gly Ile Ala Ile Asn
            20                  25                  30

Gly Ser Ala Pro Ala Asp Ile Arg Val Lys Asn Pro Asp Phe Phe Lys
        35                  40                  45

Arg Val Leu Gln Glu Gly Ser Leu Gly Leu Gly Glu Ser Tyr Met Asp
    50                  55                  60

Gly Trp Trp Glu Cys Asp Arg Leu Asp Met Phe Phe Ser Lys Val Leu
65                  70                  75                  80

Arg Ala Gly Leu Glu Asn Gln Leu Pro His His Phe Lys Asp Thr Leu
                85                  90                  95

Arg Ile Ala Gly Ala Arg Leu Phe Asn Leu Gln Ser Lys Lys Arg Ala
            100                 105                 110

Trp Ile Val Gly Lys Glu His Tyr Asp Leu Gly Asn Asp Leu Phe Ser
```

```
            115                 120                 125
Arg Met Leu Asp Pro Phe Met Gln Tyr Ser Cys Ala Tyr Trp Lys Asp
130                 135                 140

Ala Asp Asn Leu Glu Ser Ala Gln Gln Ala Lys Leu Lys Met Ile Cys
145                 150                 155                 160

Glu Lys Leu Gln Leu Lys Pro Gly Met Arg Val Leu Asp Ile Gly Cys
                165                 170                 175

Gly Trp Gly Gly Leu Ala His Tyr Met Ala Ser Asn Tyr Asp Val Ser
            180                 185                 190

Val Val Gly Val Thr Ile Ser Ala Glu Gln Gln Lys Met Ala Gln Glu
        195                 200                 205

Arg Cys Glu Gly Leu Asp Val Thr Ile Leu Leu Gln Asp Tyr Arg Asp
210                 215                 220

Leu Asn Asp Gln Phe Asp Arg Ile Val Ser Val Gly Met Phe Glu His
225                 230                 235                 240

Val Gly Pro Lys Asn Tyr Asp Thr Tyr Phe Ala Val Val Asp Arg Asn
                245                 250                 255

Leu Lys Pro Glu Gly Ile Phe Leu Leu His Thr Ile Gly Ser Lys Lys
            260                 265                 270

Thr Asp Leu Asn Val Asp Pro Trp Ile Asn Lys Tyr Ile Phe Pro Asn
        275                 280                 285

Gly Cys Leu Pro Ser Val Arg Gln Ile Ala Gln Ser Ser Glu Pro His
290                 295                 300

Phe Val Met Glu Asp Trp His Asn Phe Gly Ala Asp Tyr Asp Thr Thr
305                 310                 315                 320

Leu Met Ala Trp Tyr Glu Arg Phe Leu Ala Ala Trp Pro Glu Ile Ala
                325                 330                 335

Asp Asn Tyr Ser Glu Arg Phe Lys Arg Met Phe Thr Tyr Leu Asn
            340                 345                 350

Ala Cys Ala Gly Ala Phe Arg Ala Arg Asp Ile Gln Leu Trp Gln Val
        355                 360                 365

Val Phe Ser Arg Gly Val Glu Asn Gly Leu Arg Val
370                 375                 380

<210> SEQ ID NO 26
<211> LENGTH: 1140
<212> TYPE: DNA
<213> ORGANISM: Artificial
<220> FEATURE:
<223> OTHER INFORMATION: Codon optimized E. Coli CPFAS open reading
      frame for plant expression

<400> SEQUENCE: 26
atgtcatcct cctgcatcga agaagtttct gttccagacg ataactggta cagaattgcc    60
aacgaattat tgtccagagc tggtattgct attaacggtt ctgctccagc tgatattaga   120
gttaagaacc cagacttctt caagagagta ttgcaagaag ttctttgggt ttgggtgaa    180 tcttatatgg atggttggtg ggaatgcgat agattggata tgttcttctc aaaggttttg   240
agagccggtt tggaaaatca attgccacat catttcaagg acaccttgag aattgctggt   300
gctagattat tcaacttgca atctaagaag agagcctgga tcgttggtaa gaacattac    360 gatttgggta cgacttgtt ctccagaatg ttggatccat tcatgcaata ctcttgtgct   420
tactggaagg atgctgataa tttggaatct gctcaacaag ccaagttgaa gatgatttgc   480
gaaaagttgc aattgaagcc aggtatgaga gttttggata ttggttgtgg ttggggtggt   540
```

```
ttggctcatt atatggcttc taactacgat gtttccgttg ttggtgttac catttctgct    600
gaacaacaaa agatggctca agaaagatgc gaaggtttgg atgttaccat cttgttgcaa    660
gattacagag acttgaacga ccaattcgat agaatcgttt ccgttggtat gttcgaacat    720
gttggtccaa agaactacga tacttacttc gctgttgtcg acagaaattt gaagccagaa    780 ggtatttttct tgttgcatac catcggttcc aaaaagaccg atttgaatgt agatccttgg    840
atcaacaagt acatctttcc aaatggttgc ttgccatccg ttagacaaat tgctcaatct    900
tctgaaccac acttcgttat ggaagattgg cataatttcg gtgctgatta cgatacaact    960
ttgatggctt ggtacgaaag attttttggct gcttggccag aaattgctga taattactcc   1020
gaaagattca agagaatgtt cacctactac ttgaatgctt gtgctggtgc ttttagagcc   1080
agagatattc aattgtggca agttgttttc tccagaggtg ttgaaaacgg tttgagagtt   1140
```

```
<210> SEQ ID NO 27
<211> LENGTH: 172
<212> TYPE: PRT
<213> ORGANISM: Cymbidium ringspot virus

<400> SEQUENCE: 27

Met Glu Arg Ala Ile Gln Gly Ser Asp Val Arg Glu Gln Ala Asp Ser
1               5                   10                  15

Glu Cys Trp Asp Gly Gly Gly Gly Thr Thr Ser Pro Phe Lys Leu
            20                  25                  30

Pro Asp Glu Ser Pro Ser Leu His Glu Trp Arg Leu His His Ser Glu
        35                  40                  45

Glu Ser Glu Asn Lys Asp Asn Pro Leu Gly Phe Lys Glu Ser Trp Ser
    50                  55                  60

Phe Gly Lys Val Val Phe Lys Arg Tyr Leu Arg Tyr Asp Gly Ala Glu
65                  70                  75                  80

Thr Ser Leu His Arg Ala Leu Gly Ser Trp Glu Arg Asp Ser Val Asn
                85                  90                  95

Asp Ala Ala Ser Arg Phe Leu Gly Leu Ser Gln Ile Gly Cys Thr Tyr
            100                 105                 110

Ser Ile Arg Phe Arg Gly Thr Arg Leu Thr Leu Ser Gly Gly Ser Gly
        115                 120                 125

Thr Leu Gln Arg Leu Ile Glu Met Ala Ile Arg Thr Lys Arg Thr Met
    130                 135                 140

Leu Gln Pro Thr Pro Ser Glu Arg Gly Asn Val Ser Arg Arg Arg
145                 150                 155                 160

Pro Glu Gly Thr Glu Ala Phe Lys Glu Glu Ser Glu
                165                 170
```

```
<210> SEQ ID NO 28
<211> LENGTH: 172
<212> TYPE: PRT
<213> ORGANISM: Pelargonium necrotic spot virus

<400> SEQUENCE: 28

Met Glu Arg Ala Val Gln Gly Gly Asp Ala Arg Glu Gln Ala Asn Ser
1               5                   10                  15

Glu Arg Trp Asp Gly Gly Cys Gly Gly Thr Ile Thr Pro Phe Lys Leu
            20                  25                  30

Ser Asp Glu Ser Pro Ser Leu His Glu Trp Arg Leu His His Ser Glu
        35                  40                  45

Glu Gly Glu Asp Gln Asp His Pro Leu Gly Phe Lys Glu Ser Trp Ser
```

```
            50                  55                  60
Phe Gly Lys Val Val Phe Lys Arg Tyr Leu Arg Tyr Gly Gly Thr Glu
 65                  70                  75                  80

Thr Ser Leu His Arg Ala Leu Gly Ser Trp Glu Arg Asn Thr Val Asn
                 85                  90                  95

Asn Ala Ala Ser Arg Phe Leu Gly Phe Gly Gln Ile Gly Cys Thr Tyr
            100                 105                 110

Ser Ile Arg Phe Arg Gly Ser Cys Leu Thr Ile Ser Gly Gly Ser Arg
        115                 120                 125

Thr Leu Gln Arg Leu Ile Glu Met Ala Ile Arg Thr Lys Cys Thr Val
    130                 135                 140

Leu Gln Leu Thr Pro Ser Glu Val Glu Gly Asn Val Ser Gly Gly Ser
145                 150                 155                 160

Pro Glu Gly Ile Glu Ala Phe Glu Lys Glu Ser Glu
                165                 170
```

<210> SEQ ID NO 29
<211> LENGTH: 172
<212> TYPE: PRT
<213> ORGANISM: Havel river tombusvirus

<400> SEQUENCE: 29

```
Met Glu Gly Ala Ile Gln Gly Ser Asp

```
                35                  40                  45
Glu Ser Glu Asp Lys Asp His Pro Leu Gly Phe Lys Glu Ser Trp Ser
 50                  55                  60

Phe Gly Lys Val Val Phe Lys Arg Tyr Leu Arg Tyr Asp Gly Thr Glu
 65                  70                  75                  80

Thr Ser Leu His Arg Ala Leu Gly Ser Trp Glu Arg Ser Thr Val Asn
                 85                  90                  95

Asp Ala Ala Ser Arg Phe Leu Gly Phe Gly Gln Ile Gly Cys Thr Tyr
                100                 105                 110

Ser Ile Arg Phe Arg Gly Ser Cys Leu Thr Leu Ser Gly Gly Ser Arg
                115                 120                 125

Thr Leu Gln Arg Leu Ile Glu Met Ala Ile Arg Thr Lys Tyr Thr Met
                130                 135                 140

Leu Gln Leu Thr Pro Ser Glu Val Glu Gly Asp Val Ser Arg Gly Cys
145                 150                 155                 160

Pro Glu Gly Ser Glu Ala Phe Lys Thr Lys Glu Ser Glu
                165                 170
```

<210> SEQ ID NO 31
<211> LENGTH: 172
<212> TYPE: PRT
<213> ORGANISM: Grapevine Algerian latent virus

<400> SEQUENCE: 31

```
Met Glu Arg Thr Ile Gln Gly Ser Asp Val Arg Glu Gln Ala Asn Ser
 1               5                  10                  15

Glu Arg Trp Asp Gly Gly Cys Gly Ser Thr Ile Thr Pro Phe Lys Leu
                20                  25                  30

Pro Asp Glu Ser Pro Ser Leu Tyr Glu Trp Arg Leu His Asn Ser Glu
                35                  40                  45

Glu Ser Glu Asp Lys Asp His Pro Leu Gly Phe Lys Glu Ser Trp Cys
 50                  55                  60

Phe Gly Lys Val Val Phe Lys Arg Tyr Leu Arg Tyr Asp Gly Thr Glu
 65                  70                  75                  80

Ala Ser Leu His Arg Ala Leu Gly Ser Trp Glu Arg Ser Ser Val Asn
                 85                  90                  95

Asp Ala Ala Ser Arg Phe Leu Gly Leu Gly Gln Ile Gly Cys Thr Tyr
                100                 105                 110

Ser Ile Arg Phe Arg Gly Ser Cys Leu Thr Leu Ser Gly Gly Ser Arg
                115                 120                 125

Thr Leu Gln Arg Leu Ile Glu Met Ala Ile Arg Thr Lys Cys Thr Met
                130                 135                 140

Leu Gln Leu Ala Pro Cys Glu Val Glu Ser Asp Val Ser Arg Arg Cys
145                 150                 155                 160

Pro Glu Gly Thr Glu Ala Phe Glu Lys Glu Ser Glu
                165                 170
```

<210> SEQ ID NO 32
<211> LENGTH: 172
<212> TYPE: PRT
<213> ORGANISM: Pear latent virus

<400> SEQUENCE: 32

```
Met Glu Arg Ala Ile Gln Gly Ser Asp Ala Arg Glu Gln Ala Tyr Ser
 1               5                  10                  15

Glu Arg Trp Asp Gly Gly Cys Gly Gly Thr Ile Thr Pro Phe

```
                    20                  25                  30
Pro Asp Glu Ser Pro Ser Leu Ile Glu Trp Arg Leu His Asn Ser Glu
            35                  40                  45

Glu Ser Glu Asp Lys Asp Asn Pro Leu Gly Phe Lys Glu Ser Trp Ser
        50                  55                  60

Phe Gly Lys Val Val Phe Lys Arg Tyr Leu Arg Tyr Asp Gly Thr Glu
65                  70                  75                  80

Ala Ser Leu His Arg Ala Leu Gly Ser Trp Glu Arg Asp Thr Val Asn
                85                  90                  95

Asn Ala Ala Ser Arg Phe Leu Gly Phe Gly Gln Ile Gly Cys Thr Tyr
            100                 105                 110

Cys Ile Arg Phe Arg Gly Ser Cys Leu Thr Ile Ser Gly Gly Ser Arg
        115                 120                 125

Thr Leu Gln Arg Leu Ile Glu Met Ala Ile Arg Thr Lys Arg Thr Met
    130                 135                 140

Leu Gln Leu Thr Pro Cys Glu Val Gly Asn Val Ser Arg Gly Ser
145                 150                 155                 160

Pro Glu Gly Thr Glu Ala Phe Lys Glu Glu Ser Glu
                165                 170

<210> SEQ ID NO 33
<211> LENGTH: 172
<212> TYPE: PRT
<213> ORGANISM: Lisianthus necrotic virus

<400> SEQUENCE: 33

Met Glu Arg Ala Ile Gln Gly Ser Asp Ala Arg Glu Gln Ala Tyr Ser
1               5                   10                  15

Glu Arg Trp Asp Gly Gly Cys Gly Gly Thr Ile Thr Pro Phe Lys Leu
            20                  25                  30

Pro Asp Glu Ser Pro Ser Leu Ile Glu Trp Arg Leu His Asn Ser Glu
        35                  40                  45

Glu Ser Glu Asp Lys Asp Asn Pro Leu Gly Phe Lys Glu Ser Trp Ser
    50                  55                  60

Phe Gly Lys Val Val Phe Lys Arg Tyr Leu Arg Tyr Asp Gly Thr Glu
65                  70                  75                  80

Ala Ser Leu His Arg Ala Leu Gly Ser Trp Glu Arg Asp Thr Val Asn
                85                  90                  95

Asp Ala Ala Ser Arg Phe Leu Gly Phe Gly Gln Ile Gly Cys Thr Tyr
            100                 105                 110

Cys Ile Arg Phe Arg Gly Ser Cys Leu Thr Ile Ser Gly Gly Ser Arg
        115                 120                 125

Thr Leu Gln Arg Leu Ile Glu Met Ala Ile Arg Thr Lys Arg Thr Met
    130                 135                 140

Leu Gln Leu Ala Pro Cys Glu Val Gly Asn Val Ser Arg Gly Ser
145                 150                 155                 160

Pro Glu Gly Thr Glu Ala Phe Lys Glu Glu Ser Glu
                165                 170

<210> SEQ ID NO 34
<211> LENGTH: 172
<212> TYPE: PRT
<213> ORGANISM: Lettuce necrotic stunt virus

<400> SEQUENCE: 34

Met Glu Arg Ala Ile Gln Gly Asn Asp Ala Arg Glu Gln Ala Asn Ser
```

```
              1               5              10              15
            Glu Arg Trp Asn Gly Gly Ser Gly Gly Ser Ala Ser Pro Phe Lys Phe
                            20                  25                  30

Pro Asp Glu Ser Pro Ser Trp Thr Glu Trp Arg Leu His Asn Asp Glu
                            35                  40                  45

Thr Asn Ser Asn Gln Asp Asn Pro Leu Gly Phe Lys Glu Ser Trp Gly
                            50                  55                  60

Phe Gly Lys Val Val Phe Lys Arg Tyr Leu Arg Tyr Asp Gly Thr Glu
             65                  70                  75                  80

Ala Ser Leu His Arg Val Leu Gly Ser Trp Thr Gly Asp Ser Val Asn
                                85                  90                  95

Tyr Ala Ala Ser Arg Phe Phe Gly Ile Asn Gln Ile Gly Cys Thr Tyr
                            100                 105                 110

Ser Ile Arg Phe Arg Gly Val Ser Val Thr Ile Ser Gly Gly Ser Arg
                            115                 120                 125

Ala Leu Gln His Leu Cys Glu Met Ala Val Arg Ala Lys Gln Glu Leu
                            130                 135                 140

Leu Gln Leu Thr Pro Val Glu Val Glu Ser Asn Val Ser Arg Arg Cys
            145                 150                 155                 160

Pro Glu Gly Phe Glu Ala Phe Glu Lys Glu Ser Glu
                            165                 170

<210> SEQ ID NO 35
<211> LENGTH: 172
<212> TYPE: PRT
<213> ORGANISM: Artichoke Mottled Crinkle Virus

<400> SEQUENCE: 35

Met Glu Arg Val Ile Gln Gly Asn Asp Ala Arg Glu Gln Ala Asn Gly
             1               5                  10                  15

Glu Arg Trp Asp Gly Gly Ser Gly Gly Thr Thr Ser Pro Phe Lys Leu
                            20                  25                  30

Pro Asp Glu Ser Pro Ser Trp Thr Glu Trp Arg Ile His Asn Asp Glu
                            35                  40                  45

Thr Asp Ser Asn Lys Asp Asn Pro Leu Gly Phe Lys Glu Ser Trp Gly
             50                  55                  60

Phe Gly Lys Val Val Phe Lys Arg Tyr Leu Arg Tyr Asp Arg Thr Glu
             65                  70                  75                  80

Thr Ser Leu His Arg Val Leu Gly Ser Trp Thr Gly Asp Ser Val Asn
                                85                  90                  95

Tyr Ala Ala Ser Arg Phe Leu Gly Val Asn Gln Ile Gly Cys Thr Tyr
                            100                 105                 110

Ser Ile Arg Phe Arg Gly Val Ser Val Thr Ile Ser Gly Gly Ser Arg
                            115                 120                 125

Thr Leu Gln His Leu Cys Glu Met Ala Ile Arg Ser Lys Gln Glu Leu
                            130                 135                 140

Leu Gln Leu Ala Pro Val Glu Val Glu Ser Asn Val Ser Arg Gly Arg
            145                 150                 155                 160

Pro Glu Gly Ala Glu Ala Phe Lys Glu Glu Ser Glu
                            165                 170

<210> SEQ ID NO 36
<211> LENGTH: 172
<212> TYPE: PRT
<213> ORGANISM: Carnation Italian ringspot virus
```

<400> SEQUENCE: 36

```
Met Glu Arg Ala Ile Gln Gly Asn Gln Ala Arg Glu Gln Ala Asn Gly
1               5                   10                  15

Glu Arg Trp Asp Gly Gly Ser Gly Gly Thr Thr Ser Pro Phe Lys Leu
            20                  25                  30

Ser Asp Glu Ser Pro Ser Trp Thr Glu Trp Arg Leu His Asn Asp Glu
        35                  40                  45

Thr Asn Ser Asn Gln Asp Asn Pro Leu Gly Phe Lys Glu Ser Trp Gly
    50                  55                  60

Phe Gly Lys Val Val Phe Lys Arg Tyr Leu Arg Tyr Asp Arg Thr Glu
65                  70                  75                  80

Thr Ser Leu His Arg Val Leu Gly Ser Trp Thr Gly Asn Ser Val Asn
                85                  90                  95

Tyr Ala Ala Ser Arg Phe Phe Gly Val Asn Gln Ile Gly Cys Thr Tyr
            100                 105                 110

Ser Ile Arg Phe Arg Gly Val Ser Val Thr Ile Ser Gly Gly Ser Arg
        115                 120                 125

Thr Leu Gln His Leu Cys Glu Met Ala Ile Arg Ser Lys Gln Glu Leu
    130                 135                 140

Leu Gln Leu Thr Pro Val Glu Val Glu Ser Asn Val Ser Arg Gly Cys
145                 150                 155                 160

Pro Glu Gly Ala Glu Ala Phe Glu Glu Glu Ser Glu
                165                 170
```

<210> SEQ ID NO 37
<211> LENGTH: 170
<212> TYPE: PRT
<213> ORGANISM: Maize necrotic streak virus

<400> SEQUENCE: 37

```
Met Glu Arg Ala Ile Gln Gly Ser Asp Ala Trp Gln Gln Thr Gly Gly
1               5                   10                  15

Gln Arg Arg Val Gly Gly Cys Gly Asp Ser Phe Ala Pro Phe Gln Leu
            20                  25                  30

Pro Asp Glu Ser Pro Thr Ser Asp Glu Trp Arg Leu His His Asp Ala
        35                  40                  45

Tyr Asp Pro Asp Thr Asp Cys Pro Leu Gly Phe Lys Glu Phe Trp Ser
    50                  55                  60

Val Gly Lys Ala Ile Ser Lys Arg Tyr His Arg Tyr Asp Trp Lys Glu
65                  70                  75                  80

Ala Ser Leu Asp Arg Ala Leu Gly Ser Trp Gln Gly Asp Lys Val Ile
                85                  90                  95

Thr Glu Ala Ser Arg Phe Leu Gly Val Asp Gln Val Ser Cys Thr Tyr
            100                 105                 110

Ser Ile Arg Val Arg Gly Val Ser Ile Thr Leu Ser Gly Gly Ser Arg
        115                 120                 125

Ala Leu Leu Arg Leu Val Ser Met Ala Asp Arg Ile Lys Arg Ser Glu
    130                 135                 140

Leu Gln Phe Ala Thr Ser Ala Val Glu Ser Val Val Ser Arg Gly Cys
145                 150                 155                 160

Pro Glu Glu Glu Thr Pro Lys Glu Ser Glu
                165                 170
```

<210> SEQ ID NO 38
<211> LENGTH: 119

```
<212> TYPE: PRT
<213> ORGANISM: Watermelon chlorotic stunt virus

<400> SEQUENCE: 38

Met Trp Asp Pro Leu Leu Asn Asp Phe Pro Glu Ser Val His Gly Phe
1               5                   10                  15

Arg Cys Met Leu Ala Val Lys Tyr Leu Gln Ala Val Glu Ser Thr Tyr
            20                  25                  30

Glu Pro Asn Thr Leu Gly His Glu Leu Ile Arg Asp Leu Ile Leu Val
        35                  40                  45

Leu Arg Ala Arg Asp Tyr Gly Glu Ala Asn Arg Arg Tyr Ser His Phe
    50                  55                  60

His Ser Arg Phe Glu Gly Ser Ser Lys Thr Glu Leu Arg Gln Pro Leu
65                  70                  75                  80

His Glu Pro Cys Cys Cys Pro His Cys Pro Gly His Lys Gln Ala Ser
                85                  90                  95

Thr Met Gly Gln Gln Ala His Val Ser Lys Ala Gln Asp Val Gln Asp
            100                 105                 110

Val Ser Lys Pro Arg Cys Pro
            115

<210> SEQ ID NO 39
<211> LENGTH: 116
<212> TYPE: PRT
<213> ORGANISM: Okra yellow crinkle virus

<400> SEQUENCE: 39

Met Trp Asp Pro Leu Val Asn Glu Phe Pro Glu Ser Val His Gly Phe
1               5                   10                  15

Arg Cys Met Leu Ala Ile Lys Tyr Leu Gln Ala Leu Glu Asp Thr Tyr
            20                  25                  30

Glu Pro Asn Thr Leu Gly Ser Asp Leu Ile Arg Asp Leu Ile Ser Val
        35                  40                  45

Ile Arg Ala Lys Asn Tyr Val Glu Ala Thr Arg Arg Tyr Asn Phe Phe
    50                  55                  60

His Ala Arg Leu Glu Gly Ser Ser Lys Ala Glu Leu Arg Gln Pro Leu
65                  70                  75                  80

His Glu Pro Cys Asn Cys Pro His Cys Pro Arg His Lys Gln Thr Ser
                85                  90                  95

Val Met Asp Ser Pro Ala Asn Val Gln Lys Ala Gln Asn Val Pro Asp
            100                 105                 110

Val Gln Lys Pro
            115

<210> SEQ ID NO 40
<211> LENGTH: 116
<212> TYPE: PRT
<213> ORGANISM: Okra leaf curl virus

<400> SEQUENCE: 40

Met Trp Asp Pro Leu Val Asn Glu Phe Pro Glu Ser Val His Gly Phe
1               5                   10                  15

Arg Cys Met Leu Ala Ile Lys Tyr Leu Gln Ala Leu Glu Asp Thr Tyr
            20                  25                  30

Glu Pro Asn Thr Leu Gly Ser Asp Leu Ile Arg Asp Leu Ile Ser Val
        35                  40                  45

Ile Arg Ala Lys Asn Tyr Val Glu Ala Thr Arg Arg Tyr Asn Tyr Phe
```

```
                 50                  55                  60
His Ala Arg Leu Glu Gly Ser Ser Lys Ala Glu Leu Arg Gln Pro Leu
 65                  70                  75                  80

His Glu Pro Cys Asn Cys Pro His Cys Pro Arg His Lys Gln Thr Ser
                 85                  90                  95

Val Met Asp Leu Pro Ala Asn Val Gln Lys Ala Gln Asn Val Pro Asp
                100                 105                 110

Val Gln Lys Pro
        115

<210> SEQ ID NO 41
<211> LENGTH: 116
<212> TYPE: PRT
<213> ORGANISM: Tomato leaf curl Togo virus

<400> SEQUENCE: 41

Met Trp Asp Pro Leu Leu Asn Glu Phe Pro Asp Ser Val His Gly Phe
 1               5                  10                  15

Arg Cys Met Leu Gly Ile Lys Tyr Leu Gln Leu Leu Glu Glu Glu Tyr
                 20                  25                  30

Glu Pro Asn Thr Leu Gly His Asp Leu Val Arg Asp Leu Ile Ser Val
                 35                  40                  45

Val Arg Ala Lys Asn Tyr Val Glu Ala Thr Arg Arg Tyr Asn Asn Phe
 50                  55                  60

His Ala Arg Leu Glu Gly Ala Ser Thr Ala Glu Leu Arg Gln Pro Leu
 65                  70                  75                  80

Arg Gln Pro Cys Cys Cys Pro His Cys Pro Arg His Lys Gln Ala Ser
                 85                  90                  95

Phe Val Asp Val Pro Ala His Val Ser Gln Ala Lys Asn Val Gln Asp
                100                 105                 110

Val Gln Asn Ser
        115

<210> SEQ ID NO 42
<211> LENGTH: 116
<212> TYPE: PRT
<213> ORGANISM: Ageratum leaf curl Cameroon virus

<400> SEQUENCE: 42

Met Trp Asp Pro Leu Leu Asn Glu Phe Pro Asp Ser Val His Gly Phe
 1               5                  10                  15

Arg Cys Met Leu Gly Ile Lys Tyr Leu Gln Leu Leu Glu Glu Glu Tyr
                 20                  25                  30

Glu Pro Asn Thr Leu Gly His Asp Leu Ile Arg Asp Leu Ile Ser Val
                 35                  40                  45

Ile Arg Ala Lys Asn Tyr Val Glu Ala Thr Arg Arg Tyr Asn Asn Phe
 50                  55                  60

His Ala Arg Leu Glu Gly Ala Ser Thr Ser Glu Leu Arg Gln Pro Leu
 65                  70                  75                  80

His Gln Pro Cys Cys Cys Pro His Cys Pro Arg His Lys Gln Ala Ser
                 85                  90                  95

Phe Met Asp Val Pro Ala His Val Pro Lys Ala Gln Asn Val Pro Asp
                100                 105                 110

Val Gln Asn Pro
        115
```

-continued

```
<210> SEQ ID NO 43
<211> LENGTH: 116
<212> TYPE: PRT
<213> ORGANISM: East African cassava mosaic Malawi virus

<400> SEQUENCE: 43

Met Trp Asp Pro Leu Leu Asn Glu Phe Pro Asp Ser Val His Gly Phe
1               5                   10                  15

Arg Cys Met Leu Ala Ile Lys Tyr Leu Gln Ala Leu Glu Glu Thr Tyr
            20                  25                  30

Glu Pro Asn Thr Leu Gly His Asp Leu Val Arg Asp Leu Ile Cys Val
        35                  40                  45

Ile Arg Ala Arg Asp Tyr Val Glu Ala Thr Arg Arg Tyr Asn His Phe
    50                  55                  60

His Ser Arg Leu Glu Gly Ala Ser Lys Ala Glu Leu Arg Gln Pro Val
65                  70                  75                  80

Gln Gln Pro Cys Cys Cys Pro His Cys Pro Arg His Lys Gln Ala Thr
                85                  90                  95

Ile Met Asp Val Pro Ala His Val Ser Lys Ala Gln Asn Val Gln Asn
            100                 105                 110

Val Gln Lys Ser
        115

<210> SEQ ID NO 44
<211> LENGTH: 116
<212> TYPE: PRT
<213> ORGANISM: South African cassava mosaic virus

<400> SEQUENCE: 44

Met Trp Asp Pro Leu Val Asn Glu Phe Pro Glu Ser Val His Gly Phe
1               5                   10                  15

Arg Cys Met Leu Ala Ile Lys Tyr Leu Gln Ala Val Glu Glu Thr Tyr
            20                  25                  30

Glu Pro Asn Thr Leu Gly His Asp Leu Val Arg Asp Leu Ile Cys Val
        35                  40                  45

Leu Arg Ala Arg Asp Tyr Val Glu Ala Thr Arg Arg Tyr Asn His Phe
    50                  55                  60

His Ser Arg Leu Glu Gly Ala Thr Lys Ala Glu Leu Arg Gln Pro Val
65                  70                  75                  80

Gln Gln Pro Cys Cys Cys Pro His Cys Pro Arg His Lys Gln Ala Pro
                85                  90                  95

Ile Met Asp Val Thr Ala His Val Ser Lys Ala Gln Asn Val Gln Asn
            100                 105                 110

Val Gln Lys Ser
        115

<210> SEQ ID NO 45
<211> LENGTH: 116
<212> TYPE: PRT
<213> ORGANISM: Tomato leaf curl Madagascar virus

<400> SEQUENCE: 45

Met Trp Asp Pro Leu Leu Asn Glu Phe Pro Asp Ser Val His Gly Phe
1               5                   10                  15

Arg Cys Met Leu Ala Val Lys Tyr Leu Gln Ala Val Glu Glu Thr Tyr
            20                  25                  30

Glu Pro Asn Thr Leu Gly His Asp Leu Ile Arg Asp Leu Ile Ser Val
        35                  40                  45
```

```
Ile Arg Ala Arg Asp Tyr Val Glu Ala Thr Arg Arg Tyr Asn His Phe
    50                  55                  60

His Ala Arg Leu Glu Gly Ser Ser Lys Ala Glu Leu Arg Gln Pro Ile
65                  70                  75                  80

Tyr Gln Pro Cys Cys Cys Pro His Cys Pro Arg His Lys Gln Ala Ser
                85                  90                  95

Val Met Asp Leu Pro Ala His Val Pro Lys Ala Gln Asp Val Gln Asn
            100                 105                 110

Val Gln Lys Pro
            115

<210> SEQ ID NO 46
<211> LENGTH: 116
<212> TYPE: PRT
<213> ORGANISM: Tobacco leaf curl Zimbabwe virus

<400> SEQUENCE: 46

Met Trp Asp Pro Leu Leu Asn Glu Phe Pro Glu Ser Val His Gly Phe
1               5                   10                  15

Arg Cys Met Leu Ala Ile Lys Tyr Leu Gln Ala Val Glu Glu Ser Tyr
                20                  25                  30

Glu Pro Asn Thr Leu Gly His Asp Leu Ile Arg Asp Leu Ile Cys Val
            35                  40                  45

Ile Arg Ala Arg Asp Tyr Val Glu Ala Thr Arg Arg Tyr Asn His Phe
    50                  55                  60

His Ala Arg Leu Glu Gly Ser Ser Lys Ala Glu Leu Arg Gln Pro Ile
65                  70                  75                  80

Tyr Gln Pro Cys Cys Cys Pro His Cys Pro Arg His Lys Gln Thr Thr
                85                  90                  95

Val Val Asp Leu Pro Ala Gln Leu Pro Lys Ala Gln Asn Val Pro Asp
            100                 105                 110

Val Gln Lys Ser
            115

<210> SEQ ID NO 47
<211> LENGTH: 116
<212> TYPE: PRT
<213> ORGANISM: Tomato begomovirus

<400> SEQUENCE: 47

Met Trp Asp Pro Leu Leu Asn Glu Phe Pro Asp Ser Val His Gly Phe
1               5                   10                  15

Arg Cys Met Leu Ala Val Lys Tyr Leu Gln Ala Val Glu Glu Thr Tyr
                20                  25                  30

Glu Pro Asn Thr Leu Gly His Asp Leu Ile Arg Asp Leu Ile Ser Val
            35                  40                  45

Ile Arg Ala Arg Asp Tyr Val Glu Ala Thr Arg Arg Tyr Asn His Phe
    50                  55                  60

His Ala Arg Leu Glu Gly Ser Ser Lys Ala Glu Leu Arg Gln Pro Ile
65                  70                  75                  80

Tyr Gln Pro Cys Cys Cys Pro His Cys Pro Arg His Lys Gln Ala Ser
                85                  90                  95

Val Met Asp Leu Pro Ala His Val Pro Lys Ala Gln Asp Val Gln Asn
            100                 105                 110

Val Gln Lys Pro
            115
```

<210> SEQ ID NO 48
<211> LENGTH: 116
<212> TYPE: PRT
<213> ORGANISM: Tomato leaf curl Namakely virus

<400> SEQUENCE: 48

Met Trp Asp Pro Leu Leu Asn Glu Phe Pro Asp Ser Val His Gly Phe
1               5                   10                  15

Arg Cys Met Leu Ala Ile Lys Tyr Leu Gln Ala Ile Glu Gln Thr Tyr
            20                  25                  30

Glu Pro Asn Thr Leu Gly His Asp Leu Ile Arg Asp Leu Ile Ser Val
        35                  40                  45

Val Arg Ala Arg Asp Tyr Val Glu Ala Thr Arg Arg Tyr Asn His Phe
    50                  55                  60

His Ala Arg Phe Glu Gly Ala Ser Lys Val Glu Leu Arg Gln Pro Val
65                  70                  75                  80

Tyr Gln Pro Cys Cys Cys Pro His Cys Pro Arg His Lys Gln Thr Ser
                85                  90                  95

Val Met Asp Val Gln Ala His Val Ser Lys Ala Gln Asp Val Gln Asn
            100                 105                 110

Val Gln Lys Pro
        115

<210> SEQ ID NO 49
<211> LENGTH: 116
<212> TYPE: PRT
<213> ORGANISM: Pepper yellow vein Mali virus

<400> SEQUENCE: 49

Met Trp Asp Pro Leu Leu Asn Glu Phe Pro Asp Ser Val His Gly Phe
1               5                   10                  15

Arg Cys Met Leu Ala Ile Lys Tyr Leu Gln Ala Val Glu Asp Ser Tyr
            20                  25                  30

Glu Pro Asn Thr Leu Gly His Asp Leu Ile Arg Asp Leu Ile Cys Val
        35                  40                  45

Ile Arg Ala Arg Asp Tyr Val Glu Ala Thr Arg Arg Tyr Asn His Phe
    50                  55                  60

His Ala Arg Leu Glu Gly Ser Ser Lys Ala Glu Leu Arg Gln Pro Ile
65                  70                  75                  80

Gln Gln Pro Cys Cys Cys Pro His Cys Pro Arg His Lys Gln Ala Ser
                85                  90                  95

Ile Met Asp Leu Pro Ala His Val Ser Lys Ala Gln Asp Val Gln Asn
            100                 105                 110

Val Gln Lys Pro
        115

<210> SEQ ID NO 50
<211> LENGTH: 116
<212> TYPE: PRT
<213> ORGANISM: Tomato leaf curl Sudan virus

<400> SEQUENCE: 50

Met Trp Asp Pro Leu Leu Asn Glu Phe Pro Glu Ser Val His Gly Phe
1               5                   10                  15

Arg Cys Met Leu Ala Ile Lys Tyr Leu Gln Ala Val Glu Glu Thr Tyr
            20                  25                  30

```
Glu Pro Asn Thr Leu Gly His Asp Leu Ile Arg Asp Leu Ile Ser Val
            35                  40                  45

Val Arg Ala Ar

-continued

```
gatgccatat ctcaggagct ttcacttacc cctttaatgg cttcactctt ctatcctaga    600
attaagttgc accatctctc catccctatc tctctctctc tctatcttta gttcttttaa    660
gaatgacttt tcattttttg tgttgtctgt tgcaggtgta taaacatgga tgatggatct    720
tgagtaggat tttttatttt attttcttgt gacatatatg caatttttat ggtttgtact    780
ttgtatttcc attagtttcg tacttttcag ttatgtatca ttgttaattc taatgtttga    840
agacatttag agtttatact tctctaaatt acttttcga ctcaataaag tcgtttaagt     900
gtctgggttc gaa                                                       913

<210> SEQ ID NO 53
<211> LENGTH: 913
<212> TYPE: DNA
<213> ORGANISM: Artificial Sequence
<220> FEATURE:
<223> OTHER INFORMATION: Nucleotide sequence encoding miRNA targetting
      A. thaliana FAD2

<400> SEQUENCE: 53
actagtgatt tcactttgt tctcctcctc cctttttttc ttttcaggat tcttcttttc      60 tatgtttat ctttcataat agatctgata attttgattt ttcactatat atattatggt    120
taatactagt agcttttca tttcaagttt tatccttcca ttggttcttt ctgagtcaaa    180
ttgtctcctg tttcgaacca tatataagtt ttcaatggtt ttgtattaac tcaagtattc    240
aacattatgt ctctcttttt cttgcttgga tctctaatgc tgttcatatt ttaaagcata    300
ggtttaggtt agatgcatgt aactgccaat taaaagaagg tcaagagttt tttgattgta    360
tgaatatatg agttagtcaa agcagatcca cacgattata tagaaaaaca aaggaagaag    420
aagagggtgc aacttaaggc taggattgga gggtttagca gggtgaagta aagctgctaa    480
gctatggatc ccataagcct tatcaaattc aatataattg atgataaggt tttttttatg    540
gatgccatat ctcaggagct ttcacttacc cctttaatgg cttcactctt ctatcctaga    600
attaagttgc accatctctc catccctatc tctctctctc tctatcttta gttcttttaa    660
gaatgacttt tcattttttg tgttgtctgt tgcaggtgta taaacatgga tgatggatct    720
tgagtaggat tttttatttt attttcttgt gacatatatg caatttttat ggtttgtact    780
ttgtatttcc attagtttcg tacttttcag ttatgtatca ttgttaattc taatgtttga    840
agacatttag agtttatact tctctaaatt acttttcga ctcaataaag tcgtttaagt     900
gtctgggttc gaa                                                       913
```

SIMULTANEOUS GENE SILENCING AND SUPPRESSING GENE SILENCING IN THE SAME CELL

CROSS-REFERENCE TO RELATED APPLICATIONS

This application is a § 371 national stage of PCT International Application No. PCT/AU2012/001594, filed Dec. 21, 2012, claiming the benefit of U.S. Provisional Application No. 61/580,574, filed Dec. 27, 2011, the contents of each of which are hereby incorporated by reference in their entirety.

REFERENCE TO A SEQUENCE LISTING

This application incorporates-by-reference nucleotide and/or amino acid sequences which are present in the file named "140627_2251_83667_A_PCT_US_Substitute_Sequence_Listing_JR.txt" which is 79.9 kilobytes in size, and which was created Jun. 25, 2014 in the IBM-PC machine format, having an operating system compatibility with MS-Windows, which is contained in the text file filed Jun. 27, 2014 as part of this application.

FIELD OF THE INVENTION

The present invention relates to genetically modified cells that are capable of optimal transgene expression by co-expressing a silencing suppressor whilst at the same time are also capable of silencing a gene, such as a naturally occurring gene of the cell. The present invention also relates to methods of producing the modified cells, as well as relates to processes for obtaining a genetically modified cell with a desired property.

BACKGROUND OF THE INVENTION

The engineering of cells to express new and valuable products is a central theme in biotechnology. Such metabolic engineering places a number of competing demands on the host expression platform including i) the need for high and sustained transgene expression, ii) the assembly of complicated multigene pathways, iii) scalability allowing either high-throughput trials or larger production runs, and iv) an easily-ablated host expressome allowing both gene replacement and optimised substrate pools for newly-engineered metabolic fluxes. Transient leaf assays have emerged as a versatile expression platform for metabolic engineering by meeting the first three criteria, namely high and extended periods of transgene expression (Voinnet et al., 2003), multigene engineering and high-throughput trait optimisation (Wood et al., 2009; Petrie et al., 2010), and scaling for larger production runs as required for personalised medicines (Bakker et al., 2006).

The sustained over-expression of transgenes in leaf assays depends upon viral suppressor proteins (VSP), also known as silencing suppressors, to block the host cell silencing apparatus. The most widely used VSP is p19 that specifically binds 21 nucleotide small RNA with two nucleotide 3' overhangs (Ye et al., 2003) that are generated by the plant cell in response to the foreign transgene or hairpin RNAi. Reports have shown that although p19 enhances gene expression in leaf assays through its suppressor activity. This VSP also inhibits the effectiveness of RNAi, making it, it is thought, incompatible with simultaneous gene silencing in the same cell (Voinnet et al., 2003; Johansen and Carrington, 2001).

There is a need for methods which allow the concurrent over-expression of a transgene and the reduced expression of another gene such as an endogenous gene.

SUMMARY OF THE INVENTION

The present inventors have determined that silencing suppressor polypeptides can be co-expressed with a double stranded RNA (dsRNA) such as a hairpin RNA or microRNA precursor and at least partial silencing of a target gene achieved.

Thus, in a first aspect the present invention provides a eukaryotic cell, preferably a plant cell, comprising, i) a first exogenous polynucleotide encoding a double stranded RNA (dsRNA) molecule which comprises a first nucleotide sequence which is complementary to a region of a target RNA encoded by a first polynucleotide of interest, and ii) a second exogenous polynucleotide encoding a silencing suppressor polypeptide, wherein each exogenous polynucleotide is operably linked to one or more promoters that are capable of directing expression of the polynucleotide in the cell, and wherein the cell comprises the silencing suppressor polypeptide and the dsRNA molecule or a processed RNA product thereof which comprises the first nucleotide sequence and is capable of reducing in the cell the level of the target RNA encoded by the first polynucleotide of interest and/or the amount of a protein encoded by the target RNA when compared to a corresponding cell lacking the first exogenous polynucleotide.

As the skilled person would appreciate, the silencing suppressor polypeptide will be compatible with the dsRNA molecule, so that both can exert their effects in the same cell for at least some of the same time. Thus, in the invention the silencing suppressor exerts its suppressive effect by a mechanism that allows the double stranded RNA or the processed RNA product thereof to reduce the expression of the target RNA and/or reduce the production of a protein encoded by the target RNA.

In an embodiment, the cell further comprises the first polynucleotide of interest, wherein the cell has a reduced level of the target RNA encoded by the first polynucleotide of interest and/or a reduced amount of the protein encoded by the target RNA when compared to a corresponding cell lacking the first exogenous polynucleotide. The first polynucleotide of interest may not be present in the cell all of the time, for example if the first polynucleotide of interest is a gene of a pathogen of the cell such as a viral pathogen. In such cases, the dsRNA molecule may be produced in the cell prior to, or to protect the cell against, the presence of the first polynucleotide of interest.

In an embodiment, the first polynucleotide of interest is an endogenous gene of the cell or a transgene and/or a gene of a pathogen, such as a virus, of the cell.

In a particularly preferred embodiment, the cell, preferably a plant cell, further comprises a third exogenous polynucleotide, different to the first and second exogenous polynucleotides and the first polynucleotide of interest, which encodes an RNA of interest, such that in the cell the level of the RNA of interest and/or the amount of protein encoded by the RNA of interest is increased when compared to a corresponding cell having the third exogenous polynucleotide and lacking the second exogenous polynucleotide. That is, it is intended that the third exogenous polynucleotide is expressed at an increased level in the cell by the presence of the silencing suppressor. The cell may comprise a fourth, fifth or more exogenous polynucleotides which are similarly expressed at an increased level by the presence of the silencing suppressor.

In an embodiment, the first and second exogenous polynucleotides form part of the same DNA construct, which is preferably integrated into the genome of the cell.

In a further embodiment, the first, second and third exogenous polynucleotides form part of the same DNA construct, which is preferably integrated into the genome of the cell.

Preferably, at least the second exogenous polynucleotide is integrated into the genome of the cell.

In an embodiment, the cell, preferably a plant cell, comprises at least a 25%, preferably at least a 50%, at least a 60%, at least a 70%, at least an 80%, at least a 90%, at least a 95% reduction in the level of the target RNA encoded by the first polynucleotide of interest and/or amount of protein encoded by the target RNA when compared to a corresponding cell lacking the first exogenous polynucleotide. In another embodiment, the cell, preferably a plant cell, comprises an about 25% to about 100%, about 50% to about 100%, about 75% to about 100%, about 25% to about 90%, about 50% to about 90%, or about 75% to about 90% reduction in the level of the target RNA encoded by the first polynucleotide of interest and/or amount of protein encoded by the target RNA when compared to a corresponding cell lacking the first exogenous polynucleotide. The extent to which the target RNA is reduced can be modulated to a desired level by the structure or level of the dsRNA molecule, as desired.

In an embodiment, the silencing suppressor preferentially binds to a double-stranded RNA molecule which has overhanging 5' ends relative to a corresponding double-stranded RNA molecule having blunt ends. This is a feature of the V2 type of silencing suppressor, namely for V2 and its functional orthologs. In a further embodiment, the silencing suppressor comprises amino acids having a sequence as provided in any one of SEQ ID NOs:1, or 38 to 51, a biologically active fragment thereof, or an amino acid sequence which is at least 30% identical to any one or more of SEQ ID NOs:1, or 38 to 51.

In another embodiment, the silencing suppressor preferentially binds a dsRNA molecule which is 21 base pairs in length relative to a dsRNA molecule of a different length. This is a feature of at least the p19 type of silencing suppressor, namely for p19 and its functional orthologs. In yet a further embodiment, the silencing suppressor comprises amino acids having a sequence as provided in any one of SEQ ID NOs: 2, or 27 to 37, a biologically active fragment thereof, or an amino acid sequence which is at least 30% identical to any one or more of SEQ ID NOs: 2, or 27 to 37.

In an embodiment, the dsRNA molecule, or a processed RNA product thereof, comprises at least 19 consecutive nucleotides, preferably whose length is 19-24 nucleotides with 19-24 consecutive basepairs in the case of a double-stranded hairpin RNA molecule or processed RNA product, more preferably consisting of 20, 21, 22, 23 or 24 nucleotides in length, and preferably comprising a methylated nucleotide, which is at least 95% identical to the complement of the region of the target RNA, and wherein the region of the target RNA is i) within a 5' untranslated region of the target RNA, ii) within a 5' half of the target RNA, iii) within a protein-encoding open-reading frame of the target RNA, iv) within a 3' half of the target RNA, or v) within a 3' untranslated region of the target RNA.

In an embodiment, the dsRNA molecule is a microRNA (miRNA) precursor and/or wherein the processed RNA product thereof is a miRNA. The hybridising sequences in a miRNA precursor are not fully basepaired, having more than one non-basepaired nucleotides in each of the hybridising sequences, which form bulges in the hybridised dsRNA structure. The basepairing may include one or more G:U basepairs.

In an embodiment, the third exogenous polynucleotide encodes a protein or microRNA precursor.

In a further embodiment, the cell, preferably a plant cell, further comprises at least one, at least two, at least three, at least four or at least five additional, different exogenous polynucleotides each encoding different RNAs of interest, preferably where the additional polynucleotides form part of the same DNA construct.

In an embodiment, the cell, preferably a plant cell, further comprises at least one, at least two, at least three, at least four or at least five additional, different exogenous polynucleotides each independently encoding different dsRNA molecules which comprise different nucleotide sequences which are complementary to a region of different target RNAs encoded by different polynucleotides of interest, and/or different nucleotide sequences which are complementary to different regions of the same target RNA, preferably where the additional polynucleotides form part of the same DNA construct.

In an embodiment, the first exogenous polynucleotide encodes more than one miRNA, preferably at least three, at least four or at least five miRNAs, each of which independently comprise different nucleotide sequences which are complementary to a region of different target RNAs encoded by different polynucleotides of interest, and/or different nucleotide sequences which are complementary to different regions of the same target RNA. The multiple miRNAs are preferably transcribed from the first exogenous polynucleotide as a single miRNA precursor transcript which is subsequently processed into the different miRNAs by the cellular machinery such as a Dicer.

Examples of a eukaryotic cell of the invention include, but are not limited to, a plant cell, a fungal cell such as a yeast cell, an invertebrate animal cell, or a vertebrate animal cell. The vertebrate animal cell may be a mammalian cell such as a human cell or a non-human mammalian cell. The cell may be in vitro such as in cell culture, or ex vivo or in vivo. The cell may be comprised in a tissue, organ or organism.

In an embodiment, when the cell is a plant cell it is preferably a cell in a plant or in a plant part such as a seed, leaf or stem. The cell may be of an angiosperm plant, a monocotyledonous plant or a dicotyledonous plant.

In an embodiment, one or more or all of the exogenous polynucleotides are not integrated into the genome of the cell, i.e. are separate from the genome. In this embodiment, the exogenous polynucleotides may be expressed transiently. The exogenous polynucleotides may lack structures or sequences required for integration or for replication in the cell.

In an embodiment, the exogenous polynucleotides are operably linked to different promoters. In an alternate embodiment, the exogenous polynucleotides are each operably linked to the same promoter i.e. the same promoter sequence is used to express each exogenous polynucleotide. In yet a further embodiment, the cell comprises at least three exogenous polynucleotides where at least two of the promoters are the same and at least one is different.

In a particularly preferred embodiment, when stably integrated into the genome the promoter operably linked to the second exogenous polynucleotide encoding a silencing suppressor polypeptide is not a constitutive promoter. For example, it is preferred the promoter is a tissue specific and/or stage-specific promoter such as a seed-specific promoter, endosperm-specific promoter, or plant embryo-specific promoter, or alternatively an inducible promotor. In this embodiment, the promoter is preferentially expressed in the desired tissue or organ relative to other tissues or organs in the organism.

The cells of the invention can be used to modify a wide range of phenotypes of the cell. For example, wherein expression of the first and second exogenous polynucleotides results in modification of fatty acid or carbohydrate synthesis such as starch synthesis in the cell, or of another metabolite in the cell. As another example, expression of the first, second and third exogenous polynucleotides results in modification of fatty acid or carbohydrate synthesis such as starch synthesis in the cell. In another example, the third exogenous polynucleotide encodes an antibody or an antigen, preferably where expression of the dsRNA molecule results in a reduction in the level and/or modifies the composition of carbohydrates bound to the antibody or antigen. This may be achieved by the dsRNA molecule by reducing the expression of genes in the cell which encode glycosyl-, fucosyl- or xylosyl-transferases which modify the composition of the carbohydrates.

In another aspect, the present invention provides a plant or a plant part comprising, i) a first exogenous polynucleotide encoding a double stranded RNA (dsRNA) molecule which comprises a first nucleotide sequence which is complementary to a region of a target RNA encoded by a first polynucleotide of interest, and ii) a second exogenous polynucleotide encoding a silencing suppressor polypeptide, wherein each exogenous polynucleotide is operably linked to one or more promoters that are capable of directing expression of the polynucleotide in a plant cell, and wherein the plant or plant part comprises the silencing suppressor polypeptide and the dsRNA molecule or a processed RNA product thereof which comprises the first nucleotide sequence and is capable of reducing in the cell the level of the target RNA encoded by the first polynucleotide of interest and/or the amount of a protein encoded by the target RNA when compared to a corresponding cell lacking the first exogenous polynucleotide. The plant may be angiosperm, a monocotyledonous plant or a dicotyledonous plant, or a part thereof. The plant part, preferably a seed, may be modified so that it cannot germinate or give rise to progeny plants. For example, the plant part may be processed by polishing, milling, grinding or the like.

In an embodiment, the plant or plant part is further characterised by one or more of the above features.

In a further aspect, the present invention provides a process for producing a eukaryotic cell, preferably a plant cell, of the invention, the method comprising a) introducing one or more of the exogenous polynucleotides into a eukaryotic cell such that the cell comprises the exogenous polynucleotides, and b) expressing the exogenous polynucleotides in the cell.

The cell into which the one or more of the exogenous polynucleotides are introduced may already have comprised an exogenous polynucleotide other than the one or more exogenous polynucleotides, or it may have been non-transgenic prior to the introduction. This process may be used as a screening assay to determine whether one or more of the exogenous polynucleotides have a desired function, or whether the combination of exogenous polynucleotides together produces a desired phenotype.

In an embodiment, the cell comprises at least the first, second and third exogenous polynucleotides and the process further comprises one or more steps selected from:

c) analysing the cell for the presence of one or more of the first, second and third exogenous polynucleotides, the first polynucleotide of interest or the RNA of interest, and d) analysing the cell for a reduction in the level of the target RNA encoded by the first polynucleotide of interest and/or amount of the protein encoded by the target RNA, e) analysing the cell for the level of the RNA of interest and/or the amount of protein encoded by the RNA of interest, if present, and f) selecting a cell which has an increased level of the RNA of interest and/or an increased amount of protein encoded by the RNA of interest when compared to a corresponding cell having the third exogenous polynucleotide and lacking the second exogenous polynucleotide, and/or which has a reduced level of the target RNA encoded by the first polynucleotide of interest and/or a reduced amount of the protein encoded by the target RNA when compared to a corresponding cell lacking the first exogenous polynucleotide.

In an embodiment, step a) comprises introducing into the cell two or three exogenous polynucleotides.

In an embodiment, the selected cell is further characterised by one or more of the above features.

In an embodiment, the cell is a plant cell and the process further comprises the step of regenerating a transformed plant from a cell comprising the exogenous polynucleotides. The process may further comprise harvesting a plant part, preferably one or more of seed, leaves, stems or tubers, from the transformed plant, and/or obtaining progeny plants from the transformed plant. The analysing steps as outlined above may be carried out on the harvested plant part or the progeny plant.

In an embodiment, the exogenous polynucleotide(s) are expressed transiently in the cell.

In an embodiment, the cell is a leaf cell in a plant or a cell in a seed.

Also provided is a process for selecting a eukaryotic cell, preferably a plant cell, with a desired property resulting from an increased level of an RNA of interest and/or amount of protein encoded by the RNA of interest, and a reduced level of target RNA encoded by a first polynucleotide of interest and/or amount of the protein encoded by the target RNA, the process comprising;

i) obtaining one or more cells of the invention comprising the third exogenous polynucleotide, ii) analysing the cell(s) for the desired property, iii) if the cell(s) does not have the desired property, substituting one or more of the exogenous polynucleotides with an alternate polynucleotide(s) and analysing the resultant cell(s) for the desired property, iv) if necessary, repeating step iii) until the desired property is obtained, and v) selecting a cell with the desired property.

The cell(s) may be in a tissue, organ or organism, for example in a transgenic plant, such that the analysis of step ii) is carried out at the level of the tissue, organ or organism. The desired property may be any phenotype of the cell, tissue, organ or organism.

In an embodiment, the first exogenous polynucleotide is substituted such that a dsRNA molecule encoded thereby comprises more or less of a nucleotide sequence which is closer to the 3' end of the target RNA when compared to the exogenous polynucleotide used in the previous step.

In an embodiment, the second exogenous polynucleotide is substituted with a different exogenous polynucleotide which encodes a different silencing suppressor or candidate silencing suppressor. In this embodiment, candidate silencing suppressors may be evaluated for their ability to suppress silencing and thereby increase expression of the third exogenous polynucleotide, or candidate silencing suppressors may be compared.

In a further aspect, the present invention provides a process for selecting a eukaryotic cell, preferably a plant cell, with a desired property resulting from an increased level of an RNA of interest and/or amount of protein encoded by the RNA of interest, and a reduced level of target RNA encoded by a first polynucleotide of interest and/or amount of the protein encoded by the target RNA, the process comprising;

i) obtaining a population of cells, preferably each in a tissue, organ or organism such as a transgenic plant, comprising the third exogenous polynucleotide, and wherein at least some of the cells have different combinations of different first, second or third exogenous polynucleotides, ii) screening the cell(s) for the desired property, and iii) selecting one or more cells with the desired property.

In yet another aspect, the present invention provides a process for selecting a eukaryotic cell, preferably a plant cell, with a desired level of silencing of a polynucleotide of interest, the process comprising;

i) obtaining one or more cells, preferably each in a tissue, organ or organism such as a transgenic plant, each comprising a first exogenous polynucleotide encoding a double stranded RNA (dsRNA) molecule which comprises a first nucleotide sequence which is complementary to a region of a target RNA encoded by the polynucleotide of interest, and a second exogenous polynucleotide encoding a silencing suppressor polypeptide, ii) analysing the cell(s) for one or more of (a) the level of the target RNA encoded by the polynucleotide of interest, (b) the amount of the protein encoded by the target RNA, (c) the level of the dsRNA molecule or a processed RNA product thereof which comprises the first nucleotide sequence and which is capable of reducing in the cell the level of the target RNA encoded by the first polynucleotide of interest and/or the amount of a protein encoded by the target RNA when compared to a corresponding cell lacking the first exogenous polynucleotide, and (d) for a phenotype that is determined by the polynucleotide of interest, iii) if the cell(s) does not have the desired level of silencing of the polynucleotide of interest, substituting one or both of the exogenous polynucleotides with an alternate polynucleotide(s) and analysing the resultant cell(s) for the desired level of silencing, iv) if necessary, repeating step iii) until the desired level of silencing of the polynucleotide of interest is obtained, and v) selecting a cell with the desired level of silencing, wherein each exogenous polynucleotide is operably linked to one or more promoters that are capable of directing expression of the polynucleotides in the cell. The one or more cells may be analysed at the same time, in batches, or sequentially. The desired level of silencing of the polynucleotide of interest may be assessed by analysing the cell for a desired property expected as a result of the silencing.

In another aspect, the present invention provides a process for selecting a silencing suppressor which is compatible with a double-stranded RNA (dsRNA) molecule of interest, comprising the steps of i) obtaining one or more eukaryotic cells, preferably plants cells, and preferably each in a tissue, organ or organism such as a transgenic plant, each of which comprises (a) a first exogenous polynucleotide encoding the dsRNA molecule which comprises a first nucleotide sequence which is complementary to a region of a target RNA encoded by a first polynucleotide of interest, and (b) a second exogenous polynucleotide encoding a candidate silencing suppressor polypeptide which may be compatible with the dsRNA molecule, wherein each exogenous polynucleotide is operably linked to one or more promoters that are capable of directing expression of the polynucleotide in the cell, ii) analysing the cell(s) for one or more of (a) the level of the target RNA encoded by the polynucleotide of interest, (b) the amount of the protein encoded by the target RNA, (c) the level of the dsRNA molecule or a processed RNA product thereof which comprises the first nucleotide sequence and which is capable of reducing in the cell the level of the target RNA encoded by the first polynucleotide of interest and/or the amount of a protein encoded by the target RNA when compared to a corresponding cell lacking the first exogenous polynucleotide, and (d) for a phenotype that is determined by the polynucleotide of interest, iii) if the cell(s) does not have a desired property, substituting the second exogenous polynucleotide in the cell with an alternate polynucleotide(s) which encodes a candidate compatible silencing suppressor and repeating step ii), and iv) if necessary, repeating step iii) until a cell(s) with the desired property is identified, thereby selecting the silencing suppressor which is compatible with the dsRNA molecule. This process thereby provides a screening assay to determine whether the silencing suppressor and dsRNA molecule can both function in the same cell, i.e are compatible, and allows multiple combinations thereof to be tested or compared.

In a preferred embodiment, the cell(s) further comprises a third exogenous polynucleotide, different to the first and second exogenous polynucleotides and the first polynucleotide of interest, and the process further comprises the step of analysing the cell(s) for one or more of the level of expression of the third exogenous polynucleotide or a phenotype of the cell(s) determined by the third exogenous polynucleotide.

In a more preferred embodiment, the level of expression of the third exogenous polynucleotide is increased in the presence of the selected silencing suppressor when compared to a corresponding cell having the third exogenous polynucleotide and lacking the second exogenous polynucleotide.

In another aspect, the present invention provides a DNA construct comprising, i) a first polynucleotide encoding a double stranded RNA (dsRNA) molecule which comprises a first nucleotide sequence which is complementary to a region of a target RNA encoded by a first polynucleotide of interest, and ii) a second polynucleotide encoding a silencing suppressor, wherein each polynucleotide is operably linked to one or more promoters that are capable of directing expression of the polynucleotides in a cell, preferably a plant cell, and the first and second polynucleotides are exogenous to the cell.

In an embodiment, the DNA construct further comprises a third polynucleotide, different to the first or second polynucleotides or first polynucleotide of interest, such that expression of the third polynucleotide in a eukaryotic cell comprising the DNA construct is increased when compared to a corresponding cell having the third polynucleotide and lacking the second polynucleotide.

In another aspect, the present invention provides a vector comprising the DNA construct of the invention.

In a further aspect, the present invention provides a cell comprising the DNA construct of the invention and/or the vector of the invention.

Also provided is a cell produced or selected using the process of the invention.

In another aspect, provided is a transgenic non-human eukaryotic organism comprising a cell of the invention.

In an embodiment, the transgenic non-human eukaryotic organism is a plant.

In a further aspect, the present invention provides a part of a transgenic non-human eukaryotic organism of the invention comprising a cell of the invention.

In an embodiment, the part is a seed, leaf, stem, flower, root or tuber.

The cells, or transgenic non-human organisms comprising the cell or a part thereof, of the invention can be used for a wide variety of purposes depending on the cells, the dsRNA and the RNA of interest. Thus, in a further aspect the present invention provides a method of making a product, the method comprising one or more of obtaining, growing, cultivating or culturing a cell of the invention, a transgenic non-human organism comprising the cell or a part thereof, and optionally processing the cell, organism or part to produce the product.

In an embodiment, the product is one or more of a feedstuff, an oil, a fatty acid, a medicament, fuel or an industrial product. The invention further provides for uses of the polynucleotides or cells of the invention to produce such products.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1: V2 allows overexpression of transgenes and their efficient silencing via hairpin RNAi. A, Time course of GFP expression with either no co-infiltrated VSP or the addition of V2 or p19. Image shows one representative leaf photographed up to 7 days post infiltration (dpi), and the image at 7 dpi is used to illustrate the labelling of each infiltration zone. B, Time course of the effect of V2 or p19 on hairpin-based silencing of GFP. The image shows one representative leaf photographed at 5 dpi.

Figure 2:
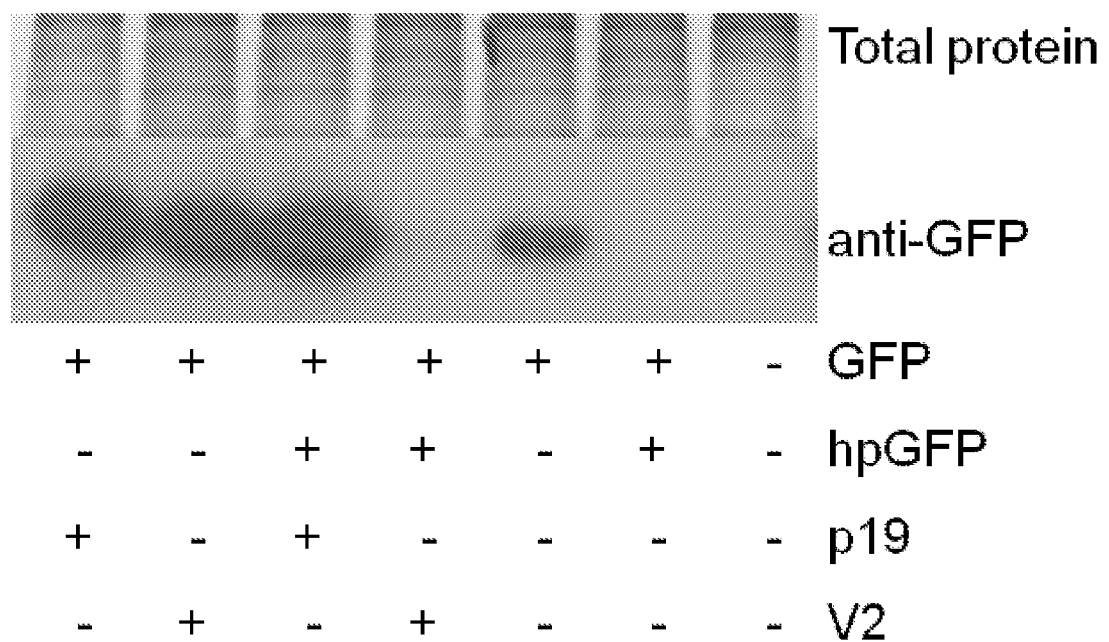

FIG. 2: Western blot analysis of GFP expression in leaves sampled at 4 dpi. Image shows one experiment from a duplicate conducted on different leaves.

Figure 3:
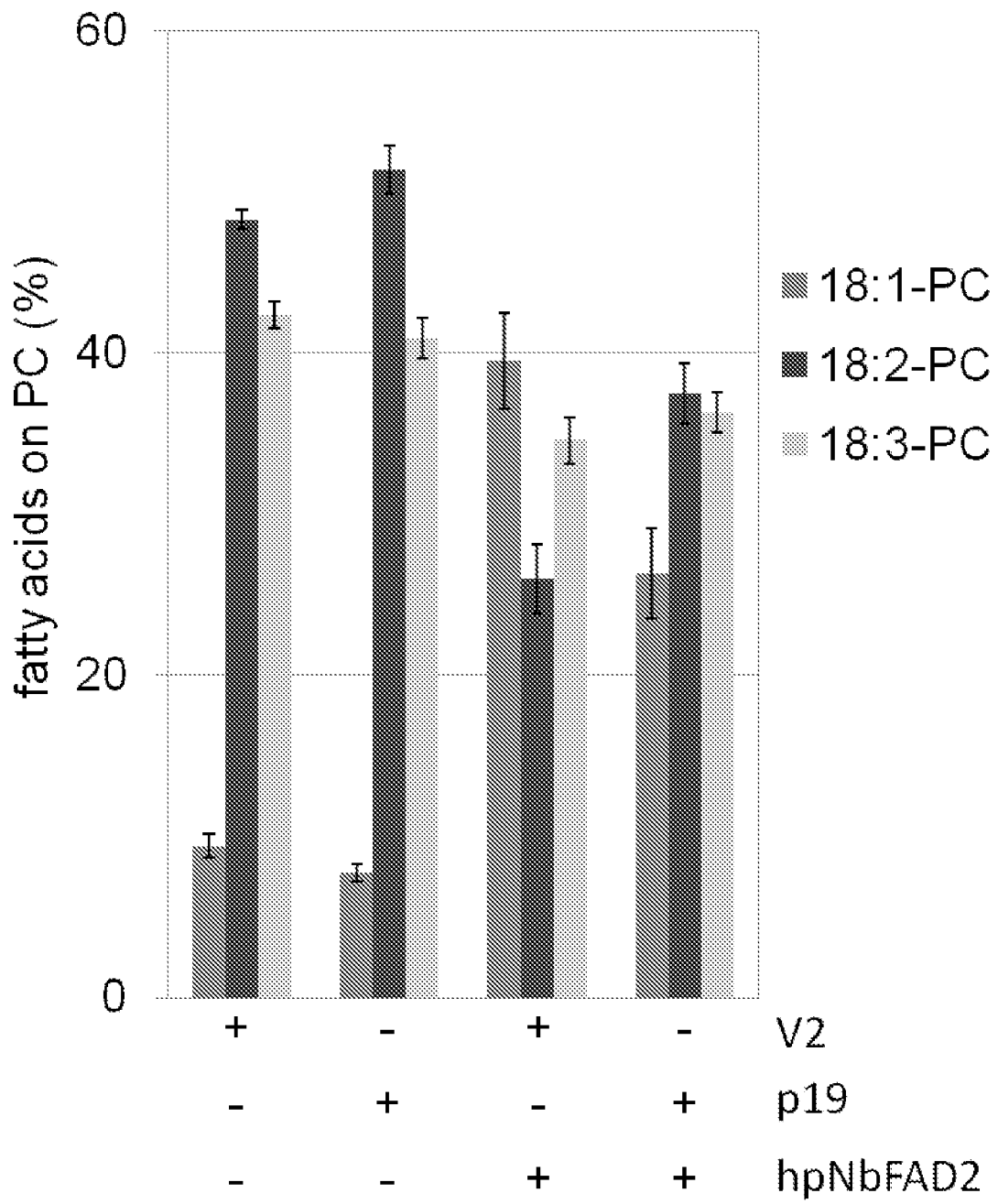

FIG. 3: Analysis of the composition of the phosphatidylcholine (PC) fraction of leaves infiltrated with various combinations of V2, p19 and hpNbFAD2. Leaves were sampled 5 dpi and the error bars represent the standard error of the mean from 5 independent leaves.

Figure 4:
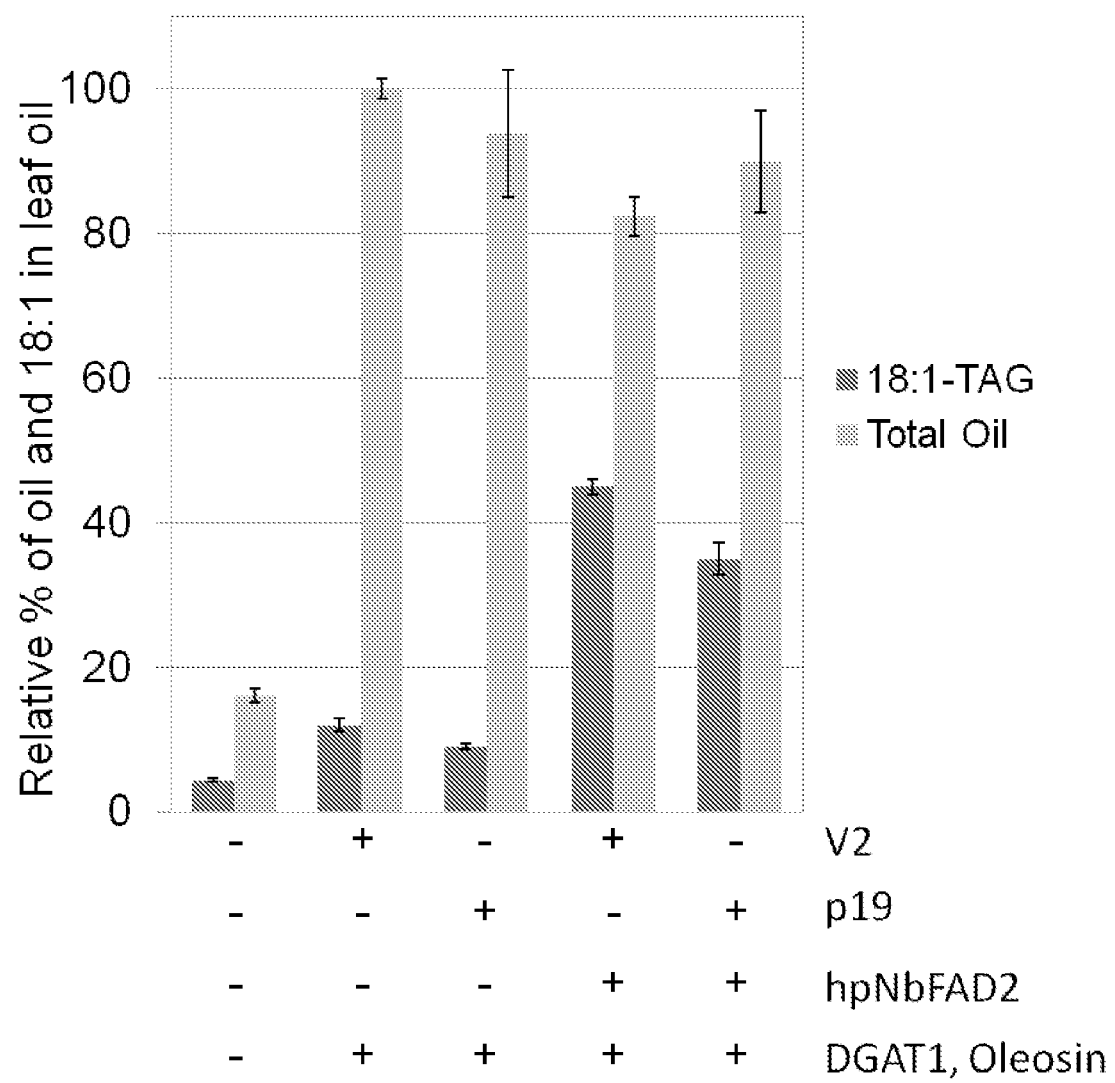

FIG. 4: Analysis of the content and composition of leaf oils when leaves were infiltrated with combinations of V2, p19, hpNbFAD2, DGAT1 and oleosin. Leaves were samples 5 dpi and error bars represent the standard error of the mean calculated from 5 independent leaves.

Figure 5:
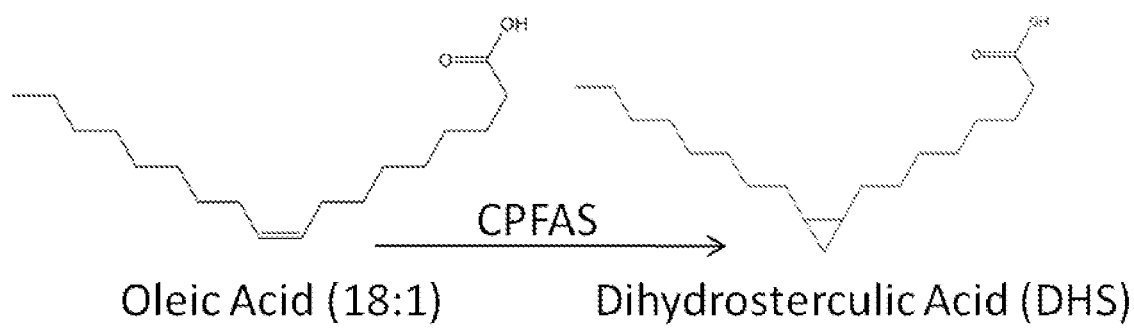

FIG. 5: The enzymatic production of DHS from oleic acid.

Figure 6:
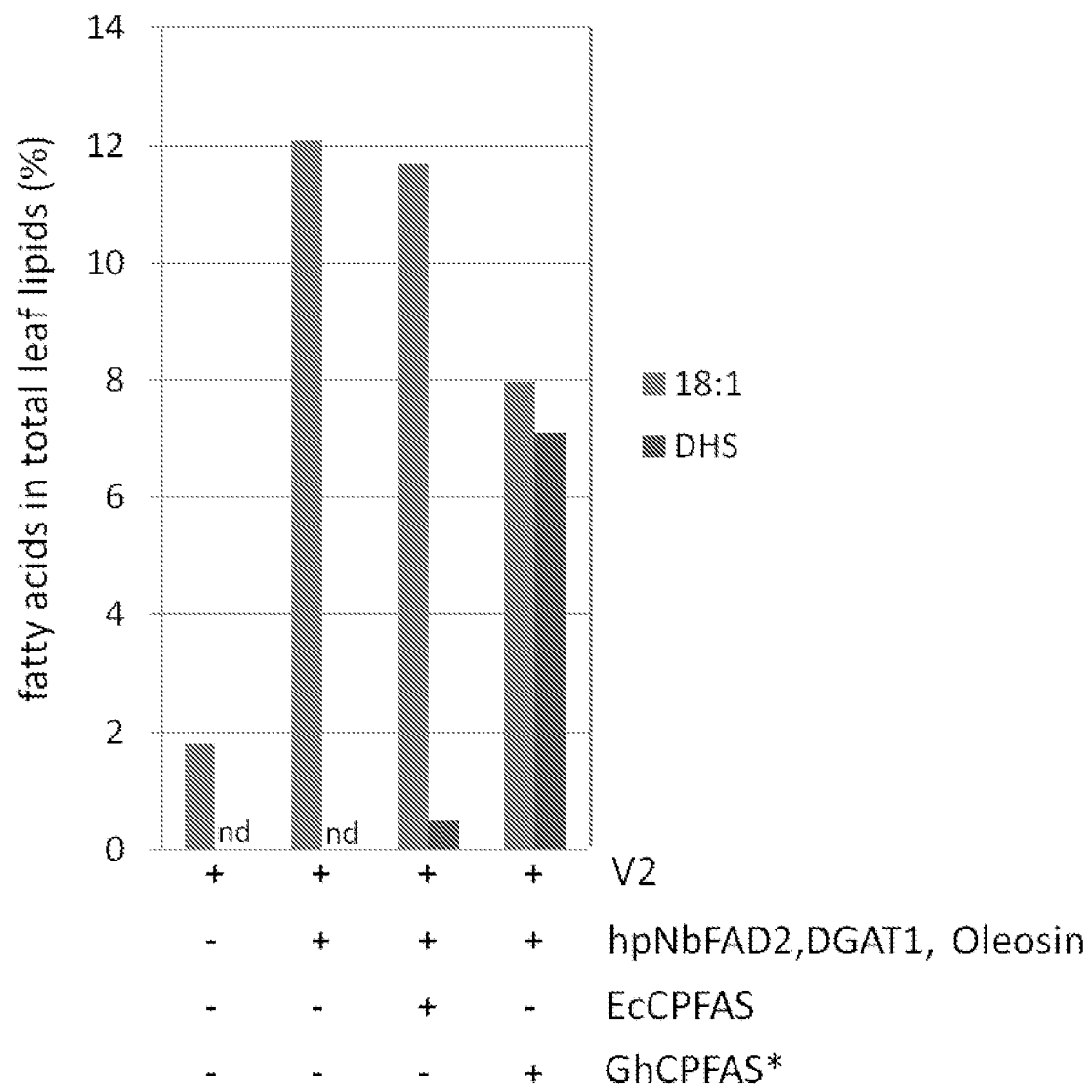

FIG. 6: Comparison of the production of DHS in leaf assays using either EcCPFAS or GhCPFAS in transient leaf assays. Leaves were harvested 4 dpi.

Figure 7:
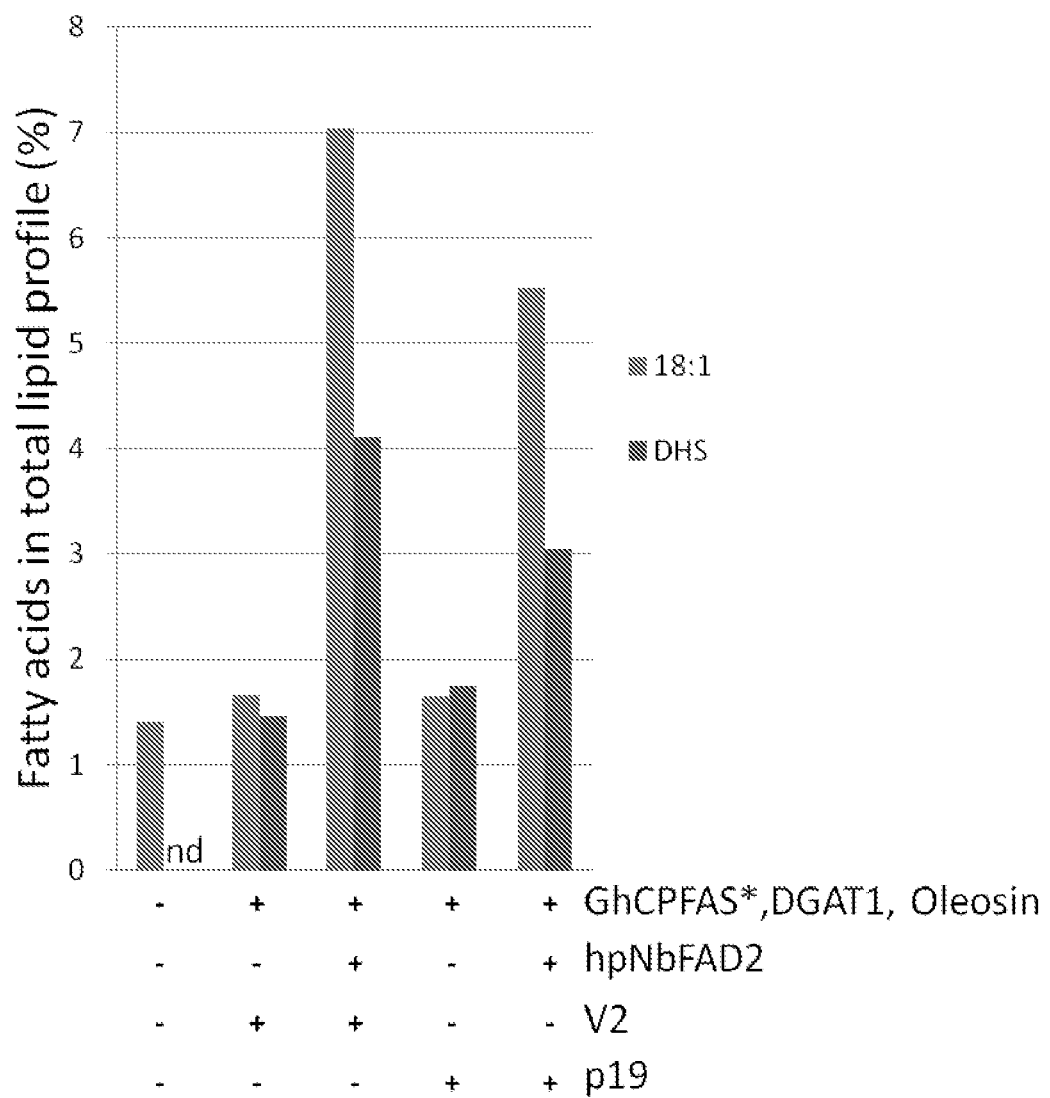

FIG. 7: Overexpression of transgenes and silencing of an endogene for improved fluxes of DHS into leaf oils. Leaves were harvested 4 dpi. These comparisons were conducted on 4 different leaves, and this figure shows results from one representative leaf.

Figure 8:
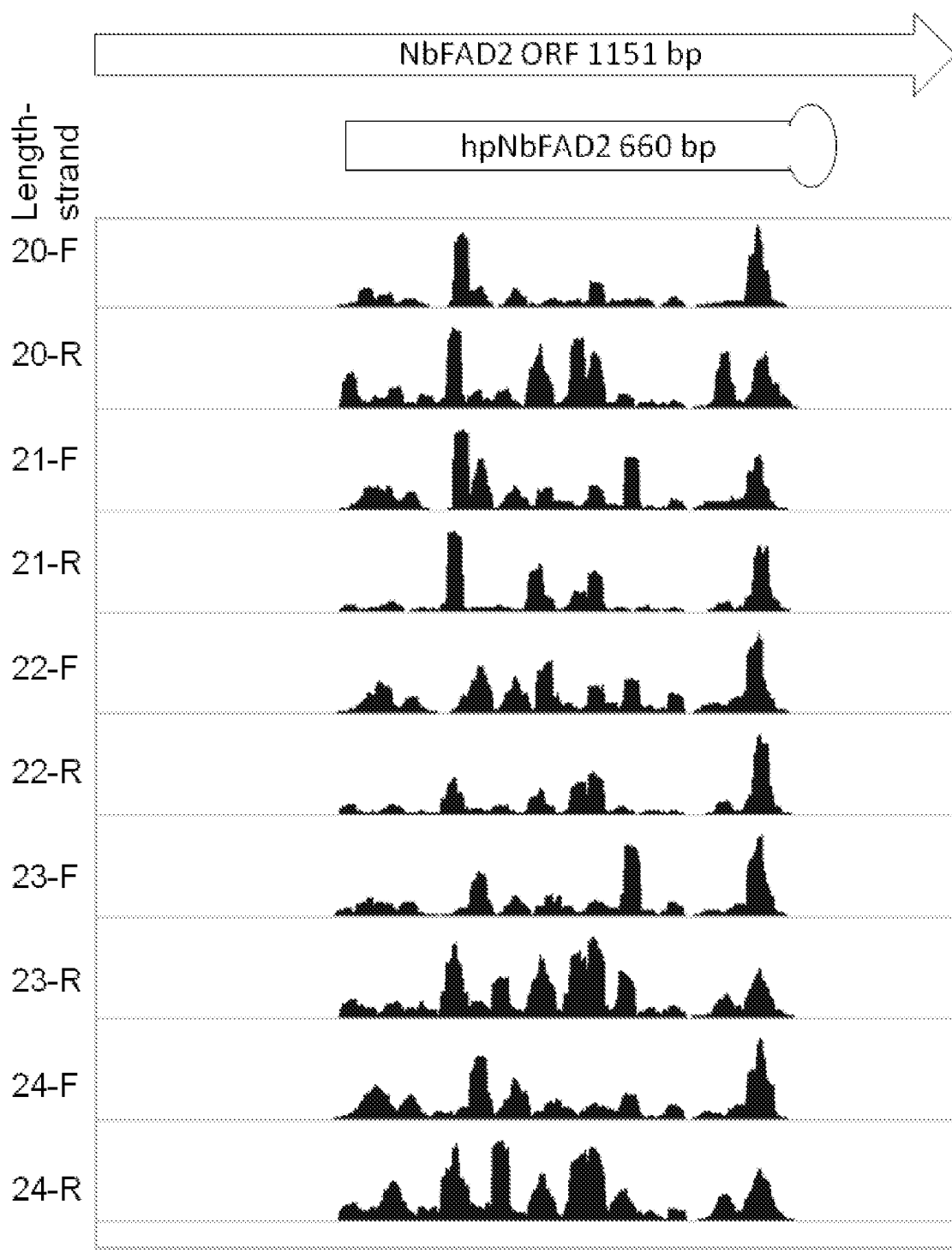

FIG. 8: 'Deep sequencing' analysis of the size and distribution of small RNA populations generated by a hairpin targeting the endogene NbFAD2. The full-length NbFAD2 is portrayed indicating the region used to generate a 660 bp hairpin, hpNbFAD2. The size and distribution of the dominate classes of small RNAs on the forward (F) and reverse (R) strand of the NbFAD2 is illustrated below. Each track is rescaled to show the relatively uneven distribution of small RNAs across the target.

Figure 9:
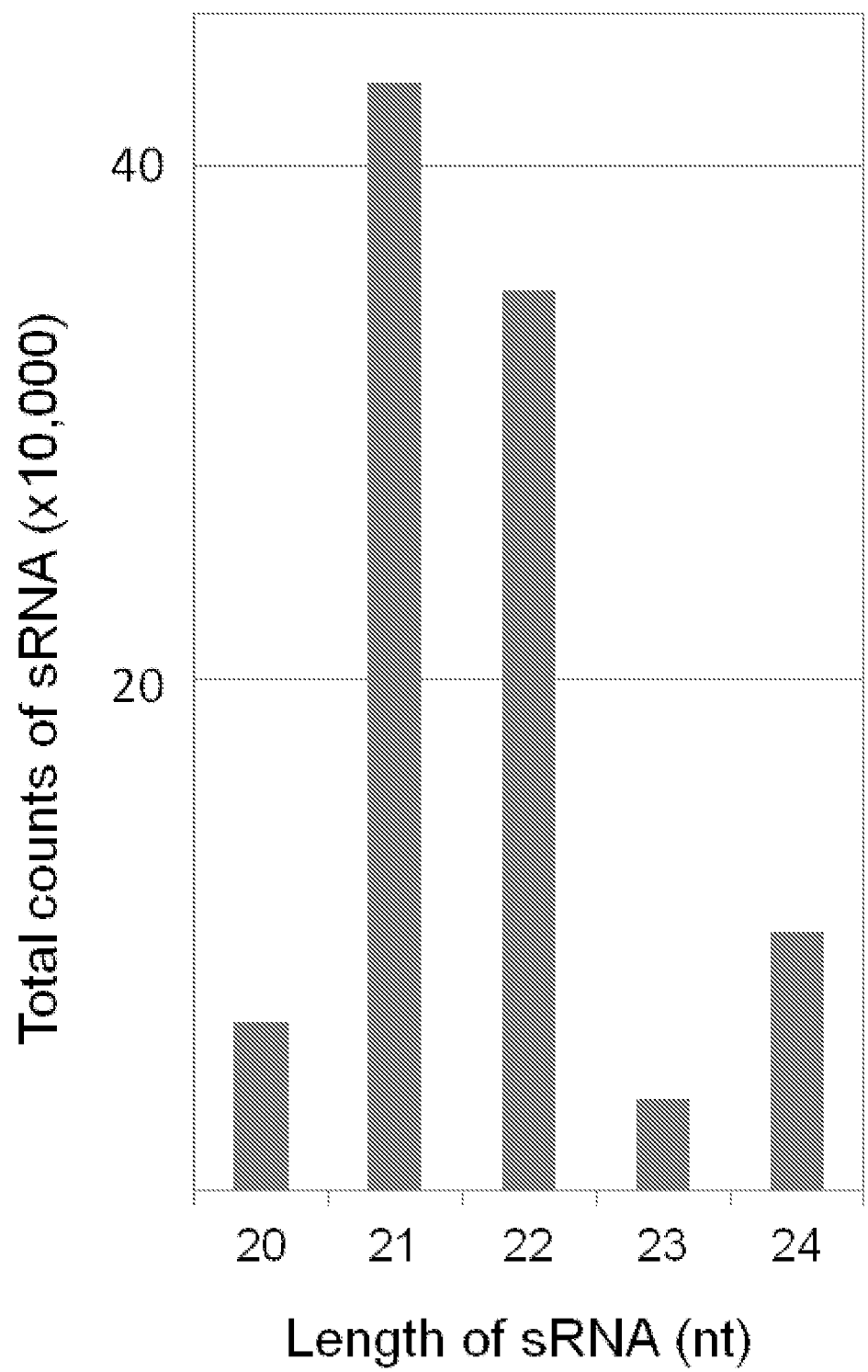

FIG. 9: Absolute numbers of the dominant small RNA size classes generated by hpNbFAD2. The relative percentage of each size class is given in the text.

Figure 10:
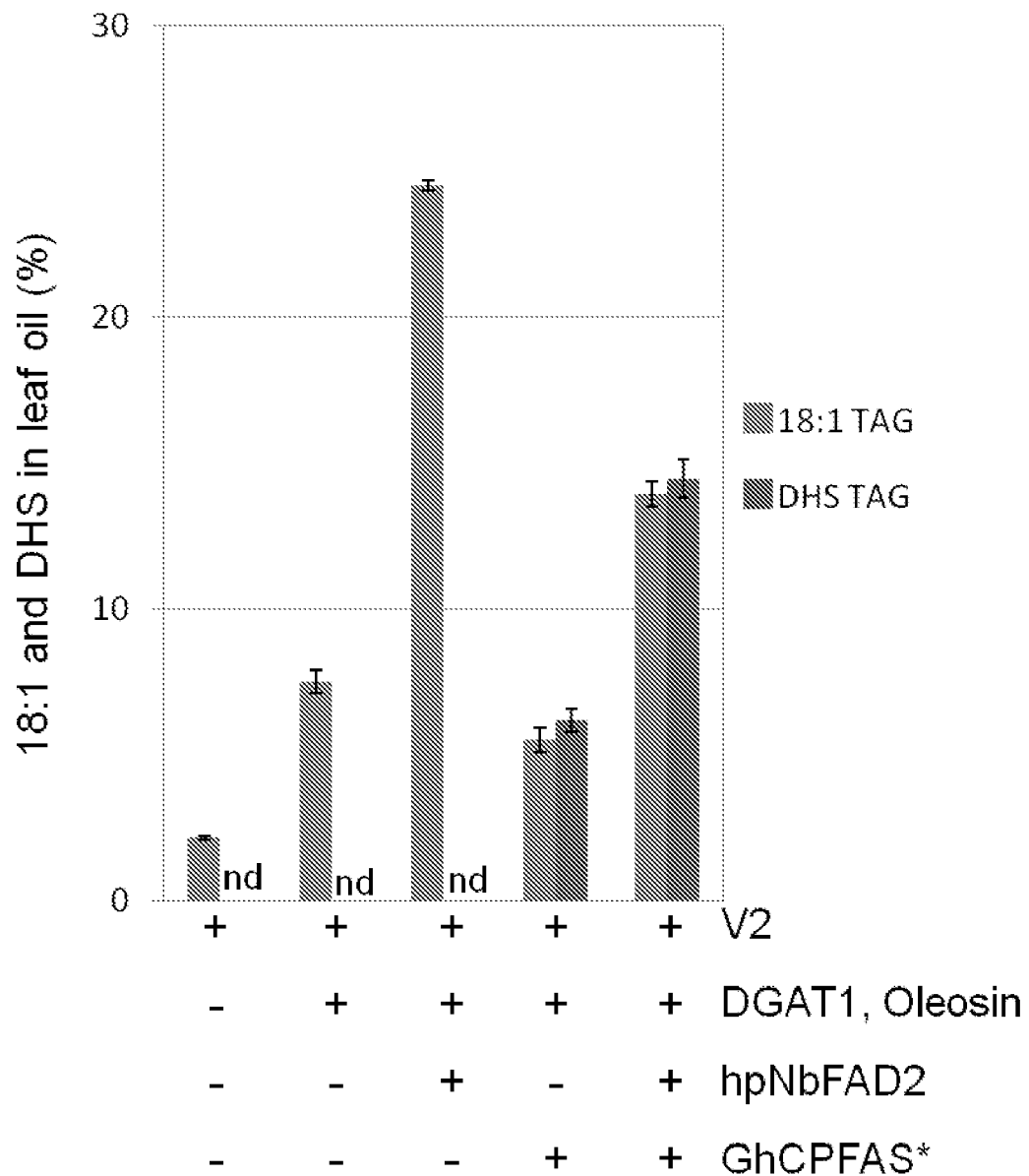

FIG. 10: DHS is accumulated in leaf oils.

Figure 11:
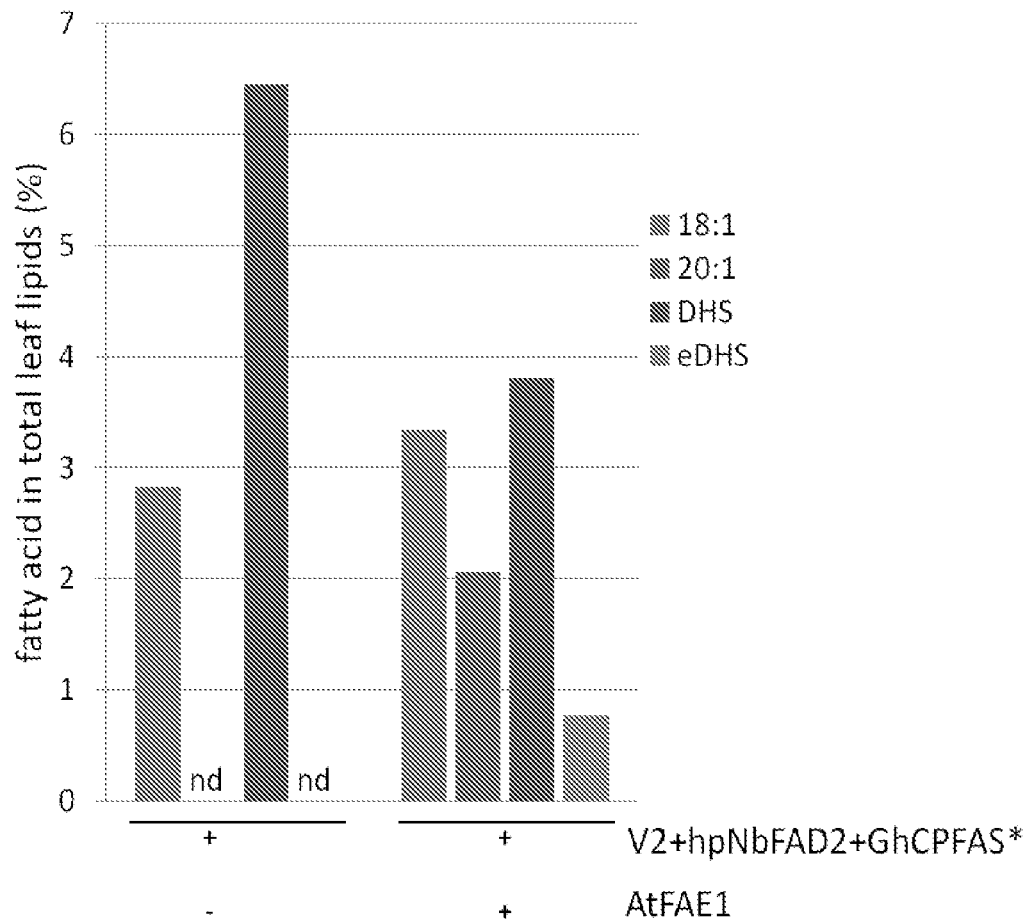

FIG. 11: Fatty acid profile of leaves producing DHS in the presence or absence of the elongase AtFAE1. Elongation experiments were conducted on 3 different leaves, and the figure shows a representative fatty acid profile from a single leaf.

Figure 12:
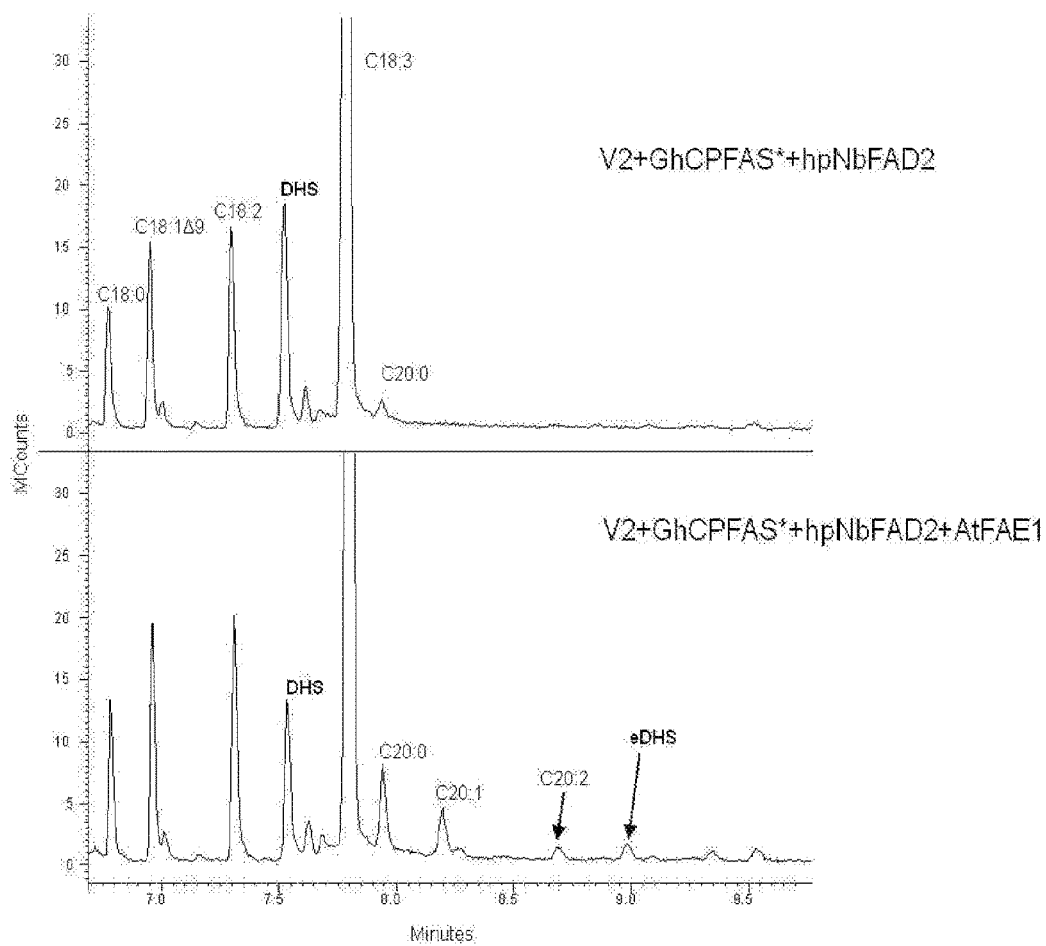
Figure 12:
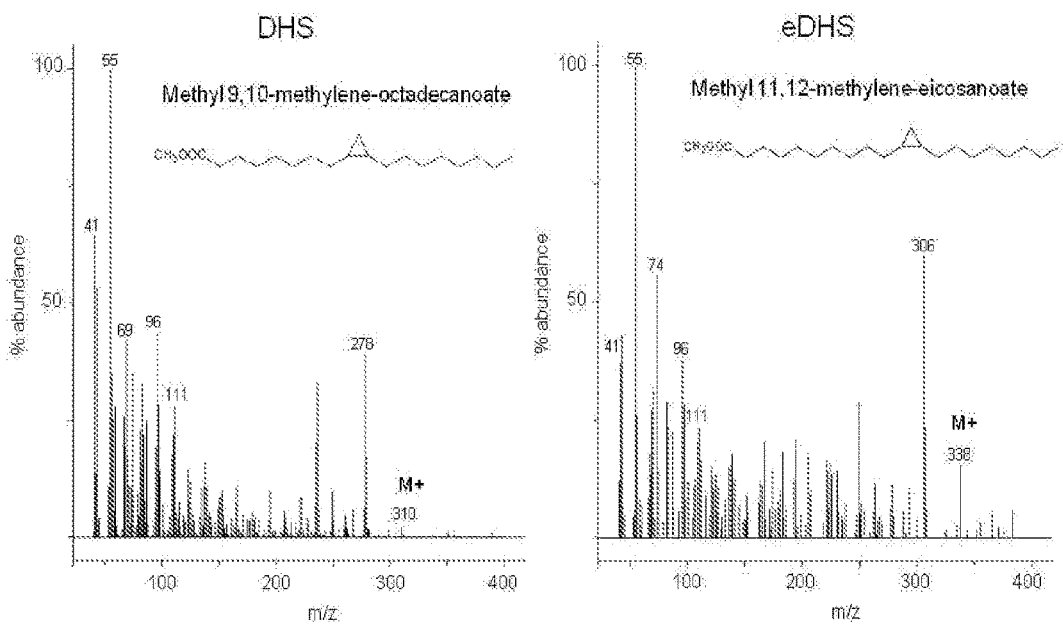

FIG. 12: The identification of eDHS using a range of GC and MS techniques. The upper panels show GC (FID) traces for lipid extracts from leaves infiltrated with the combination of genes as shown. Common and new metabolites are shown as indicated. Lower panels show the range of masses for metabolites first resolved on the GC, DHS and eDHS. The inserts for each MS indicates the structure of DHS and eDHS.

KEY TO THE SEQUENCE LISTING

SEQ ID NO: 1—amino acid sequence of tomato leaf yellow curl virus V2 protein

SEQ ID NO: 2—amino acid sequence of tomato bushy stunt virus P19 protein

SEQ ID NO: 3—nucleotide sequence encoding tomato leaf yellow curl virus V2 protein SEQ ID NO: 4—nucleotide sequence encoding tomato bushy stunt virus P19 protein SEQ ID NO: 5—amino acid sequence of *Sesmum indicum* oleosin protein SEQ ID NO: 6—nucleotide sequence encoding *Sesmum indicum* oleosin protein SEQ ID NO: 7—amino acid sequence of *Arabidopsis thaliana* AtFAE1 protein SEQ ID NO: 8—nucleotide acid sequence encoding *Arabidopsis thaliana* AtFAE1 protein including 5' intron sequence SEQ ID NO: 9—amino acid sequence of *Arabidopsis thaliana* AtDGAT1 protein SEQ ID NO: 10—nucleotide acid sequence encoding *Arabidopsis thaliana* AtDGAT1 protein
SEQ ID NO: 11—amino acid sequence of NbFAD2 protein
SEQ ID NO: 12—nucleotide sequence encoding dsRNA hairpin targeting *N. benthamiana* FAD2
SEQ ID NOs 13 to 20—oligonucleotide primers
SEQ ID NO: 21—amino acid sequence of *Gossypium hirsutum* CPFAS-1 (truncated protein)
SEQ ID NO: 22—amino acid sequence of *Gossypium hirsutum* CPFAS-1
SEQ ID NO: 23—nucleotide sequence encoding truncated *Gossypium hirsutum* CPFAS-1
SEQ ID NO: 23—nucleotide sequence encoding *Gossypium hirsutum* CPFAS-1
SEQ ID NO: 24—amino acid sequence of *Escherichia coli* CPFAS
SEQ ID NO: 26—codon optimized *E. Coli* CPFAS open reading frame for plant expression
SEQ ID NO: 27—Cymbiduium ringspot tombus virus p19 like silencing suppressor
SEQ ID NO: 28—Pelargonium necrotic spot virus p19 like silencing suppressor
SEQ ID NO: 29—Havel river tombus virus p19 like silencing suppressor
SEQ ID NO: 30—Cucumber necrosis virus p19 like silencing suppressor
SEQ ID NO: 31—Grapevine Algerian latent virus p19 like silencing suppressor
SEQ ID NO: 32—Pear latent virus p19 like silencing suppressor
SEQ ID NO: 33—Lisianthus necrotic virus p19 like silencing suppressor
SEQ ID NO: 34—Lettuce necrotic stunt virus p19 like silencing suppressor
SEQ ID NO: 35—Artichoke Mottled Crinkle virus p19 like silencing suppressor
SEQ ID NO: 36—Carnation Italian ringspot virus p19 like silencing suppressor
SEQ ID NO: 37—Maize necrotic steak virus p19 like silencing suppressor
SEQ ID NO: 38—Watermelon chlorotic stunt virus V2 like silencing suppressor
SEQ ID NO: 39—Okra yellow wrinkle virus V2 like silencing suppressor
SEQ ID NO: 40—Okra leaf curl virus V2 like silencing suppressor
SEQ ID NO: 41—Tomato leaf curl togo virus V2 like silencing suppressor
SEQ ID NO: 42—Ageratum leaf curl Cameroon virus V2 like silencing suppressor
SEQ ID NO: 43—East African cassava mosaic Malawi virus V2 like silencing suppressor
SEQ ID NO: 44—South African cassava mosaic virus V2 like silencing suppressor
SEQ ID NO: 45—Tomato leaf curl Madagascar virus V2 like silencing suppressor
SEQ ID NO: 46—Tomato leaf curl Zimbabwe virus V2 like silencing suppressor
SEQ ID NO: 47—Tomato begomovirus V2 like silencing suppressor
SEQ ID NO: 48—Tomato leaf curl Namakely virus V2 like silencing suppressor
SEQ ID NO: 49—Pepper yellow vein Mali virus V2 like silencing suppressor
SEQ ID NO: 50—Tomato leaf curl Sudan virus V2 like silencing suppressor
SEQ ID NO: 51—Tomato leaf curl Oman virus V2 like silencing suppressor
SEQ ID NO: 52—nucleotide sequence encoding miRNA targeting *A. thaliana* pytoene desaturase
SEQ ID NO: 53—nucleotide sequence encoding miRNA targeting *A. thaliana* FAD2

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

As used herein, the term "about", unless stated to the contrary, refers to +/−20%, more preferably +/−10%, more preferably +/−5%, more preferably +/−2%, more preferably +/−1%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The term "exogenous" in the context of a polynucleotide or polypeptide refers to the polynucleotide or polypeptide when present in a cell that does not naturally comprise the polynucleotide or polypeptide. In an embodiment, the exogenous polynucleotide or polypeptide is from a different genus. In another embodiment, the exogenous polynucleotide or polypeptide is from a different species. In one embodiment the exogenous polynucleotide or polypeptide is expressed in a host organism or cell and the exogenous polynucleotide or polypeptide is from a different species or genus.

The term "corresponding" refers to a cell, or non-human eukaryotic organism or part thereof that has the same or similar genetic background as a cell, or non-human eukaryotic organism or part thereof of the invention but that has not been modified as described herein. For example, the cell, or non-human eukaryotic organism or part thereof lacks the first exogenous polynucleotide encoding the dsRNA, and/or which lacks the second exogenous polynucleotide encoding the silencing suppressor polypeptide. A corresponding cell or non-human eukaryotic organism or part thereof can be used as a control to compare levels/amount of, for example, RNA and/or protein, or the extent and nature of trait modification, for example non-polar lipid or starch production and/or content, with a cell, or non-human eukaryotic organism or part thereof modified as described herein. A person skilled in the art is able to readily determine an appropriate "corresponding" cell, tissue, organ or organism for such a comparison.

As used herein "compared to", "relative to" or variations thereof refers to comparing, for example, the levels/amount of RNA and/or protein of the transgenic cell, or non-human eukaryotic organism or part thereof, expressing the one or more exogenous polynucleotides with a cell, or non-human eukaryotic organism or part thereof lacking the one or more exogenous polynucleotides.

The term "transgenic non-human eukaryotic organism" refers to, for example, a whole plant, algae, non-human animal, or an organism suitable for fermentation such as a yeast or fungus, comprising an exogenous polynucleotide (transgene). In one embodiment, the transgenic non-human organism is a phototrophic organism (for example, a plant or alga) capable of obtaining energy from sunlight to synthesize organic compounds for nutrition.

As used herein, a "desired property" refers to a phenotype which is not possessed by the cell but which is desired. The property may be an increase or decrease (or abolished) in the level of an existing phenotype or a phenotype not possessed by the cell without the exogenous polynucleotides.

Silencing Suppressors

Post-transcriptional gene silencing (PTGS) is a nucleotide sequence-specific defense mechanism that can target both cellular and viral mRNAs for degradation. PTGS occurs in eukaryotic cells such as plants or fungi stably or transiently transformed with a recombinant polynucleotide(s) and results in the reduced accumulation of RNA molecules with sequence similarity to the introduced polynucleotide. "Post-transcriptional" refers to a mechanism for the reduction operating at least partly, but not necessarily exclusively, after production of an initial RNA transcript, for example during processing of the initial RNA transcript, or concomitant with splicing or export of the RNA to the cytoplasm, or within the cytoplasm by complexes associated with Argonaute proteins.

RNA molecule levels can be increased, and/or RNA molecule levels stabilized over numerous generations or under different environmental conditions, by limiting the expression of a silencing suppressor in a storage organ of a plant or part thereof. As used herein, a "silencing suppressor" is any polypeptide that can be expressed in a eukaryotic cell that enhances the level of expression product from a different transgene in the cell, particularly, over repeated generations from the initially transformed cell.

In an embodiment, the silencing suppressor is a viral silencing suppressor or mutant thereof. A large number of viral silencing suppressors are known in the art and include, but are not limited to P19, V2 (Glick et al. 2008; Fukunaga and Doudna, 2009), P38, Pe-Po and RPV-P0. Examples of suitable viral silencing suppressors include those described in WO 2010/057246.

A silencing suppressor may be stably expressed in a transgenic non-human eukaryotic organism or part thereof of the present invention. As used herein, the term "stably expressed" or variations thereof refers to the level of the RNA molecule being essentially the same or higher in progeny cells, organisms or parts over repeated generations, for example, at least three, at least five, or at least ten generations, when compared to corresponding cells, organisms or parts lacking the exogenous polynucleotide encoding the silencing suppressor. However, this term(s) does not exclude the possibility that over repeated generations there is some loss of levels of the RNA molecule when compared to a previous generation, for example, not less than a 10% loss per generation.

The suppressor can be selected from any source e.g. plant, viral, mammal, etc. The suppressor may be, for example:
flock house virus B2,
pothos latent virus P14,
pothos latent virus AC2,
African cassava mosaic virus AC4,
bhendi yellow vein mosaic disease C2,
bhendi yellow vein mosaic disease C4,
bhendi yellow vein mosaic disease βC1,
tomato chlorosis virus p22,
tomato chlorosis virus CP,
tomato chlorosis virus CPm,
tomato golden mosaic virus AL2,
tomato leaf curl Java virus βC1,
tomato yellow leaf curl virus V2,
tomato yellow leaf curl virus-China C2,
tomato yellow leaf curl China virus Y10 isolate βC1,
tomato yellow leaf curl Israeli isolate V2,
mungbean yellow mosaic virus-Vigna AC2,
hibiscus chlorotic ringspot virus CP,
turnip crinkle virus P38,
turnip crinkle virus CP,
cauliflower mosaic virus P6,
beet yellows virus p21,
citrus tristeza virus p20,
citrus tristeza virus p23,
citrus tristeza virus CP,
cowpea mosaic virus SCP,
sweet potato chlorotic stunt virus p22,
cucumber mosaic virus 2b,
tomato aspermy virus HC-Pro,
beet curly top virus L2,
soil borne wheat mosaic virus 19K,
barley stripe mosaic virus Gammab,
poa semilatent virus Gammab,
peanut clump pecluvirus P15,
rice dwarf virus Pns10,
curubit aphid borne yellows virus P0,
beet western yellows virus P0,
potato virus X P25,
cucumber vein yellowing virus P1b,
plum pox virus HC-Pro,
sugarcane mosaic virus HC-Pro,
potato virus Y strain HC-Pro,
tobacco etch virus P1/HC-Pro,
turnip mosaic virus P1/HC-Pro,
cocksfoot mottle virus P1,
cocksfoot mottle virus-Norwegian isolate P1,
rice yellow mottle virus P1,
rice yellow mottle virus-Nigerian isolate P1,
rice hoja blanca virus NS3,
rice stripe virus NS3,
crucifer infecting tobacco mosaic virus 126K,
crucifer infecting tobacco mosaic virus p122,
tobacco mosaic virus p122,
tobacco mosaic virus 126, tobacco mosaic virus 130K,
tobacco rattle virus 16K,
tomato bushy stunt virus P19,
tomato spotted wilt virus NSs,
apple chlorotic leaf spot virus P50,
grapevine virus A p10,
grapevine leafroll associated virus-2 homolog of BYV p21,
as well as variants/mutants thereof. The list above provides the virus from which the suppressor can be obtained and the protein (e.g., B2, P14, etc.), or coding region designation for the suppressor from each particular virus. Other candidate silencing suppressors may be obtained by examining viral genome sequences for polypeptides encoded at the same position within the viral genome, relative to the structure of a related viral genome comprising a known silencing suppressor, as is appreciated by a person of skill in the art.

Silencing suppressors can be categorized based on their mode of action. Suppressors such as V2 which preferentially bind to a double-stranded RNA molecule which has overhanging 5' ends relative to a corresponding double-stranded RNA molecule having blunt ends have been found to be particularly useful for enhancing transgene expression when used in combination with gene silencing, in particular with the use of an exogenous polynucleotide encoding a dsRNA. Other suppressors such as p19 which preferentially bind a dsRNA molecule which is 21 base pairs in length relative to a dsRNA molecule of a different length can also allow transgene expression in the presence of an exogenous polynucleotide encoding a dsRNA, but generally to a lesser degree than, for example, V2. This allows the selection of an optimal combination of dsRNA, silencing suppressor and over-expressed transgene for a particular purpose. Such optimal combinations can be identified using a method of the invention.

In an embodiment, the silencing suppressor preferentially binds to a double-stranded RNA molecule which has overhanging 5' ends relative to a corresponding double-stranded RNA molecule having blunt ends. In this context, the corresponding double-stranded RNA molecule preferably has the same nucleotide sequence as the molecule with the 5' overhanging ends, but without the overhanging 5' ends. Binding assays are routinely performed, for example in in vitro assays, by any method as known to a person of skill in the art.

In a further embodiment, the silencing suppressor comprises amino acids having a sequence as provided in any one of SEQ ID NOs:1, or 38 to 51, a biologically active fragment thereof, or an amino acid sequence which is at least 30% identical to any one or more of SEQ ID NOs:1, or 38 to 51.

Multiple copies of a suppressor may be used. Different suppressors may be used together (e.g., in tandem).

Essentially any RNA molecule of interest which is desirable to be expressed in a cell, organism or part can be co-expressed with the silencing suppressor. The RNA molecule may influence, for example, an agronomic trait, insect resistance, disease resistance, herbicide resistance, sterility, grain characteristics, and the like. The encoded polypeptides may be involved in metabolism of lipid, starch, carbohydrates, nutrients, etc., or may be responsible for the synthesis of proteins, peptides, lipids, waxes, starches, sugars, carbohydrates, flavors, odors, toxins, carotenoids. hormones, polymers, flavonoids, storage proteins, phenolic acids, alkaloids, lignins, tannins, celluloses, glycoproteins, glycolipids, etc.

In a particular example, the plants produce increased levels of enzymes for lipid production in plants such as Brassicas, for example oilseed rape or sunflower, safflower, flax, cotton, soybean or maize.

Silencing

As used herein, the term "a double stranded RNA (dsRNA) molecule which comprises a first nucleotide sequence which is complementary to a region of a target RNA encoded by a first polynucleotide of interest" or variations thereof refers to an RNA molecule which can be used to downregulate the levels of a target RNA, and/or the amount of protein encoded by the target RNA, in a cell, comprising a double-stranded RNA region comprising the first nucleotide sequence ("antisense sequence") and its complement ("sense sequence"). The target RNA, which is encoded by the first polynucleotide of interest which may be an RNA molecule (e.g. a viral RNA molecule) or preferably a DNA molecule which is transcribed (or replicated) in the cell to produce the target RNA, may be produced by the genome of the cell, or may be produced by a pathogen of the cell such as a virus. Thus, due to temporal and/or spatial expression patterns of an endogenous gene, or the absence of the pathogen, the dsRNA may not always be present in the cell at the same time as the target RNA.

As the skilled person would appreciate, to exert the desired effect a dsRNA targeting the transcription product of an endogenous gene will be expressed at least some of the same time as the endogenous gene. Whilst, as described below, the dsRNA may comprise single stranded regions, the double stranded region comprises a sequence (antisense sequence) which is complementary to a region of the target. Typically, the complementary region is at least 19 consecutive nucleotides in length, preferably 19-30 nucleotides for use in vertebrate animal cells such as mammalian cells, more preferably 19-25 nucleotides, most preferably of 20, 21, 22, 23 or 24 nucleotides in length. The complementarity may be partial or complete to the region of the target RNA. Partial complementarity, particularly in the context of a target RNA in an animal cell such as a vertebrate animal cell or mammalian animal cell preferably includes a region of at least 6 consecutive nucleotides, preferably at least 7, at least 8, at least 9, or at least 10 consecutive nucleotides, and preferably includes consecutive nucleotides 2-8 of the nucleotide sequence counting from the 5' end.

For plant cells, the complementarity is preferably full complementarity over a region of 19, 20 or 21 consecutive nucleotides, or over a region of at least 30 nucleotides, at least 50 nucleotides, or at least 100 nucleotides when the dsRNA molecule is a hairpin RNA. Complementarity in the context of this paragraph includes G:U basepairs as well as G:C and A:U basepairs.

RNA Interference

RNA interference (RNAi) is particularly useful for specifically inhibiting the production of a particular protein or functional RNA. This technology relies on the presence of dsRNA molecules that contain a sequence that is essentially identical to the mRNA of the gene of interest or part thereof. Conveniently, the dsRNA can be produced from a single promoter in a recombinant vector or host cell, where the sense and anti-sense sequences are flanked by an unrelated sequence which enables the sense and anti-sense sequences to hybridize to form the dsRNA molecule with an unrelated sequence forming a loop structure, although a sequence with identity to the target RNA or its complement can form the loop structure. Typically, the dsRNA is encoded by a double-stranded DNA construct which has sense and antisense sequences in an inverted repeat structure, arranged as an interrupted palindrome, where the repeated sequences are transcribed to produce the hybridising sequences in the dsRNA molecule, and the interrupt sequence is transcribed to form the loop in the dsRNA molecule. The design and production of suitable dsRNA molecules is well within the capacity of a person skilled in the art, particularly considering Waterhouse et al. (1998), Smith et al. (2000), WO 99/32619, WO 99/53050, WO 99/49029, and WO 01/34815.

In one example, a DNA is introduced that directs the synthesis of an at least partly double stranded RNA product(s) with homology, preferably at least 19 consecutive nucleotides complementary to a region of, a target RNA, to be inactivated. The DNA therefore comprises both sense and antisense sequences that, when transcribed into RNA, can hybridize to form the double stranded RNA region. In one embodiment of the invention, the sense and antisense sequences are separated by a spacer region that comprises an intron which, when transcribed into RNA, is spliced out. This arrangement has been shown to result in a higher efficiency of gene silencing. The double stranded region may comprise one or two RNA molecules, transcribed from either one DNA region or two. The presence of the double stranded molecule is thought to trigger a response from an endogenous system that destroys both the double stranded RNA and also the homologous RNA transcript from the target gene, efficiently reducing or eliminating the activity of the target gene.

The length of the sense and antisense sequences that hybridize should each be at least 19 contiguous nucleotides. The full-length sequence corresponding to the entire gene transcript may be used. The degree of identity of the sense and antisense sequences to the targeted transcript should be at least 85%, at least 90%, or at least 95-100%. The RNA molecule may of course comprise unrelated sequences which may function to stabilize the molecule. The RNA molecule may be expressed under the control of a RNA polymerase II or RNA polymerase III promoter. Examples of the latter include tRNA or snRNA promoters.

Furthermore, it has been established by the inventors that the position of the complementary sequence relevant to the target, namely with respect to the 5' or 3' end, can influence the level of silencing in the presence of a silencing suppressor polypeptide. Thus, using a method of the invention an optimal combination of dsRNA sequence and silencing suppressor can be determined on an as needs basis.

Preferred small interfering RNA ("siRNA") molecules comprise a nucleotide sequence that is identical to about 19-21 contiguous nucleotides of the target mRNA. Preferably, the siRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the organism in which it is to be introduced, for example, as determined by standard BLAST search.

microRNA

MicroRNAs (abbreviated miRNAs) are generally 19-25 nucleotides (commonly about 20-24 nucleotides in plants) non-coding RNA molecules that are derived from larger precursors that form imperfect stem-loop structures.

miRNAs bind to complementary sequences on target messenger RNA transcripts (mRNAs), usually resulting in translational repression or target degradation and gene silencing.

In a preferred embodiment, the miRNA is an artificial (man made) miRNA. In otherwords, the miRNA is a non-naturally occurring miRNA.

In a further particularly preferred embodiment, if the dsRNA is a miRNA such as a miRNA comprising a dsRNA region of 21 base pairs expressed as a precursor miRNA, and the cell further comprises the third exogenous polynucleotide, the silencing suppressor is a V2-like polypeptide such as those comprising amino acids having a sequence as provided in any one of SEQ ID NOs:1, or 38 to 51, a biologically active fragment thereof, or an amino acid sequence which is at least 30% identical to any one or more of SEQ ID NOs:1, or 38 to 51.

In plant cells, miRNA precursor molecules are believed to be largely processed in the nucleus. The pri-miRNA (containing one or more local double-stranded or "hairpin" regions as well as the usual 5' "cap" and polyadenylated tail of an mRNA) is processed to a shorter miRNA precursor molecule that also includes a stem-loop or fold-back structure and is termed the "pre-miRNA". In plants, the pre-miRNAs are cleaved by distinct DICER-like (DCL) enzymes, in particular DCL-1, yielding miRNA:miRNA* duplexes. Prior to transport out of the nucleus, these duplexes are methylated. In contrast, hairpin RNA molecules having longer dsRNA regions are processed in particular by DCL-3 and DCL-4. Most mammalian cells have only a single DICER polypeptide which cleaves multiple dsRNA structures.

In the cytoplasm, the miRNA strand from the miRNA:miRNA duplex is selectively incorporated into an active RNA-induced silencing complex (RISC) for target recognition. The RISC-complexes contain a particular subset of Argonaute proteins that exert sequence-specific gene repression (see, for example, Millar and Waterhouse, 2005; Pasquinelli et al., 2005; Almeida and Allshire, 2005).

Cosuppression

Genes can suppress the expression of related endogenous genes and/or transgenes already present in the genome, a phenomenon termed homology-dependent gene silencing. Most of the instances of homology dependent gene silencing fall into two classes—those that function at the level of transcription of the transgene, and those that operate post-transcriptionally.

Post-transcriptional homology-dependent gene silencing (i.e., cosuppression) describes the loss of expression of a transgene and related endogenous or viral genes in transgenic plants. Cosuppression often, but not always, occurs when transgene transcripts are abundant, and it is generally thought to be triggered at the level of mRNA processing, localization, and/or degradation. Several models exist to explain how cosuppression works (see in Taylor, 1997).

One model, the "quantitative" or "RNA threshold" model, proposes that cells can cope with the accumulation of large amounts of transgene transcripts, but only up to a point. Once that critical threshold has been crossed, the sequence-dependent degradation of both transgene and related endogenous gene transcripts is initiated. It has been proposed that this mode of cosuppression may be triggered following the synthesis of copy RNA (cRNA) molecules by reverse transcription of the excess transgene mRNA, presumably by endogenous RNA-dependent RNA polymerases. These cRNAs may hybridize with transgene and endogenous mRNAs, the unusual hybrids targeting homologous transcripts for degradation. However, this model does not account for reports suggesting that cosuppression can apparently occur in the absence of transgene transcription and/or without the detectable accumulation of transgene transcripts.

To account for these data, a second model, the "qualitative" or "aberrant RNA" model, proposes that interactions between transgene RNA and DNA and/or between endogenous and introduced DNAs lead to the methylation of transcribed regions of the genes. The methylated genes are proposed to produce RNAs that are in some way aberrant, their anomalous features triggering the specific degradation of all related transcripts. Such aberrant RNAs may be produced by complex transgene loci, particularly those that contain inverted repeats.

A third model proposes that intermolecular base pairing between transcripts, rather than cRNA-mRNA hybrids generated through the action of an RNA-dependent RNA polymerase, may trigger cosuppression. Such base pairing may become more common as transcript levels rise, the putative double-stranded regions triggering the targeted degradation of homologous transcripts. A similar model proposes intramolecular base pairing instead of intermolecular base pairing between transcripts.

Cosuppression involves introducing an extra copy of a gene or a fragment thereof into a plant in the sense orientation with respect to a promoter for its expression. A skilled person would appreciate that the size of the sense fragment, its correspondence to target gene regions, and its degree of sequence identity to the target gene can vary. In some instances, the additional copy of the gene sequence interferes with the expression of the target plant gene. Reference is made to WO 97/20936 and EP 0465572 for methods of implementing co-suppression approaches.

The present inventors postulate that the V2 silencing suppressor and its functional analogs suppress the co-suppression pathway but not, or to a lesser extent, the microRNA and RNA interference pathways as described above.

Polynucleotides

The terms "polynucleotide", and "nucleic acid" are used interchangeably. They refer to a polymeric form of nucleotides of any length, either deoxyribonucleotides or ribonucleotides, or analogs thereof. A polynucleotide useful for the invention may be of genomic, cDNA, semisynthetic, or synthetic origin, double-stranded or single-stranded and by virtue of its origin or manipulation: (1) is not associated with all or a portion of a polynucleotide with which it is associated in nature, (2) is linked to a polynucleotide other than that to which it is linked in nature, or (3) does not occur in nature. The following are non-limiting examples of polynucleotides: coding regions which may or may not include introns, messenger RNA (mRNA), transfer RNA (tRNA), ribosomal RNA (rRNA), cDNA, recombinant polynucleotides, branched polynucleotides, plasmids, vectors, isolated DNA of any sequence, and chimeric DNA including DNA constructs.

As used herein, the term "gene" is to be taken in its broadest context and includes the deoxyribonucleotide sequences comprising the transcribed region and, if translated, the protein coding region, of a structural gene and including sequences located adjacent to the coding region on both the 5' and 3' ends for a distance of at least about 2 kb on either end and which are involved in expression of the gene. In this regard, the gene includes control signals such as promoters, enhancers, termination and/or polyadenylation signals that are naturally associated with a given gene, or heterologous control signals, in which case, the gene is referred to as a "chimeric gene". The sequences which are located 5' of the protein coding region and which are present on the mRNA are referred to as 5' non-translated sequences. The sequences which are located 3' or downstream of the protein coding region and which are present on the mRNA are referred to as 3' non-translated sequences. The term "gene" encompasses both cDNA and genomic forms of a gene. A genomic form or clone of a gene contains the coding region which may be interrupted with non-coding sequences termed "introns", "intervening regions", or "intervening sequences." Introns are segments of a gene which are transcribed into nuclear RNA (nRNA). Introns may contain regulatory elements such as enhancers. Introns are removed or "spliced out" from the nuclear or primary transcript; introns therefore are absent in the mRNA transcript. The mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above.

As used herein, "chimeric DNA" refers to any DNA molecule that is not naturally found in nature; also referred to herein as a "DNA construct". Typically, chimeric DNA comprises regulatory and transcribed or protein coding sequences that are not naturally found together in nature. Accordingly, chimeric DNA may comprise regulatory sequences and coding sequences that are derived from different sources, or regulatory sequences and coding sequences derived from the same source, but arranged in a manner different than that found in nature. The open reading frame may or may not be linked to its natural upstream and downstream regulatory elements. The open reading frame may be incorporated into, for example, a plant genome, in a non-natural location, or in a replicon or vector where it is not naturally found such as a bacterial plasmid or a viral vector. The term "chimeric DNA" is not limited to DNA molecules which are replicable in a host, but includes DNA capable of being ligated into a replicon by, for example, specific adaptor sequences.

A "transgene" is a gene that has been introduced into the genome by a transformation procedure. The terms "genetically modified", "transgenic", "recombinant" and variations thereof include introducing a gene into a cell by transformation or transduction, mutating a gene in a cell and genetically altering or modulating the regulation of a gene in a cell, or the progeny of any cell modified as described above.

A "genomic region" as used herein refers to a position within the genome where a transgene, or group of transgenes (also referred to herein as a cluster), have been inserted into a cell, or predecessor thereof. Such regions only comprise nucleotides that have been incorporated by the intervention of man such as by methods described herein.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 40%, more preferably at least 50%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

A polynucleotide of, or useful for, the present invention may selectively hybridise, under stringent conditions, to a polynucleotide defined herein. As used herein, stringent conditions are those that: (1) employ during hybridisation a denaturing agent such as formamide, for example, 50% (v/v) formamide with 0.1% (w/v) bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (2) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2×SSC and 0.1% SDS, and/or (3) employ low ionic strength and high temperature for washing, for example, 0.015 M NaCl/0.0015 M sodium citrate/0.1% SDS at 50° C. Shorter polynucleotides, for example those of 19-24 nucleotides, require less stringent conditions for hybridisation, as is well understood by persons of skill in the art. For example, the hybridisation conditions may omit the formamide, and the washing conditions use a temperature of 37° C. with higher salt and lower SDS concentrations.

Polynucleotides of the invention may possess, when compared to naturally occurring molecules, one or more mutations which are deletions, insertions, or substitutions of nucleotide residues. Polynucleotides which have mutations relative to a reference sequence can be either naturally occurring (that is to say, isolated from a natural source) or synthetic (for example, by performing site-directed mutagenesis or DNA shuffling on the nucleic acid).

Expression Vector

As used herein, an "expression vector" is a DNA or RNA vector that is capable of transforming a host cell and of effecting expression of one or more specified polynucleotides. Preferably, the expression vector is also capable of replicating within the host cell. Expression vectors are typically viruses or plasmids. Expression vectors of the present invention include any vectors that function (i.e., direct gene expression) in host cells of the present invention, including in fungal, endoparasite, arthropod, animal, algal, and plant cells. Particularly preferred expression vectors of the present invention can direct gene expression in yeast, animal, and/or plant cells.

"Operably linked" as used herein, refers to a functional relationship between two or more nucleic acid (e.g., DNA) segments. Typically, it refers to the functional relationship of transcriptional regulatory element (promoter) to a transcribed sequence. For example, a promoter is operably linked to a coding sequence of a polynucleotide defined herein, if it stimulates or modulates the transcription of the coding sequence in an appropriate cell. Generally, promoter transcriptional regulatory elements that are operably linked to a transcribed sequence are physically contiguous to the transcribed sequence, i.e., they are cis-acting. However, some transcriptional regulatory elements such as enhancers, need not be physically contiguous or located in close proximity to the coding sequences whose transcription they enhance.

Expression vectors of the present invention contain regulatory sequences such as transcription control sequences, translation control sequences, origins of replication, and other regulatory sequences that are compatible with the host cell and that control the expression of polynucleotides of the present invention. In particular, expression vectors of the present invention include transcription control sequences. Transcription control sequences are sequences which control the initiation, elongation, and termination of transcription. Particularly important transcription control sequences are those which control transcription initiation such as promoter, enhancer, operator and repressor sequences. Suitable transcription control sequences include any transcription control sequence that can function in at least one of the recombinant cells of the present invention. The choice of the regulatory sequences used depends on the target organism such as a plant and/or target organ or tissue of interest. Such regulatory sequences may be obtained from any eukaryotic organism such as plants or plant viruses, or may be chemically synthesized. A variety of such transcription control sequences are known to those skilled in the art. Particularly preferred transcription control sequences are promoters active in directing transcription in plants, either constitutively or stage and/or tissue specific, depending on the use of the plant or part(s) thereof.

A number of vectors suitable for stable transfection of plant cells or for the establishment of transgenic plants have been described in for example, Pouwels et al., Cloning Vectors: A Laboratory Manual, 1985, supp. 1987, Weissbach and Weissbach, Methods for Plant Molecular Biology, Academic Press, 1989, and Gelvin et al., Plant Molecular Biology Manual, Kluwer Academic Publishers, 1990. Typically, plant expression vectors include for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A number of constitutive promoters that are active in plant cells have been described. Suitable promoters for constitutive expression in plants include, but are not limited to, the cauliflower mosaic virus (CaMV) 35S promoter, the Figwort mosaic virus (FMV) 35S, the sugarcane bacilliform virus promoter, the commelina yellow mottle virus promoter, the light-inducible promoter from the small subunit of the ribulose-1,5-bis-phosphate carboxylase, the rice cytosolic triosephosphate isomerase promoter, the adenine phosphoribosyltransferase promoter of *Arabidopsis*, the rice actin 1 gene promoter, the mannopine synthase and octopine synthase promoters, the Adh promoter, the sucrose synthase promoter, the R gene complex promoter, and the chlorophyll α/β binding protein gene promoter. These promoters have been used to create DNA vectors that have been expressed in plants, see for example, WO 84/02913. All of these promoters have been used to create various types of plant-expressible recombinant DNA vectors.

For the purpose of expression in source tissues of the plant such as the leaf, seed, root or stem, it is preferred that the promoters utilized in the present invention have relatively high expression in these specific tissues. For this purpose, one may choose from a number of promoters for genes with tissue- or cell-specific, or -enhanced expression. Examples of such promoters reported in the literature include, the chloroplast glutamine synthetase GS2 promoter from pea, the chloroplast fructose-1,6-biphosphatase promoter from wheat, the nuclear photosynthetic ST-LS1 promoter from potato, the serine/threonine kinase promoter and the glucoamylase (CHS) promoter from *Arabidopsis thaliana*. Also reported to be active in photosynthetically active tissues are the ribulose-1,5-bisphosphate carboxylase promoter from eastern larch (*Larix laricina*), the promoter for the Cab gene, Cab6, from pine, the promoter for the Cab-1 gene from wheat, the promoter for the Cab-1 gene from spinach, the promoter for the Cab 1R gene from rice, the pyruvate, orthophosphate dikinase (PPDK) promoter from *Zea mays*, the promoter for the tobacco Lhcb1*2 gene, the *Arabidopsis thaliana* Suc2 sucrose-H$^{30}$ symporter promoter, and the promoter for the thylakoid membrane protein genes from spinach (PsaD, PsaF, PsaE, PC, FNR, AtpC, AtpD, Cab, RbcS). Other promoters for the chlorophyll α/β-binding proteins may also be utilized in the present invention such as the promoters for LhcB gene and PsbP gene from white mustard (*Sinapis alba*).

A variety of plant gene promoters that are regulated in response to environmental, hormonal, chemical, and/or developmental signals, also can be used for expression of RNA-binding protein genes in plant cells, including promoters regulated by (1) heat, (2) light (e.g., pea RbcS-3A promoter, maize RbcS promoter), (3) hormones such as abscisic acid, (4) wounding (e.g., WunI), or (5) chemicals such as methyl jasmonate, salicylic acid, steroid hormones, alcohol, Safeners (WO 97/06269), or it may also be advantageous to employ (6) organ-specific promoters.

For the purpose of expression in sink tissues of the plant such as the tuber of the potato plant, the fruit of tomato, or the seed of soybean, canola, cotton, *Zea mays*, wheat, rice, and barley, it is preferred that the promoters utilized in the present invention have relatively high expression in these specific tissues. A number of promoters for genes with tuber-specific or -enhanced expression are known, including the class I patatin promoter, the promoter for the potato tuber ADPGPP genes, both the large and small subunits, the sucrose synthase promoter, the promoter for the major tuber proteins, including the 22 kD protein complexes and proteinase inhibitors, the promoter for the granule bound starch synthase gene (GBSS), and other class I and II patatins promoters. Other promoters can also be used to express a protein in specific tissues such as seeds or fruits. The promoter for β-conglycinin or other seed-specific promoters such as the napin, zein, linin and phaseolin promoters, can be used. Root specific promoters may also be used. An example of such a promoter is the promoter for the acid chitinase gene. Expression in root tissue could also be accomplished by utilizing the root specific subdomains of the CaMV 35S promoter that have been identified.

In one embodiment, the promoter directs expression in tissues and organs in which lipid biosynthesis take place. Such promoters act in seed development at a suitable time for modifying lipid composition in seeds.

In a further particularly preferred embodiment, the promoter is a plant storage organ specific promoter. As used herein, the term "plant storage organ specific promoter" refers to a promoter that preferentially, when compared to other plant tissues, directs gene transcription in a storage organ of a plant. Preferably, the promoter only directs expression of a gene of interest in the storage organ, and/or expression of the gene of interest in other parts of the plant such as leaves is not detectable by Northern blot analysis and/or RT-PCR. Typically, the promoter drives expression of genes during growth and development of the storage organ, in particular during the phase of synthesis and accumulation of storage compounds in the storage organ. Such promoters may drive gene expression in the entire plant storage organ or only part thereof such as the seedcoat, embryo or cotyledon(s) in seeds of dicotyledonous plants or the endosperm or aleurone layer of seeds of monocotyledonous plants.

In one embodiment, the plant storage organ specific promoter is a seed specific promoter. In a more preferred embodiment, the promoter preferentially directs expression in the cotyledons of a dicotyledonous plant or in the endosperm of a monocotyledonous plant, relative to expression in the embryo of the seed or relative to other organs in the plant such as leaves. Preferred promoters for seed-specific expression include: 1) promoters from genes encoding enzymes involved in lipid biosynthesis and accumulation in seeds such as desaturases and elongases, 2) promoters from genes encoding seed storage proteins, and 3) promoters from genes encoding enzymes involved in carbohydrate biosynthesis and accumulation in seeds. Seed specific promoters which are suitable are, the oilseed rape napin gene promoter (U.S. Pat. No. 5,608,152), the *Vicia faba* USP promoter (Baumlein et al., 1991), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980), or the legumin B4 promoter (Baumlein et al., 1992), and promoters which lead to the seed-specific expression in monocots such as maize, barley, wheat, rye, rice and the like. Notable promoters which are suitable are the barley lpt2 or lpt1 gene promoter (WO 95/15389 and WO 95/23230), or the promoters described in WO 99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the sorghum kasirin gene, the rye secalin gene). Other promoters include those described by Broun et al. (1998), Potenza et al. (2004), US 20070192902 and US 20030159173. In an embodiment, the seed specific promoter is preferentially expressed in defined parts of the seed such as the cotyledon(s) or the endosperm. Examples of cotyledon specific promoters include, but are not limited to, the FP1 promoter (Ellerstrom et al., 1996), the pea legumin promoter (Perrin et al., 2000), and the bean phytohemagglutnin promoter (Perrin et al., 2000). Examples of endosperm specific promoters include, but are not limited to, the maize zein-1 promoter (Chikwamba et al., 2003), the rice glutelin-1 promoter (Yang et al., 2003), the barley D-hordein promoter (Horvath et al., 2000) and wheat HMW glutenin promoters (Alvarez et al., 2000). In a further embodiment, the seed specific promoter is not expressed, or is only expressed at a low level, in the embryo and/or after the seed germinates.

In another embodiment, the plant storage organ specific promoter is a tuber specific promoter. Examples include, but are not limited to, the potato patatin B33, PAT21 and GBSS promoters, as well as the sweet potato sporamin promoter (for review, see Potenza et al., 2004). In a preferred embodiment, the promoter directs expression preferentially in the pith of the tuber, relative to the outer layers (skin, bark) or the embryo of the tuber.

In another embodiment, the plant storage organ specific promoter is a fruit specific promoter. Examples include, but are not limited to, the tomato polygalacturonase, E8 and Pds promoters, as well as the apple ACC oxidase promoter (for review, see Potenza et al., 2004). In a preferred embodiment, the promoter preferentially directs expression in the edible parts of the fruit, for example the pith of the fruit, relative to the skin of the fruit or the seeds within the fruit.

When there are multiple promoters present, each promoter may independently be the same or different.

The 5' non-translated leader sequence can be derived from the promoter selected to express the heterologous gene sequence of the polynucleotide, or may be heterologous with respect to the coding region of the enzyme to be produced, and can be specifically modified if desired so as to increase translation of mRNA. For a review of optimizing expression of transgenes, see Koziel et al. (1996). The 5' non-translated regions can also be obtained from plant viral RNAs (Tobacco mosaic virus, Tobacco etch virus, Maize dwarf mosaic virus, Alfalfa mosaic virus, among others) from suitable eukaryotic genes, plant genes (wheat and maize chlorophyll a/b binding protein gene leader), or from a synthetic gene sequence. The present invention is not limited to constructs wherein the non-translated region is derived from the 5' non-translated sequence that accompanies the promoter sequence. The leader sequence could also be derived from an unrelated promoter or coding sequence. Leader sequences useful in context of the present invention comprise the maize Hsp70 leader (U.S. Pat. Nos. 5,362,865 and 5,859,347), and the TMV omega element.

The termination of transcription is accomplished by a 3' non-translated DNA sequence operably linked in the expression vector to the polynucleotide of interest. The 3' non-translated region of a recombinant DNA molecule contains a polyadenylation signal that functions in plants to cause the addition of adenylate nucleotides to the 3' end of the RNA. The 3' non-translated region can be obtained from various genes that are expressed in, for example, plant cells. The nopaline synthase 3' untranslated region, the 3' untranslated region from pea small subunit Rubisco gene, the 3' untranslated region from soybean 7S seed storage protein gene are commonly used in this capacity. The 3' transcribed, non-translated regions containing the polyadenylate signal of Agrobacterium tumor-inducing (Ti) plasmid genes are also suitable.

Recombinant DNA technologies can be used to improve expression of a transformed polynucleotide by manipulating for example, the number of copies of the polynucleotide within a host cell, the efficiency with which those polynucleotide are transcribed, the efficiency with which the resultant transcripts are translated, and the efficiency of post-translational modifications. Recombinant techniques useful for increasing the expression of polynucleotides defined herein include, but are not limited to, operatively linking the polynucleotide to a high-copy number plasmid, integration of the polynucleotide molecule into one or more host cell chromosomes, addition of vector stability sequences to the plasmid, substitutions or modifications of transcription control signals (e.g., promoters, operators, enhancers), substitutions or modifications of translational control signals (e.g., ribosome binding sites, Shine-Dalgarno sequences), modification of the polynucleotide to correspond to the codon usage of the host cell, and the deletion of sequences that destabilize transcripts.

In an embodiment, if the cell is a plant cell, the second exogenous polynucleotide was introduced into the cell on a vector other than a viral vector.

Recombinant vectors may also contain: (a) one or more secretory signals which encode signal peptide sequences, to enable an expressed polypeptide defined herein to be secreted from the cell that produces the polypeptide, or which provide for localisation of the expressed polypeptide, for example, for retention of the polypeptide in the endoplasmic reticulum (ER) in the cell, or transfer into a plastid, and/or (b) contain fusion sequences which lead to the expression of nucleic acid molecules as fusion proteins. Examples of suitable signal segments include any signal segment capable of directing the secretion or localisation of a polypeptide defined herein. Preferred signal segments include, but are not limited to, Nicotiana nectarin signal peptide (U.S. Pat. No. 5,939,288), tobacco extensin signal, or the soy oleosin oil body binding protein signal. Recombinant vectors may also include intervening and/or untranslated sequences surrounding and/or within the nucleic acid sequence of a polynucleotide defined herein.

To facilitate identification of transformants, the recombinant vector desirably comprises a selectable or screenable marker gene as, or in addition to, the nucleic acid sequence of a polynucleotide defined herein. By "marker gene" is meant a gene that imparts a distinct phenotype to cells expressing the marker gene and thus, allows such transformed cells to be distinguished from cells that do not have the marker. A selectable marker gene confers a trait for which one can "select" based on resistance to a selective agent (e.g., a herbicide, antibiotic, radiation, heat, or other treatment damaging to untransformed cells). A screenable marker gene (or reporter gene) confers a trait that one can identify through observation or testing, that is, by "screening" (e.g., β-glucuronidase, luciferase, GFP or other enzyme activity not present in untransformed cells). The marker gene and the nucleotide sequence of interest do not have to be linked, since co-transformation of unlinked genes as for example, described in U.S. Pat. No. 4,399,216, is also an efficient process in for example, plant transformation. The actual choice of a marker is not crucial as long as it is functional (i.e., selective) in combination with the cells of choice such as a plant cell.

Exemplary selectable markers for selection of plant transformants include, but are not limited to, a hyg gene which encodes hygromycin B resistance; a neomycin phosphotransferase (nptII) gene conferring resistance to kanamycin, paromomycin, G418; a glutathione-S-transferase gene from rat liver conferring resistance to glutathione derived herbicides as for example, described in EP 256223; a glutamine synthetase gene conferring, upon overexpression, resistance to glutamine synthetase inhibitors such as phosphinothricin as for example, described in WO 87/05327; an acetyltransferase gene from Streptomyces viridochromogenes conferring resistance to the selective agent phosphinothricin as for example, described in EP 275957; a gene encoding a 5-enolshikimate-3-phosphate synthase (EPSPS) conferring tolerance to N-phosphonomethylglycine as for example, described by Hinchee et al. (1988); a bar gene conferring resistance against bialaphos as for example, described in WO91/02071; a nitrilase gene such as bxn from Klebsiella ozaenae which confers resistance to bromoxynil (Stalker et al., 1988); a dihydrofolate reductase (DHFR) gene conferring resistance to methotrexate (Thillet et al., 1988); a mutant acetolactate synthase gene (ALS) which confers resistance to imidazolinone, sulfonylurea, or other ALS-inhibiting chemicals (EP 154,204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding a β-glucuronidase (GUS) enzyme for which various chromogenic substrates are known; a β-galactosidase gene encoding an enzyme for which chromogenic substrates are known; an aequorin gene (Prasher et al., 1985) which may be employed in calcium-sensitive bioluminescence detection; a green fluorescent protein gene (Niedz et al., 1995) or derivatives thereof; or a luciferase (luc) gene (Ow et al., 1986) which allows for bioluminescence detection. By "reporter molecule" it is meant a molecule that, by its chemical nature, provides an analytically identifiable signal that facilitates determination of promoter activity by reference to protein product.

Preferably, the recombinant vector is stably incorporated into the genome of the cell such as the plant cell. Accordingly, the recombinant vector may comprise appropriate elements which allow the vector to be incorporated into the genome, or into a chromosome of the cell.

Transfer Nucleic Acids

Transfer nucleic acids can be used to deliver an exogenous polynucleotide to a cell and comprise one, preferably two, border sequences and a polynucleotide of interest. The transfer nucleic acid may or may not encode a selectable marker. Preferably, the transfer nucleic acid forms part of a binary vector in a bacterium, where the binary vector further comprises elements which allow replication of the vector in the bacterium, selection, or maintenance of bacterial cells containing the binary vector. Upon transfer to a eukaryotic cell, the transfer nucleic acid component of the binary vector is capable of integration into the genome of the eukaryotic cell.

As used herein, the term "extrachromosomal transfer nucleic acid" refers to a nucleic acid molecule that is capable of being transferred from a bacterium such as *Agrobacterium* sp., to a eukaryotic cell such as a plant leaf cell. An extrachromosomal transfer nucleic acid is a genetic element that is well-known as an element capable of being transferred, with the subsequent integration of a nucleotide sequence contained within its borders into the genome of the recipient cell. In this respect, a transfer nucleic acid is flanked, typically, by two "border" sequences, although in some instances a single border at one end can be used and the second end of the transferred nucleic acid is generated randomly in the transfer process. A polynucleotide of interest is typically positioned between the left border-like sequence and the right border-like sequence of a transfer nucleic acid. The polynucleotide contained within the transfer nucleic acid may be operably linked to a variety of different promoter and terminator regulatory elements that facilitate its expression, that is, transcription and/or translation of the polynucleotide. Transfer DNAs (T-DNAs) from *Agrobacterium* sp. such as *Agrobacterium tumefaciens* or *Agrobacterium rhizogenes*, and man made variants/mutants thereof are probably the best characterized examples of transfer nucleic acids. Another example is P-DNA ("plant-DNA") which comprises T-DNA border-like sequences from plants.

As used herein, "T-DNA" refers to for example, T-DNA of an *Agrobacterium tumefaciens* Ti plasmid or from an *Agrobacterium rhizogenes* Ri plasmid, or man made variants thereof which function as T-DNA. The T-DNA may comprise an entire T-DNA including both right and left border sequences, but need only comprise the minimal sequences required in cis for transfer, that is, the right and T-DNA border sequence. The T-DNAs of the invention have inserted into them, anywhere between the right and left border sequences (if present), the polynucleotide of interest flanked by target sites for a site-specific recombinase. The sequences encoding factors required in trans for transfer of the T-DNA into a plant cell such as vir genes, may be inserted into the T-DNA, or may be present on the same replicon as the T-DNA, or preferably are in trans on a compatible replicon in the *Agrobacterium* host. Such "binary vector systems" are well known in the art.

As used herein, "P-DNA" refers to a transfer nucleic acid isolated from a plant genome, or man made variants/mutants thereof, and comprises at each end, or at only one end, a T-DNA border-like sequence. The border-like sequence preferably shares at least 50%, at least 60%, at least 70%, at least 75%, at least 80%, at least 90% or at least 95%, but less than 100% sequence identity, with a T-DNA border sequence from an *Agrobacterium* sp. such as *Agrobacterium tumefaciens* or *Agrobacterium rhizogenes*. Thus, P-DNAs can be used instead of T-DNAs to transfer a nucleotide sequence contained within the P-DNA from, for example *Agrobacterium*, to another cell. The P-DNA, before insertion of the exogenous polynucleotide which is to be transferred, may be modified to facilitate cloning and should preferably not encode any proteins. The P-DNA is characterized in that it contains, at least a right border sequence and preferably also a left border sequence.

As used herein, a "border" sequence of a transfer nucleic acid can be isolated from a selected organism such as a plant or bacterium, or be a man made variant/mutant thereof. The border sequence promotes and facilitates the transfer of the polynucleotide to which it is linked and may facilitate its integration in the recipient cell genome. In an embodiment, a border-sequence is between 5-100 base pairs (bp) in length, 10-80 bp in length, 15-75 bp in length, 15-60 bp in length, 15-50 bp in length, 15-40 bp in length, 15-30 bp in length, 16-30 bp in length, 20-30 bp in length, 21-30 bp in length, 22-30 bp in length, 23-30 bp in length, 24-30 bp in length, 25-30 bp in length, or 26-30 bp in length. Border sequences from T-DNA from *Agrobacterium* sp. are well known in the art and include those described in Lacroix et al. (2008), Tzfira and Citovsky (2006) and Glevin (2003).

Whilst traditionally only *Agrobacterium* sp. have been used to transfer genes to plants cells, there are now a large number of systems which have been identified/developed which act in a similar manner to *Agrobacterium* sp. Several non-*Agrobacterium* species have recently been genetically modified to be competent for gene transfer (Chung et al., 2006; Broothaerts et al., 2005). These include *Rhizobium* sp. NGR234, *Sinorhizobium meliloti* and *Mezorhizobium loti*. The bacteria are made competent for gene transfer by providing the bacteria with the machinery needed for the transformation process, that is, a set of virulence genes encoded by an *Agrobacterium* Ti-plasmid and the T-DNA segment residing on a separate, small binary plasmid. Bacteria engineered in this way are capable of transforming different plant tissues (leaf disks, calli and oval tissue), monocots or dicots, and various different plant species (e.g., tobacco, rice).

Direct transfer of eukaryotic expression plasmids from bacteria to eukaryotic hosts was first achieved several decades ago by the fusion of mammalian cells and protoplasts of plasmid-carrying *Escherichia coli* (Schaffner, 1980). Since then, the number of bacteria capable of delivering genes into mammalian cells has steadily increased (Weiss, 2003), being discovered by four groups independently (Sizemore et al. 1995; Courvalin et al., 1995; Powell et al., 1996; Darji et al., 1997).

Attenuated *Shigella flexneri, Salmonella typhimurium* or *E. coli* that had been rendered invasive by the virulence plasmid (pWR100) of *S. flexneri* have been shown to be able to transfer expression plasmids after invasion of host cells and intracellular death due to metabolic attenuation. Mucosal application, either nasally or orally, of such recombinant *Shigella* or *Salmonella* induced immune responses against the antigen that was encoded by the expression plasmids. In the meantime, the list of bacteria that was shown to be able to transfer expression plasmids to mammalian host cells in vitro and in vivo has been more then doubled and has been documented for *S. typhi, S. choleraesuis, Listeria monocytogenes, Yersinia pseudotuberculosis*, and *Y. enterocolitica* (Fennelly et al., 1999; Shiau et al., 2001; Dietrich et al., 1998; Hense et al., 2001; Al-Mariri et al., 2002).

In general, it could be assumed that all bacteria that are able to enter the cytosol of the host cell (like *S. flexneri* or *L. monocytogenes*) and lyse within this cellular compartment, should be able to transfer DNA. This is known as 'abortive' or 'suicidal' invasion as the bacteria have to lyse for the DNA transfer to occur (Grillot-Courvalin et al., 1999). In addition, even many of the bacteria that remain in the phagocytic vacuole (like *S. typhimurium*) may also be able to do so. Thus, recombinant laboratory strains of *E. coli* that have been engineered to be invasive but are unable of phagosomal escape, could deliver their plasmid load to the nucleus of the infected mammalian cell nevertheless (Grillot-Courvalin et al., 1998). Furthermore, *Agrobacterium tumefaciens* has recently also been shown to introduce transgenes into mammalian cells (Kunik et al., 2001).

As used herein, the terms "transfection", "transformation" and variations thereof are generally used interchangeably. "Transfected" or "transformed" cells may have been manipulated to introduce the polynucleotide(s) of interest, or may be progeny cells derived therefrom.

Recombinant Cells

The invention also provides a recombinant eukaryotic cell, for example, a recombinant plant cell, animal cell or fungal cell, which is a host cell transformed with one or more polynucleotides or vectors defined herein, or combination thereof. The term "recombinant cell" is used interchangeably with the term "transgenic cell" herein. Suitable cells of the invention include any cell that can be transformed with a polynucleotide or recombinant vector as defined herein, encoding for example, a polypeptide or dsRNA described herein. The recombinant cell may be a cell in culture, a cell in vitro, or in an organism such as for example, a plant, or in an organ such as, for example, a seed or a leaf. In an embodiment, the eukaryotic cell is a non-human cell.

Host cells into which the polynucleotide(s) are introduced can be either untransformed cells or cells that are already transformed with at least one nucleic acid. Host cells of the present invention either can be endogenously (i.e., naturally) capable of producing polypeptide(s) defined herein, in which case the recombinant cell derived therefrom has an enhanced capability of producing the polypeptide(s), or can be capable of producing said polypeptide(s) only after being transformed with at least one polynucleotide of the invention.

Host cells of the present invention can be any cell capable of producing at least one protein described herein, and include fungal (including yeast), parasite, arthropod, animal, and plant cells. Preferred host cells are yeast, animal and plant cells. In a preferred embodiment, the plant cell is a seed cell, in particular, a cell in a cotyledon or endosperm of a seed. In one embodiment, the cell is an animal cell. The animal cell may be of any type of animal such as, for example, a non-human animal cell, a non-human vertebrate cell, a non-human mammalian cell, or cells of aquatic animals such as fish or crustacea, invertebrates, insects, etc. Non limiting examples of arthropod cells include insect cells such as *Spodoptera frugiperda* (Sf) cells, for example, Sf9, Sf21, *Trichoplusia ni* cells, and *Drosophila* S2 cells.

The host cells may be of an organism suitable for a fermentation process, such as, for example, *Yarrowia lipolytica* or other yeasts.

Transgenic Plants

The invention also provides a plant comprising exogenous polynucleotides as defined herein, a cell of the invention, a DNA construct of the invention, a vector of the invention, or a combination thereof. The term "plant" refers to whole plants, whilst the term "part thereof" refers to plant organs (e.g., leaves, stems, roots, flowers, fruit), single cells (e.g., pollen), seed, seed parts such as an embryo, endosperm, scutellum or seed coat, plant tissue such as vascular tissue, plant cells and progeny of the same. As used herein, plant parts comprise plant cells.

As used herein, the term "plant" is used in it broadest sense. It includes, but is not limited to, any species of grass, ornamental or decorative plant, crop or cereal (e.g., oilseed, maize, soybean), fodder or forage, fruit or vegetable plant, herb plant, woody plant, flower plant, or tree. It is not meant to limit a plant to any particular structure. It also refers to a unicellular plant (e.g., microalga). The term "part thereof" in reference to a plant refers to a plant cell and progeny of same, a plurality of plant cells that are largely differentiated into a colony (e.g., volvox), a structure that is present at any stage of a plant's development, or a plant tissue. Such structures include, but are not limited to, leaves, stems, flowers, fruits, nuts, roots, seed, seed coat, embryos. The term "plant tissue" includes differentiated and undifferentiated tissues of plants including those present in leaves, stems, flowers, fruits, nuts, roots, seed, for example, embryonic tissue, endosperm, dermal tissue (e.g., epidermis, periderm), vascular tissue (e.g., xylem, phloem), or ground tissue (comprising parenchyma, collenchyma, and/or sclerenchyma cells), as well as cells in culture (e.g., single cells, protoplasts, callus, embryos, etc.). Plant tissue may be in planta, in organ culture, tissue culture, or cell culture.

A "transgenic plant", "genetically modified plant" or variations thereof refers to a plant that contains a transgene not found in a wild-type plant of the same species, variety or cultivar. Transgenic plants as defined in the context of the present invention include plants and their progeny which have been genetically modified using recombinant techniques to cause production of at least one polypeptide defined herein in the desired plant or part thereof. The term "transgenic plant parts" has a corresponding meaning.

The terms "seed" and "grain" are used interchangeably herein. "Grain" refers to mature grain such as harvested grain or grain which is still on a plant but ready for harvesting, but can also refer to grain after imbibition or germination, according to the context. Mature grain commonly has a moisture content of less than about 18-20%. "Developing seed" as used herein refers to a seed prior to maturity, typically found in the reproductive structures of the plant after fertilisation or anthesis, but can also refer to such seeds prior to maturity which are isolated from a plant.

As used herein, the term "vegetative tissue" or "vegetative plant part" or variants thereof is any plant tissue, organ or part that does not include the organs for sexual reproduction of plants or the seed bearing organs or the closely associated tissues or organs such as flowers, fruits and seeds. Vegetative tissues and parts include at least plant leaves, stems (including bolts and tillers but excluding the heads), tubers and roots, but excludes flowers, pollen, seed including the seed coat, embryo and endosperm, fruit including mesocarp tissue, seed-bearing pods and seed-bearing heads. In one embodiment, the vegetative part of the plant is an aerial plant part. In another or further embodiment, the vegetative plant part is a green part such as a leaf or stem. Vegetative parts include those parts principally involved in providing or supporting the photosynthetic capacity of the plant or related function, or anchoring the plant.

As used herein, the term "plant storage organ" refers to a part of a plant specialized to store energy in the form of for example, proteins, carbohydrates, lipid. Examples of plant storage organs are seed, fruit, tuberous roots, and tubers. A preferred plant storage organ of the invention is seed.

Plants provided by or contemplated for use in the practice of the present invention include both monocotyledons and dicotyledons. In preferred embodiments, the plants of the present invention are crop plants (for example, cereals and pulses, maize, wheat, potatoes, tapioca, rice, sorghum, millet, cassava, barley, or pea), or other legumes. The plants may be grown for production of edible roots, tubers, leaves, stems, flowers or fruits. The plants may be vegetable or ornamental plants. The plants of the invention may be: corn (*Zea mays*), canola (*Brassica napus, Brassica rapa* ssp.), other Brassicas such as, for example, rutabaga (*Brassica napobrassica*), mustard (*Brassica juncea*), Ethiopian mustard (*Brassica carinata*), crambe (*Crambe abyssinica*), camelina (*Camelina sativa*), sugarbeet (*Beta vulgaris*), clover (*Trifolium* sp.), flax (*Linum usitatissimum*), alfalfa (*Medicago sativa*), rice (*Oryza sativa*), rye (*Secale cerale*), sorghum (*Sorghum bicolor, Sorghum vulgare*), sunflower (*Helianthus annus*), wheat (*Tritium aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Lopmoea batatus*), cassava (*Manihot esculenta*), coffee (*Cofea* spp.), coconut (*Cocos nucifera*), pineapple (*Anana comosus*), citris tree (*Citrus* spp.), cocoa (*Theobroma cacao*), tea (*Camellia senensis*), banana (*Musa* spp.), avocado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Prunus amygdalus*), jatropha (*Jatropha curcas*), lupins, Eucalypts, palm, nut sage, pongamia, oats, or barley.

Other preferred plants include C4 grasses such as *Andropogon gerardi, Bouteloua curtipendula, B. gracilis, Buchloe dactyloides, Panicum virgatum, Schizachyrium scoparium, Miscanthus* species for example, *Miscanthus* x *giganteus* and *Miscanthus sinensis, Sorghastrum nutans, Sporobolus cryptandrus*, Switchgrass (*Panicum virgatum*), sugarcane (*Saccharum officinarum*), Brachyaria; C3 grasses such as *Elymus canadensis*, the legumes *Lespedeza capitata* and *Petalostemum villosum*, the forb *Aster azureus*; and woody plants such as *Quercus ellipsoidalis* and *Q. macrocarpa*.

In a preferred embodiment, the plant is an angiosperm.

In an embodiment, the plant is an oilseed plant, preferably an oilseed crop plant. As used herein, an "oilseed plant" is a plant species used for the commercial production of lipid from the seeds of the plant. The oilseed plant may be oil-seed rape (such as canola), maize, sunflower, safflower, soybean, sorghum, flax (linseed) or sugar beet. Furthermore, the oilseed plant may be other Brassicas, cotton, peanut, poppy, rutabaga, mustard, castor bean, sesame, safflower, or nut producing plants. The plant may produce high levels of lipid in its fruit such as olive, oil palm or coconut. Horticultural plants to which the present invention may be applied are lettuce, endive, or vegetable Brassicas including cabbage, broccoli, or cauliflower. The present invention may be applied in tobacco, cucurbits, carrot, strawberry, tomato, or pepper.

In a preferred embodiment, the transgenic plant is homozygous for each and every gene that has been introduced (transgene) so that its progeny do not segregate for the desired phenotype. The transgenic plant may also be heterozygous for the introduced transgene(s), preferably uniformly heterozygous for the transgene such as for example, in F1 progeny which have been grown from hybrid seed. Such plants may provide advantages such as hybrid vigour, well known in the art.

Transformation of Plants

Transgenic plants can be produced using techniques known in the art, such as those generally described in Slater et al., Plant Biotechnology—The Genetic Manipulation of Plants, Oxford University Press (2003), and Christou and Klee, Handbook of Plant Biotechnology, John Wiley and Sons (2004).

As used herein, the terms "stably transforming", "stably transformed" "integrated" and variations thereof refer to the integration of the polynucleotide into the genome of the cell such that they are transferred to progeny cells during cell division without the need for positively selecting for their presence. Stable transformants, or progeny thereof, can be selected by any means known in the art such as Southern blots on chromosomal DNA, or in situ hybridization of genomic DNA.

*Agrobacterium*-mediated transfer is a widely applicable system for introducing genes into plant cells because DNA can be introduced into cells in whole plant tissues, plant organs, or explants in tissue culture, for either transient expression, or for stable integration of the DNA in the plant cell genome. The use of *Agrobacterium*-mediated plant integrating vectors to introduce DNA into plant cells is well known in the art (see for example, U.S. Pat. Nos. 5,177,010, 5,104,310, 5,004,863, or U.S. Pat. No. 5,159,135). The region of DNA to be transferred is defined by the border sequences, and the intervening DNA (T-DNA) is usually inserted into the plant genome. Further, the integration of the T-DNA is a relatively precise process resulting in few rearrangements. In those plant varieties where *Agrobacterium*-mediated transformation is efficient, it is the method of choice because of the facile and defined nature of the gene transfer. Preferred *Agrobacterium* transformation vectors are capable of replication in *E. coli* as well as *Agrobacterium*, allowing for convenient manipulations as described (Klee et al., In: Plant DNA Infectious Agents, Hohn and Schell, eds., Springer-Verlag, New York, pp. 179-203 (1985)).

Acceleration methods that may be used include for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required. An illustrative embodiment of a method for delivering DNA into *Zea mays* cells by acceleration is a biolistics α-particle delivery system, that can be used to propel particles coated with DNA through a screen such as a stainless steel or Nytex screen, onto a filter surface covered with corn cells cultured in suspension. A particle delivery system suitable for use with the present invention is the helium acceleration PDS-1000/He gun available from Bio-Rad Laboratories.

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein, one may obtain up to 1000 or more foci of cells transiently expressing a marker gene. The number of cells in a focus that express the gene product 48 hours post-bombardment often range from one to ten and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA such as linearized DNA or intact supercoiled plasmids. It is believed that pre-bombardment manipulations are especially important for successful transformation of immature embryos.

In another alternative embodiment, plastids can be stably transformed. Methods disclosed for plastid transformation in higher plants include particle gun delivery of DNA containing a selectable marker and targeting of the DNA to the plastid genome through homologous recombination (U.S. Pat. Nos. 5,451,513, 5,545,818, 5,877,402, 5,932,479, and WO 99/05265).

Accordingly, it is contemplated that one may wish to adjust various aspects of the bombardment parameters in small scale studies to fully optimize the conditions. One may particularly wish to adjust physical parameters such as gap distance, flight distance, tissue distance, and helium pressure. One may also minimize the trauma reduction factors by modifying conditions that influence the physiological state of the recipient cells and that may therefore influence transformation and integration efficiencies. For example, the osmotic state, tissue hydration and the subculture stage, or cell cycle of the recipient cells, may be adjusted for optimum transformation. The execution of other routine adjustments will be known to those of skill in the art in light of the present disclosure.

Transformation of plant protoplasts can be achieved using methods based on calcium phosphate precipitation, polyethylene glycol treatment, electroporation, and combinations of these treatments. Application of these systems to different plant varieties depends upon the ability to regenerate that particular plant strain from protoplasts. Illustrative methods for the regeneration of cereals from protoplasts are described (Fujimura et al., 1985; Toriyama et al., 1986; Abdullah et al., 1986).

Other methods of cell transformation can also be used and include but are not limited to the introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., In: Methods for Plant Molecular Biology, Academic Press, San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polynucleotide is cultivated using methods well known to one skilled in the art.

Methods for transforming dicots, primarily by use of *Agrobacterium tumefaciens*, and obtaining transgenic plants have been published for cotton (U.S. Pat. Nos. 5,004,863, 5,159,135, 5,518,908), soybean (U.S. Pat. Nos. 5,569,834, 5,416,011), *Brassica* (U.S. Pat. No. 5,463,174), peanut (Cheng et al., 1996), and pea (Grant et al., 1995).

Methods for transformation of cereal plants such as wheat and barley for introducing genetic variation into the plant by introduction of an exogenous nucleic acid and for regeneration of plants from protoplasts or immature plant embryos are well known in the art, see for example, CA 2,092,588, AU 61781/94, AU 667939, U.S. Pat. No. 6,100,447, PCT/US97/10621, U.S. Pat. Nos. 5,589,617, 6,541,257, and other methods are set out in WO 99/14314. Preferably, transgenic wheat or barley plants are produced by *Agrobacterium tumefaciens* mediated transformation procedures. Vectors carrying the desired polynucleotide may be introduced into regenerable wheat cells of tissue cultured plants or explants, or suitable plant systems such as protoplasts.

The regenerable wheat cells are preferably from the scutellum of immature embryos, mature embryos, callus derived from these, or the meristematic tissue.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

A transgenic plant formed using *Agrobacterium* or other transformation methods typically contain a single genetic locus on one chromosome. Such transgenic plants can be referred to as being hemizygous for the added gene(s). More preferred is a transgenic plant that is homozygous for the added gene(s), that is, a transgenic plant that contains two added genes, one gene at the same locus on each chromosome of a chromosome pair. A homozygous transgenic plant can be obtained by self-fertilising a hemizygous transgenic plant, germinating some of the seed produced and analyzing the resulting plants for the gene of interest.

It is also to be understood that two different transgenic plants that contain two independently segregating exogenous genes or loci can also be crossed (mated) to produce offspring that contain both sets of genes or loci. Selfing of appropriate F1 progeny can produce plants that are homozygous for both exogenous genes or loci. Back-crossing to a parental plant and out-crossing with a non-transgenic plant are also contemplated, as is vegetative propagation. Descriptions of other breeding methods that are commonly used for different traits and crops can be found in Fehr, In: Breeding Methods for Cultivar Development, Wilcox J. ed., American Society of Agronomy, Madison Wis. (1987).

Polypeptides

The terms "polypeptide" and "protein" are generally used interchangeably.

A polypeptide or class of polypeptides may be defined by the extent of identity (% identity) of its amino acid sequence to a reference amino acid sequence, or by having a greater % identity to one reference amino acid sequence than to another. The % identity of a polypeptide to a reference amino acid sequence is typically determined by GAP analysis (Needleman and Wunsch, 1970; GCG program) with parameters of a gap creation penalty=5, and a gap extension penalty=0.3. The query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns two sequences over their entire length. The polypeptide or class of polypeptides may have the same enzymatic activity as, or a different activity than, or lack the activity of, the reference polypeptide. Preferably, the polypeptide has an enzymatic activity of at least 10% of the activity of the reference polypeptide.

As used herein a "biologically active fragment" is a portion of a polypeptide defined herein which maintains a defined activity of a full-length reference polypeptide for example, silencing suppressor activity. Biologically active fragments as used herein exclude the full-length polypeptide. Biologically active fragments can be any size portion as long as they maintain the defined activity. Preferably, the biologically active fragment maintains at least 10% of the activity of the full length polypeptide.

With regard to a defined polypeptide or enzyme, it will be appreciated that % identity figures higher than those provided herein will encompass preferred embodiments. Thus, where applicable, in light of the minimum % identity figures, it is preferred that the polypeptide/enzyme comprises an amino acid sequence which is at least 40%, more preferably at least 50%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants of the polypeptides defined herein can be prepared by introducing appropriate nucleotide changes into a nucleic acid defined herein, or by in vitro synthesis of the desired polypeptide. Such mutants include for example, deletions, insertions, or substitutions of residues within the amino acid sequence. A combination of deletions, insertions and substitutions can be made to arrive at the final construct, provided that the final polypeptide product possesses the desired characteristics.

Mutant (altered) polypeptides can be prepared using any technique known in the art, for example, using directed evolution or rationale design strategies (see below). Products derived from mutated/altered DNA can readily be screened using techniques described herein to determine if they possess, for example, silencing suppressor activity.

In designing amino acid sequence mutants, the location of the mutation site and the nature of the mutation will depend on characteristic(s) to be modified. The sites for mutation can be modified individually or in series for example, by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide removed and a different residue inserted in its place. The sites of greatest interest for substitutional mutagenesis include sites identified as the active site(s). Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 1 under the heading of "exemplary substitutions".

In a preferred embodiment a mutant/variant polypeptide has only, or not more than, one or two or three or four conservative amino acid changes when compared to a naturally occurring polypeptide. Details of conservative amino acid changes are provided in Table 1. As the skilled person would be aware, such minor changes can reasonably be predicted not to alter the activity of the polypeptide when expressed in a recombinant cell. Furthermore, the skilled person can easily aligned related molecules, such as the V2-like proteins provided as SEQ ID NOs 1 and 38 to 51, to identify suitable variants based on conserved and non-conserved amino acids.

TABLE 1

Exemplary substitutions.

| Original Residue | Exemplary Substitutions |
| --- | --- |
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

Directed Evolution

In directed evolution, random mutagenesis is applied to a protein, and a selection regime is used to pick out variants that have the desired qualities, for example, increased silencing suppressor activity. Further rounds of mutation and selection are then applied. A typical directed evolution strategy involves three steps:

1) Diversification:

The gene encoding the protein of interest is mutated and/or recombined at random to create a large library of gene variants. Variant gene libraries can be constructed through error prone PCR (see, for example, Cadwell and Joyce, 1992), from pools of DNaseI digested fragments prepared from parental templates (Stemmer, 1994a; Stemmer, 1994b; Crameri et al., 1998; Coco et al., 2001) from degenerate oligonucleotides (Ness et al., 2002, Coco, 2002) or from mixtures of both, or even from undigested parental templates (Zhao et al., 1998; Eggert et al., 2005; Jézéquel et al., 2008) and are usually assembled through PCR. Libraries can also be made from parental sequences recombined in vivo or in vitro by either homologous or non-homologous recombination (Ostermeier et al., 1999; Volkov et al., 1999; Sieber et al., 2001). Variant gene libraries can also be constructed by sub-cloning a gene of interest into a suitable vector, transforming the vector into a "mutator" strain such as the *E. coli* XL-1 red (Stratagene) and propagating the transformed bacteria for a suitable number of generations. Variant gene libraries can also be constructed by subjecting the gene of interest to DNA shuffling (i.e., in vitro homologous recombination of pools of selected mutant genes by random fragmentation and reassembly) as broadly described by Harayama (1998).

2) Selection:

The library is tested for the presence of mutants (variants) possessing the desired property using a screen or selection. Screens enable the identification and isolation of high-performing mutants by hand, while selections automatically eliminate all nonfunctional mutants. A screen may involve screening for the presence of known conserved amino acid motifs. Alternatively, or in addition, a screen may involve expressing the mutated polynucleotide in a host organism or part thereof and assaying the level of activity and optionally, expressing the parent (unmutated) polynucleotide. Alternatively, the screen may involve feeding the organism or part thereof labelled substrate and determining the level of substrate or product in the organism or part thereof relative to a corresponding organism or part thereof lacking the mutated polynucleotide and optionally, expressing the parent (unmutated) polynucleotide.

3) Amplification:

The variants identified in the selection or screen are replicated many fold, enabling researchers to sequence their DNA in order to understand what mutations have occurred.

Together, these three steps are termed a "round" of directed evolution. Most experiments will entail more than one round. In these experiments, the "winners" of the previous round are diversified in the next round to create a new library. At the end of the experiment, all evolved protein or polynucleotide mutants are characterized using biochemical methods.

Rational Design

A protein can be designed rationally, on the basis of known information about protein structure and folding. This can be accomplished by design from scratch (de novo design) or by redesign based on native scaffolds (see, for example, Halling a, 1997; and Lu and Berry, Protein Structure Design and Engineering, Handbook of Proteins 2, 1153-1157 (2007)). Protein design typically involves identifying sequences that fold into a given or target structure and can be accomplished using computer models. Computational protein design algorithms search the sequence-conformation space for sequences that are low in energy when folded to the target structure. Computational protein design algorithms use models of protein energetics to evaluate how mutations would affect a protein's structure and function. These energy functions typically include a combination of molecular mechanics, statistical (i.e. knowledge-based), and other empirical terms. Suitable available software includes IPRO (Interative Protein Redesign and Optimization), EGAD (A Genetic Algorithm for Protein Design), Rosetta Design, Sharpen, and Abalone.

Also included within the scope of the invention are polypeptides defined herein which are differentially modified during or after synthesis for example, by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the polypeptide.

Uses

The cells of the invention with an increased level of an RNA of interest and/or amount of protein encoded by the RNA of interest, and a reduced level of target RNA encoded by a first polynucleotide of interest and/or amount of the protein encoded by the target RNA, can have a wide range of desired properties which influence, for example, an agronomic trait, insect resistance, disease resistance, herbicide resistance, sterility, grain characteristics, and the like. The encoded RNAs may be involved in metabolism of oil, starch, carbohydrates, nutrients, etc., or may be responsible for the synthesis of proteins, peptides, fatty acids, lipids, waxes, oils, starches, sugars, carbohydrates, flavors, odors, toxins, carotenoids, hormones, polymers, flavonoids, storage proteins, phenolic acids, alkaloids, lignins, tannins, celluloses, glycoproteins, glycolipids, etc.

In a particular example, the plants produced increased levels of enzymes for oil production in plants such as Brassicas, for example oilseed rape or sunflower, safflower, flax, cotton, soybean or maize; enzymes involved in starch synthesis in plants such as potato, maize, and cereals such as wheat barley or rice; enzymes which synthesize, or proteins which are themselves, natural medicaments, such as pharmaceuticals or veterinary products.

Types of polypeptides that are contemplated for production in a cell of the present invention include pharmaceutical proteins for use in mammals, including man, such as insulin, preproinsulin, proinsulin, glucagon, interferons such as α-interferon and γ-interferon, blood-clotting factors such as Factor VII, VIII, IX, X, XI, and XII, fertility hormones such as luteinising hormone, follicle stimulating hormone growth factors such as epidermal growth factor, platelet-derived growth factor, granulocyte colony stimulating factor, prolactin, oxytocin, thyroid stimulating hormone, adrenocorticotropic hormone, calcitonin, parathyroid hormone, somatostatin, erythropoietin (EPO), enzymes such as β-glucocerebrosidase, haemoglobin, serum albumin, collagen, growth hormone, human serum albumin, human-secreted alkaline phosphatase, aprotinin, α1-antitrypsin, IgG1 (phosphonate ester), IgM (neuropeptide hapten), SIgA/G (*Streptococcus mutans* adhesin), scFv-bryodin 1 immunotoxin (CD 40), IgG (HSV), LSC(HSV) and the like.

Furthermore, the cells of the invention can be used for the production of specific antibodies, including antibody-related molecules or active fragments thereof which bind, for example, bone morphogenetic protein receptor-type IB; E16; STEAP1; MPF; Napi3b; Sema 5b; PSCA; Endothelin type B receptor; MSG783; STEAP2; TrpM4; CRIPTO; CD21; CD79b; FcRH2; HER2; NCA; MDP; IL20Ra; Brevican; EphB2R; ASLG659; PSCA; GEDA; B cell-activating factor receptor; CD22; CD79a; CXCR5; HLA-DOB; P2x5; CD72; LY64; FcRH1; IRTA2; TENB2; CD20; VEGF including VEGF_A, B, C or D; p53; EGFR; progesterone receptor; cathepsin D; Bc1-2; E cadherin; CEA; Lewis X; Ki67; PCNA; CD3; CD4; CD5; CD7; CD11c; CD11d; c-Myc; tau; PrPSC; or Aβ.

In addition, the cells of the invention can be used for the production of an antigen, which may or may not be delivered by consumption of the storage organ, examples of which include Hepatitis B virus envelope protein, rabies virus glycoprotein, *Escherichia coli* heat-labile entertoxin, Norwalk virus capsid protein, diabetes autoantigen, cholera toxin B subunit, cholera toxin B and A2 subunits, rotavirus entertoxin and enterotoxigenic *E. coli* fimbrial antigen fusions, porcine transmissible gastroenteritis virus glycoprotein S, human rhinovirus 15 (HRV-14) and human immunodeficiency virus type (HIV-1) epitopes, Mink Enteritis Virus epitopes, foot and mouth disease virus VP1 structural protein, human cytomegalovirus glycoprotein B, dental caries (*S. mutans*) antigens, and respiratory syncytial virus antigens.

In an embodiment, the target RNA encodes a polypeptide other than a protein having sn-2 glycerol-3-phosphate acyltransferase (GPAT) activity and/or the RNA of interest encodes a polypeptide other than a protein having monoacylglycerol acyltransferase (MGAT) activity. In an embodiment, the eukaryotic cell is a cell other than an *Arabidopsis thaliana* cell.

EXAMPLES

Example 1

General Materials and Methods

Expression of Genes in Plant Cells in a Transient Expression System

Genes were expressed in plant cells using a transient expression system essentially as described by Voinnet et al. (2003) and Wood et al. (2009). Chimeric binary vectors, 35S:p19 and 35S:V2, for expression of the p19 and V2 viral silencing suppressors, respectively, were separately introduced into *Agrobacterium tumefaciens* strain GV3101:mp90. All other binary vectors containing a coding region to be expressed by a promoter, such as the strong constitutive CaMV 35S promoter, were introduced into *Agrobacterium tumefaciens* strain AGL1. The recombinant cells were grown to stationary phase at 28° C. in LB broth supplemented with 50 mg/L rifampicin and either 50 mg/L kanamycin or 80 mg/L spectinomycin according to the selectable marker gene on the binary vector. Acetosyringone (100 μM) was added to the bacterial cultures and growth continued a further 2 hours for the induction of virulence factors. The bacteria were pelleted by centrifugation at 3000 g for 5 min at room temperature before being resuspended to OD600=2.0 in infiltration buffer containing 10 mM MES pH 5.7, 10 mM $MgCl_2$ and 100 μM acetosyringone. The cells were then incubated at 28° C. with shaking for another 30 minutes and a volume of each culture required to reach a final concentration of OD600=0.3 added to a fresh tube. Mixed cultures comprising genes to be expressed included either of the 35S:p19 or 35S:V2 constructs in *Agrobacterium* unless otherwise stated. The final volume was made up with the infiltration buffer.

Leaves were then infiltrated with the culture mixture and the plants were typically grown for a further three to five days after infiltration before leaf discs were recovered for total lipid isolation. Time courses of GFP expression were conducted on the intact leaves from the first day after infiltration through to 7 days post-infiltration (dpi). *N. benthamiana* plants were grown in growth cabinets under a constant 24° C. with a 14/10 light/dark cycle with a light intensity of approximately 200 lux using Osram 'Soft White' fluorescent lighting placed directly over plants. Typically, 6 week old plants were used for experiments and true leaves that were nearly fully-expanded were infiltrated. All non-infiltrated leaves were removed by post infiltration to avoid shading.

Lipid Analysis

Total Lipid Isolation and Fractionation

Tissue samples were freeze-dried, weighed and total lipids extracted from samples of approximately 30 mg dry weight as described by Bligh and Dyer (1959). When required, TAG fractions were separated from other lipid components using a 2-phase thin-layer chromatography (TLC) system on pre-coated silica gel plates (Silica gel 60, Merck). An extracted lipid sample equivalent to 10 mg dry weight of leaf tissue was chromatographed in a first phase with hexane/diethyl ether (98/2 v/v) to remove non-polar waxes and then in a second phase using hexane/diethyl ether/acetic acid (70/30/1 v/v/v). When required, polar lipids were separated from non-polar lipids in lipid samples extracted from an equivalent of 5 mg dry weight of leaves using two-dimensional TLC (Silica gel 60, Merck), using chloroform/methanol/water (65/25/4 v/v/v) for the first direction and chloroform/methanol/$NH_4OH$/ethylpropylamine (130/70/10/1 v/v/v/v) for the second direction. The lipid spots, and appropriate standards run on the same TLC plates, were visualized by brief exposure to iodine vapour, collected into vials and transmethylated to produce FAME for GC analysis as follows.

Conversion of Fatty Acids to FAMEs

For total lipid analysis, with the exception of the analysis of DHS content, lipid extracted from an equivalent of 10 mg of dry weight leaf material was transmethylated using a solution of methanol/HCl/dichloromethane (10/1/1 v/v/v) at 80° C. for 2 hr to produce fatty acid methyl esters (FAME). For analysis of DHS in leaves, samples were transmethylated using the same reagents but with milder conditions, namely for 10 mins at 50° C., using DHS (Larodan Chemicals) as a calibration standard. The FAME were extracted into hexane, concentrated to near dryness under a stream of $N_2$ gas and quickly reconstituted in hexane prior to analysis by GC.

DHS and eDHS were determined in total lipid samples by the following method. Samples were directly treated with 0.1M sodium methoxide in methanol/chloroform (10:1) in a sealed test tube with heating at 90° C. for 60 mins to convert lipids to FAMEs. When cool, the solution was slightly acidified to pH 6-7 with acetic acid. Saline and hexane/chloroform (4:1 v/v) were added with vigorous shaking, and the hexane/chloroform layer containing FAMEs was transferred to a vial for analysis.

Capillary Gas-Liquid Chromatography (GC)

FAMEs were analysed by gas chromatography (GC) using an Agilent Technologies 6890N gas chromatograph (Palo Alto, Calif., USA) equipped with an Equity™-1 fused silica capillary column (15 m×0.1 mm i.d., 0.1 μm film thickness), an FID, a split/splitless injector and an Agilent Technologies 7683 Series auto sampler and injector. Helium was used as the carrier gas. Samples were injected in splitless mode at an oven temperature of 120° C. After injection, the oven temperature was raised to 201° C. at 10° C.min$^{-1}$ and then to 270° C. at 5° C.min$^{-1}$ and held for 20 min. Peaks were quantified with Agilent Technologies ChemStation software (Rev B.03.01 (317), Palo Alto, Calif., USA). Peak responses were similar for the fatty acids of authentic Nu-Check GLC standard-411 (Nu-Check Prep Inc, MN, USA) which contained equal proportions of 31 different fatty acid methyl esters, including 18:1, 18:0, 20:0 and 22:0. Slight variations of peak responses among peaks were balanced by multiplying the peak areas by normalization factors of each peak. The proportion of each fatty acid in total fatty acids of samples was calculated on the basis of individual and total peaks areas for the fatty acids.

Analysis of FAMEs by Gas Chromatography-Mass Spectrometry

Analysis of FAMEs by gas chromatography-mass spectrometry (GCMS) was conducted using a Varian 3800 equipped with a BPX70 capillary column (length 30 m, i.d. 0.32 mm, film thickness 0.25 µm, Phenomenex). Injections were made in the split mode using helium as the carrier gas and an initial column temperature of 60° C. raised at 20° C.min$^{-1}$ until 180° C., then raised at 2.5° C.min$^{-1}$ until 190° C., then raised at 25° C.min$^{-1}$ until 260° C. and held for 2.2 min. Mass spectra were acquired under positive electron impact in full scan mode between 40-400 amu at the rate of 2 scans per second using a Varian 1200 Single Quadrupole mass spectrometer. The mass spectra corresponding to each peak in the chromatogram was automatically compared with spectra of pure standards. Test spectra that matched standard spectra with a high degree of accuracy and eluted at the same time as an authentic standard or eluted at a plausible retention time, were identified. FAMEs were quantified by peak area integration using Varian software and assuming equivalent MS response factors on a weight basis.

Quantification of TAG Via Iatroscan

One µl of each leaf extract was loaded on one Chromarod-SII for TLC-FID Iatroscan™ (Mitsubishi Chemical Medience Corporation—Japan). The Chromarod rack was then transferred into an equilibrated developing tank containing 70 ml of a Hexane/CHCl$_3$/2-Propanol/Formic acid (85/10.716/0.567/0.0567 v/v/v/v) solvent system. After 30 min of incubation, the Chromarod rack was then dried for 3 min at 100° C. and immediately scanned on an Iatroscan MK-6s TLC-FID analyser (Mitsubishi Chemical Medience Corporation—Japan). Peak areas of DAGE internal standard and TAG were integrated using SIC-48011 integration software (Version:7.0-E SIC System instruments Co., LTD—Japan).

TAG quantification was carried out in two steps. First, DAGE was scanned in all samples to correct the extraction yields after which concentrated TAG samples were selected and diluted. Next, TAG was quantified in diluted samples with a second scan according to the external calibration using glyceryl trilinoleate as external standard (Sigma-Aldrich).

Transformation of *Arabidopsis thaliana*

Chimeric vectors comprising genes to be used to transform *Arabidopsis* were introduced into *A. tumefaciens* strain AGL1 and cells from culture of the transformed *Agrobacterium* used to treat *A. thaliana* (ecotype Columbia) plants using the floral dip method for transformation (Clough and Bent, 1998).

Example 2

V2 Protein Acts as a Silencing Suppressor in Transient Assays

Construction of Chimeric Genes for Expression of Silencing Suppressors p19 or V2

The p19 protein from Tomato Bushy Stunt Virus (TBSV) (SEQ ID NO: 2) and the V2 protein from Tomato Yellow Leaf Roll Virus (TYLRV) (SEQ ID NO: 1) have been characterised as viral suppressor proteins (VSP), functioning as silencing suppressors (Voinnet et al., 2003; Glick et al., 2008). p19 binds to 21 nucleotide long siRNAs before they guide Argonaute-guided cleavage of homologous RNA (Ye et al., 2003). V2 is an another silencing suppressor that disrupts the function of the plant protein SGS3, a protein thought to be involved in the production of double stranded RNA intermediates from ssRNA substrates (Elmayan et al., 1998; Mourrain et al., 2000; Beclin et al., 2002) either by directly binding to SGS3 (Glick et al., 2008) or by binding dsRNA intermediates that contain a 5' overhang structure and competitively excluding SGS3 from binding these intermediates (Fukunaga and Doudna, 2009).

A DNA sequence encoding p19 (SEQ ID NO: 4), based on the genome sequence of the Tomato Bushy Stunt Virus (Hillman et al., 1989) was chemically synthesised, including an NcoI site spanning the translation start ATG codon. The DNA sequence was amplified by PCR and inserted into the pENTR/D-TOPO vector (Invitrogen), producing a plasmid designated pCWO87 (pENTR-p19). Gateway LR clonase reactions were then used to introduce the p19 coding sequence into plant binary vectors under the control of either the CaMV35S promoter, generating a construct designated pCW195 (35S-p19), or the truncated napin promoter FP1, generating pCWO82 (FP1-p19). In addition, the entire FP1-p19-ocs3' expression cassette from pCWO82 was PCR amplified with SacI flanking sites and ligated into pCW141, a plant expression vector having a FP1-GFP gene as a screenable/selectable seed marker, thus generating a plasmid designated pCW164 (FP1-p19 and FP1-GFP). The presence of the FP1-GFP gene allowed the non-destructive identification and selection of transformed T1 seeds in mixed null/T1 populations that resulted from the dipping techniques used to transform *Arabidopsis*.

A DNA sequence encoding V2 (SEQ ID NO: 3), based on the Tomato Yellow Leaf Curl Virus genome sequence (Glick et al., 2008), was chemically synthesised, included flanking NotI and AscI restriction sites to allow direct cloning into the pENTR/D-TOPO vector (Invitrogen), generating a plasmid designated pCW192 (pENTR-V2). Gateway LR clonase reactions were used to introduce the V2 gene into plant binary vectors under the control of the 35S promoter (pCW197; 35S-V2) or for seed-specific expression under the control of the truncated napin promoter, FP1 (pCW195; FP1-V2).

The vector pUQ214 described in Brosnan et al. (2007) and comprising a 35S-GFP gene, was used as an example of a target gene, expressing GFP under the control of the 35S promoter. This binary vector included a kanamycin resistance marker gene that can be used for selection of transformed cells in plants if desired.

Function of the Suppressors in Plant Cells

In order to confirm the function of the V2 and p19 proteins as suppressors of silencing and therefore increasing transgene expression, *Agrobacterium* cells containing either of the 35S-driven VSP constructs were co-infiltrated together with 35 *Agrobacterium* cells containing pUQ214 into *Nicotiana benthamiana* leaves as follows. Transformants of *Agrobacterium tumefaciens* strains separately harbouring each binary vector were grown overnight at 28° C. in LB broth supplemented with antibiotics (50 mg/L kanamycin or 80 mg/L spectinomycin, dependent on the selectable marker gene used) and rifampicin. Turbid cultures were supplemented with 100 µM acetosyringone and grown for a further 2 hours. Cultures were centrifuged (4000×g for min at room temperature) to harvest the cells and the cell pellets gently resuspended in infiltration buffer (5 mM MES, 5 mM $MgSO_4$, pH 5.7, 100 µM acetosyringone) to an optical density of about 2.0. Cell suspensions for infiltration were prepared, combining different transformants as required, so that each *Agrobacterium* strain was present at an $OD_{600\ nm}$ of 0.3. The cell suspensions were infiltrated into the underside of fully-expanded leaves of 5-6 week old *N. benthamiana* plants using a 1 mL syringe without a needle, using gentle pressure. By these means, the cell suspensions entered primarily through the stomates and infiltrated the mesophyll cell layer of the leaves. Infiltrated areas of leaves, indicated by the water-soaked region and commonly 3 to 4 cm in diameter, were circled by a permanent marker. Plants were housed in a 24° C. plant growth room with 14:10 light:dark cycle, where the light intensity was 400-500 $\mu Einsteins.m^{-2}.s^{-1}$ at the leaf surface provided by overhead fluorescent lighting (Philips TLD 35S/865 'Cold Daylight'). Under these conditions, the *Agrobacteria* efficiently transferred the T-DNAs into the *N. benthamiana* cells.

GFP expression in the leaves was measured daily from 1-7 days after the infiltrations by measuring the fluorescence under UV light. GFP images were captured on a digital SLR (Nikon D60; 55-200 mm lens) using the NightSea fluorescent light and filter set (NightSea, Bedford, Mass., USA). Infiltrated leaves were generally left on the plant and were photographed every day from 2-7 days post infiltration, thereby a time-course of GFP expression could be determined for the same set of infiltrations. Representative fluorescence photographs are shown in FIG. 1.

The 35S:GFP construct introduced in the absence of a VSP produced a relatively low level of fluorescence, indicative of GFP expression, peaking after 2-3 days and reducing thereafter. In contrast, when the GFP construct was co-infiltrated with either the p19 or the V2 suppressor constructs, both the intensity and duration of fluorescence were greatly increased, extending to and maintained beyond more than 7 days post infiltration. These observations indicated enhanced expression of the $^{35}S$: GFP gene in the leaf assays in the presence of the VSPs, and confirmed their function as potent suppressor proteins that inhibited the endogenous co-suppression pathways in the plant cells.

Measurement of GFP Expression by Western Blot Analysis

GFP expression was also analysed by Western blot using a GFP specific antibody as follows. 1 $cm^2$ leaf samples were removed from the infiltrated zones and subjected to denaturing protein extraction, polyacrylamide gel electrophoresis (PAGE; 12% gel) and blotting to PVDF membrane essentially as described (Helliwell et al., 2006). GFP protein was detected using an anti-GFP monoclonal antibody (1:10000 dilution, Clontech) and goat anti-mouse HRP (1:5000 dilution, Promega) according to the suppliers instructions. Coomassie blue staining of high molecular proteins remaining in gels after the transfer to PVDF membranes was used to confirm equal protein loading between samples. Protein size was determined using the Pre-Stained PageRuler Protein Ladder (MBI-Fermentas P7711S).

The results of the Western blot analyses confirmed the fluorescence data, confirming the function of both p19 and V2 as silencing suppressors (FIG. 2).

Example 3

RNAi Gene Silencing can Occur Simultaneously with Silencing Suppression

Hairpin RNAi Constructs Targeting GFP

A binary construct pUQ218 (Brosnan et al., 2007), containing both a 35S-GFP gene and a 35S-hairpin encoding region targeted against GFP and within the same T-DNA region, was used when experiments used both GFP expression and simultaneous GFP silencing activities in the same cell. The hairpin RNA comprised the first 380 bp of the GFP coding sequence, corresponding to nucleotides 1 to 380 of Accession No. U43284. A hpGFP binary construct without the 35S-GFP gene was generated by removing the 35S-GFP component via a NheI-AvrII digestion/religation reaction, creating pCW445 (35S-hpGFP).

Co-Expression of Silencing Suppressors and Silencing Constructs with Transgene Expression The VSPs, V2 and p19, were compared in combination with GFP expression from the 35S-GFP gene and a hairpin targeting GFP (hpGFP) to silence the 35S-GFP gene, using transient assays by infiltration of the genes from *Agrobacterium* into *N. benthamiana* leaves. These were compared to control infiltrations without the hpGFP, into adjacent spots on the same leaf at the same time, to determine expression levels in the absence of the hairpin RNA. FIG. 1, panel B, shows representative photographs of the fluorescence observed from 2 to 7 days post infiltration. The combination of pCW195 (35S-p19) and pUQ218 (containing both GFP and hpGFP) resulted in high levels of GFP expression, indicating that p19 effectively suppressed silencing by the hairpin RNA of the GFP transgene. In contrast, combinations of V2, 35S-GFP and hpGFP resulted in a near-total silencing of GFP. Complete silencing of GFP was achieved with hpGFP in the absence of any VSP.

Experiments using pUQ218 generated equivalent results for GFP expression compared to the combination of separate vectors pUQ214 (35S-GFP) and pCW557 (35S-hpGFP). This indicated that the hairpin RNA construct was efficiently introduced into cells via *Agrobacterium* in the experiments described above, and that it was not necessary to link the target gene and the silencing gene on a single construct in the transient leaf assays.

Western blots of GFP protein levels (FIG. 2) using a specific antibody as in Example 2 confirmed that the co-introduction of p19 suppressed the silencing activity of hpGFP, thereby allowing strong GFP expression. In contrast, only a low level of GFP expression was detected when the combination of V2, GFP and hpGFP was introduced. This great difference between p19 and V2 with respect to suppressing the function of a hairpin RNA indicated that V2 may allow strong over-expression of transgenes simultaneously with hairpin-based RNAi strategies in the same cell.

Example 4

Silencing of an Endogenous Gene in the Presence of Silencing Suppressors

In order to test whether an endogenous gene could be silenced simultaneously with expression of a silencing suppressor, a hairpin RNA construct was designed and made which would silence a FAD2 gene in *N. benthamiana* plants (NbFAD2) (SEQ ID NO: 11). FAD2 is a membrane-bound enzyme located on the endoplasmic reticulum (ER) which desaturates 18:1 esterified on phosphatidylcholine (18:1-PC) to form 18:2-PC. Activity of FAD2 can readily be assayed by analysing the fatty acid composition of lipid in the plant tissues and determining the ratio of 18:1 (oleic acid) to 18:2 (linoleic acid) in the total fatty acid. FAD2 is active in leaves of *N. benthamiana* as in other plants, resulting in low levels of 18:1-PC in the leaves. As 18:1-PC is an important metabolite for a range of alternative fatty acids metabolic pathways, a chimeric gene was made which included an inverted repeat of a 660 basepair region of NbFAD2 (SEQ ID NO: 12), corresponding to central portion of the endogenous 1151 bp transcript, to silence NbFAD2 as follows.

Construction of Hairpin Construct Targeting NbFAD2

A 660 bp fragment of NbFAD2 was generated by RT-PCR from leaf total RNA using primers designed against conserved regions of a *Nicotianum tabacum* FAD2 sequence in the Solgenomics database (SGN-U427167), namely forward primer NbFAD2F1 5'-TCATTGCGCACGAATGTGGC-CACCAT-3' (+451 bp co-ordinates) (SEQ ID NO: 13) and reverse primer NbFAD2R15'-CGAGAACAGATGGTG-CACGACG-3' (+1112 bp co-ordinates) (SEQ ID NO: 14). Total RNA was isolated from young *N. benthamiana* leaves using a Trizol-based method (Invitrogen and associated literature). A Platinum Taq One-Step RT-PCR reaction (Invitrogen) was performed using the cycling conditions of 50° C. (10 min), 94° C. (2 min) and 30 cycles of 50° C. (30 s)/72° C. (60 s)/92° C. (30s) and a final 72° C. (2 min). The NbFAD2 gene fragment was subsequently ligated into pENTR11 and recombined using standard Gateway procedures into the pHellsgate8 vector (Helliwell et al., 2002) to generate the plasmid designated pFN033. This construct had an inverted repeat of the 660 bp fragment under the control of the 35S promoter, thereby producing, upon transcription, a RNA hairpin directed against NbFAD2, hereafter named hpNbFAD2.

hpNbFAD2 was transformed into *Agrobacterium tumefaciens* strain AGL1 and infiltrated into *N. benthamiana* leaves in combination with *Agrobacteria* containing the 35S:V2 or 35S:p19 constructs. Five days post infiltration, infiltrated zones from leaves were sampled, total lipid extracted and the PC fraction analysed. The fatty acid analysis of the PC fraction of leaves infiltrated with combinations of hpNb-FAD2 and V2 showed a substantial increase in the 18:1-PC content from 9% 18:1-PC to 39% 18:1-PC (FIG. 3). These percentages were based on the observed amounts of 18:1, 18:2 and 18:3 found on the PC fraction and expressed as a percentage of the sum of these three fatty acids. In comparison, the combination of p19 and hpNbFAD2 resulted in partial silencing of FAD2 activity, reflected in an increase from 8% 18:1-PC to 25% 18:1-PC, a result indicating that hpNbFAD2 could silence the endogenous FAD2 gene to a moderate extent in the presence of co-expression of p19. Previous work has shown that leaf cells infiltrated with a combination of *Agrobacteria* strains, each containing a separate vector, received at least one or more copies of T-DNA from each vector (Wood et al., 2009). This gave us confidence that the great majority of cells in the leaf assays described above had received and expressed both the hairpin and the suppressor encoding genes.

The increase in 18:1-PC levels was reflected in a reduction in the 18:2-PC content in the cells. In contrast, the 18:3-PC levels nearly the same, presumably due to the large amount of 18:3 generated in the FAD2-independent pathways found in the chloroplasts of leaves.

To establish that the suppressor and hairpin constructs were introduced into the same cells efficiently, constructs were also made and tested which co-located the genes within the same T-DNA constructs, thus generating single T-DNAs with 35S-p19+35S-hpNbFAD2 and 35S-V2+35S-NbFAD2 gene combinations. The entire 35S-p19-ocs3' region of pCW194 was PCR amplified using the primers including MluI flanking sites, (underlined) namely Forward primer 5' aacgcgttcgacgaattaattccaatcccaca-3' (SEQ ID NO: 15) and the OCS'3 Reverse primer 5'-ACGCGTCTGCTGAGCCTCGACATGTT-3' (SEQ ID NO: 16). The amplified fragment was ligated into the unique MluI site within pFN033 to create pCW701, containing 35S-p19+35S-hpNbFAD2. Using the same primers, the entire 35S-V2-ocs3' region of pCW197 was PCR amplified and this amplicon was ligated into the unique MluI site of pFN033 to create pCW702, containing 35S-p19+35S-hpNbFAD2. These vectors having the suppressor and hairpin encoding genes located within the same T-DNA region were transformed into *Agrobacterium* strain AGL1 and infiltrated into *N. benthamiana* leaves as before. Leaf tissues were sampled 5 dpi and the PC lipid fractions analysed for the 18:1, 18:2 and 18:3 levels. The results were indistinguishable compared to the results obtained using genes introduced on separate vectors, the inventors concluded that essentially all of the transformable leaf cells in transient leaf assays received at least one copy of each T-DNA in the infiltration mixtures.

Simultaneous Silencing of One Gene while Overexpressing a Second Gene

To test whether additional genes could be over-expressed with the aid of a silencing suppressor while silencing the endogenous FAD2 gene, additional constructs were made for over-expression of genes encoding DGAT1 and oleosin in plant cells. All plant cells possess active lipid pathways producing lipid classes such as DAG and acyl-CoA (Ohlrogge and Browse, 1995), however the esterification of these substrates via DGAT to produce TAG only occurs at significant levels in specialised organs, such as oilseeds and pollen. The ectopic expression of AtDGAT1 in leaves has been shown to generate increased levels of oils (Bouvier-Nave et al., 2000). Previous studies have also shown that AtDGAT1 has some substrate specificity for 18:1 and its elongation product, 20:1 (Katavic et al., 1995). Oleosins are amphipathic proteins whose properties position these proteins on oil/hydrophilic interfaces, thereby creating a coating surrounding oil droplets and forming so called 'oil bodies' in oil-generating tissues (Tzen et al., 1992). 'Oil bodies' are considered a long term storage organelle as the oleosin layer protects the TAG from catabolic processes such as TAG lipases. Seeds of *Arabidopsis* mutants lacking a functional oleosin, ole1, have significantly reduced 18:1 contents and this 18:1 content was restored upon ectopic expression of an oleosin encoding gene from sesame (Scott et al., 2010).

Synthesis and Use of Constructs to Overexpress DGAT1 and Oleosin

The coding region of the AtDGAT1 gene (SEQ ID NO: 10) was cloned from *Arabidopsis* Col-0 mRNA collected from developing embryos using primers based on the Accession No. NG_127503. The amplicon was cloned into pENTR11 (Invitrogen) and recombined via an LR clonase reaction into a 35S binary expression vector to create 35S-AtDGAT1. The oleosin construct was used as described by Scott et al. (2010). This construct had a 35S promoter driving an oleosin coding region (SEQ ID NO: 6) isolated from sesame, encoding the protein with the amino acid sequence of Accession No AF091840 (SEQ ID NO: 5), generating the construct designated 35S-Oleosin.

Combinations of Agrobacterial strains separately containing vectors for transfer of genes encoding DGAT1, oleosin and p19 or V2 and in addition hpNbFAD2 were tested in *N. benthamiana* leaves and the oil content and fatty acid composition in the infiltrated tissues were analysed. Leaf samples were removed 5 dpi and freeze dried overnight. Lipids were extracted from samples of about 30 mg dry weight using the method of Bligh and Dyer (1959). TAGs in the extracted lipids were separated from polar lipids using a 2-phase TLC system on pre-coated silica gel plates (Silica gel 60, Merck). A lipid sample equivalent to 10 mg dry weight of leaf tissue was first run with hexane/diethyl ether (98/2 by vol.) to remove very non-polar waxes and a second phase was run using hexane/diethyl ether/acetic acid (70/30/1 by vol.). The lipid spots, and appropriate standards, were visualized by brief exposures to iodine vapour, collected into vials and transmethylated to produce FAME for GC analysis as described in Example 1. The data are shown in FIG. 4.

Leaves infiltrated with the genes encoding V2 and both DGAT1 and Oleosin had an approximately 5 to 6 fold increase in the TAG content. Moreover, there was a doubling of the 18:1 level calculated as a percentage of the total fatty acids in the TAG fraction, indicating that the combination of these two genes in the presence of the silencing suppressor enhanced the formation (synthesis and accumulation) of leaf oils with increased levels of oleic acid. The further addition of the silencing construct hpNbFAD2 increased the 18:1 level in the leaf oil to either 44% when using V2 or to 35% using p19 as the VSP. This assay configuration confirmed that both V2 and p19 allowed over-expression of transgenes, e.g. encoding AtDGAT1 and Oleosin. Although both silencing suppressors allowed effective simultaneous endogenous FAD2 silencing, use of V2 provided a greater extent of silencing than p19. From the efficiency of the 18:1 accumulation in TAGs, these observations were consistent with the conclusion above that over-expression of the transgenes aided by the VSPs was occurring simultaneously in the same cells as the FAD2 silencing.

In a further experiment to demonstrate that additional genes could be over-expressed with the aid of a silencing suppressor while simultaneously reducing expression of a second gene with a hairpin RNA, a construct was made to express a FAE1 enzyme (SEQ ID NO: 7). FAE1 is an enzyme that elongates saturated and monounsaturated fatty acids esterified to CoA by adding 2 carbons to the acyl chain at the carboxyl end of the fatty acid molecule (James et al., 1995). Previous studies have shown that ectopic expression of AtFAE1 resulted in production of a range of new elongated fatty acids, including a series of so-called very-long chain fatty acids (VLCFA) due to the sequential activity of AtFAE1 in cycles of elongation. The enzyme uses acyl-CoA substrates (Millar et al., 1998).

Synthesis of Construct to Express FAE1

The coding region of AtFAE1, TAIR Accession number 2139599, was chemically synthesised, subcloned into pGEMT-Easy and subcloned via the EcoRI flanking sites into the pENTR cloning vector, pCW306, to include the AttL1 and AttL2 sites, to generate pCW327. A catalase-1 intron, from the castor bean catalase-1 gene, was ligated into the unique NotI site just upstream of the AtFAE1 ORF to generate pCW465, pENTR-intron-AtFAE1. LR clonase reactions were used to recombine the intron-AtFAE1 fragment (SEQ ID NO: 8) into a 35S expression vector, generating pCW483 (35S-intron-AtFAE1). pCW483 was transformed into *Agrobacterium* strain AGL1 and transiently expressed in *N. benthamiana* leaves as above in combination with the other genes. A range of new elongation products were found in leaves expressing AtFAE1, including a significant number of VLCFA such as 20:1 (FIG. 11). Based on the known substrate specificity of AtFAE1, we reasoned that 18:1-CoA would be a preferred substrate for AtFAE1, however this substrate would only be found wild-type leaves at low levels due to the activity of NbFAD2. The inventors therefore combined the over-expression of AtFAE1 with hairpin based silencing of NbFAD2 in the presence of the silencing suppressor V2.

These experiments demonstrated that silencing suppressors such as V2 allowed over-expression of transgenes and the simultaneous silencing of endogenous genes in the same cell, and allowed an optimised substrate pool to be formed for metabolic engineering of fatty acids, e.g. 20:1 and other VLCFA.

Example 5

Small RNA Analysis of Hairpin-Based Silencing of an Endogene

Hairpin-based RNAi constructs are known to generate populations of small RNAs homologous to the hairpin, generally known as primary sRNA molecules. These primary sRNAs can trigger the production of secondary sRNAs that are homologous to regions in the target RNA outside of the hairpin-targeted region. Such sRNAs are mostly 21, 22 or 24 nucleotides in length, reflecting their biogenesis via a several pathways using different Dicer proteins. Each length may have specific functions in transcriptional gene silencing (TGS) and post-transcriptional gene silencing (PTGS). With the availability of deep sequencing technologies, the inventors investigated the small RNA populations arising from hairpin-based gene silencing of the endogenous NbFAD2 gene by the hpNbFAD2 in the transient assays, as above.

Cloning of Full-Length Open-Reading Frame of the NbFAD2 Gene

First of all, the full length open reading frame of the FAD2 gene from *N. benthamiana* was sequenced as follows. Genomic DNA was isolated from 20 g fresh weight of *N. benthamiana* leaves using a method that reduced chloroplastic and mitochondrial DNA contamination (Peterson et al., 1997). High molecular weight DNA was randomly sheared into fragments of approximately 500 bp and ligated with TruSeq library adaptors to generate a gDNA library. This library was sequenced on the HiSeq2000 platform on a complete flowcell. High quality sequences were retained to generate an alignment against the 660 bp hpNbFAD2 fragment (pFN033) using BowTie software. The full-length coding region of NbFAD2 was subsequently cloned via high fidelity PCR using primers Forward 5'-TTT ATGGGAGCTGGTGGTAATATGT-3' (SEQ ID NO: 17) and Reverse 5'-CCC TCAGAATTTGTTTTTGTACCAGAAA-3' (SEQ ID NO: 18) (start and stop codons underlined) and sequence verified using BigDye3.1 sequencing techniques.

Small RNA Analysis

Deep sequencing methods were then used to analyse the populations of sRNA generated from the hairpin RNAi silencing construct, hpNbFAD2, in leaves co-infiltrated with the construct encoding V2. Total RNA was isolated from leaves 5 dpi using Trizol reagent (Invitrogen) according to the suppliers instructions. Small RNAs (15-40 nt size range) were purified via gel electrophoresis and analysed on an Illumina GAxII machine according to the manufacturers protocols.

Small RNAs having a sequence with identity to the NbFAD2 gene were identified and collated. The observed predominant sRNA size classes (20-24 nt) showed a non-uniform distribution across both the forward and reverse strands of the 660 bp target sequence (FIG. 8). Alignments of the small RNA reads against the full-length NbFAD2 open-reading frame sequence indicated that all of the observed sRNAs with homology to NbFAD2 had identity with the region used to generate the hairpin construct, none to the non-targeted regions. Therefore, we concluded that the combination of the V2 silencing suppressor and hpNbFAD2 did not generate secondary sRNAs at an observable frequency. The absolute numbers of sRNA size classes showed that 20, 21, 22, 23 and 24 nt sRNA represented 10%, 44%, 36%, 4% and 10% of all sRNA, respectively (FIG. 9). This result confirmed that hairpins generated primary sRNAs against an endogenous gene and not secondary sRNAs, although we could not exclude an influence of the V2 suppressor in this result.

Example 6

Engineering a Transgenic Pathway for the Synthesis of Cyclopropanated Fatty Acids in Leaf Tissue Oleic acid on the PC fraction is also the starting point for alternative metabolic pathways, and therefore an alternative metabolic pathway which uses oleic acid as a substrate was investigated as a system to compare different VSP activities in transient leaf assays. Dihydrosterculic acid (DHS) was chosen as the desired product from oleic acid. DHS is a cyclopropanated fatty acid that is produced by cyclopropane fatty acid synthetases (CPFAS) using 18:1-PC as a substrate (FIG. 5). Two different CPFAS genes were compared (FIG. 6) for their activity in leaf assays to produce DHS, namely the *Escherichia coli* CPFAS (EcCPFAS) (SEQ ID NO: 24) and the C-terminal domain of the cotton CPFAS (SEQ ID NO: 21), hereinafter termed GhCPFAS*, using leaf assays in combination with genes encoding V2, hpNbFAD2, DGAT1 and Oleosin.
Construction of Genes to Over-Express EcCPFAS and GhCPFAS* for Transient Expression in Leaves and Seeds A DNA sequence encoding an *Escherichia coli* CPFAS enzyme was chemically synthesised, based on Accession No. AE000261.1 from nucleotide 6129 for a length of 1143 bp (SEQ ID NO: 26). The encoded protein had the same amino acid sequence as the *E. coli* protein, but the nucleotide sequence was codon optimised with a codon bias more suited to eukaryotic expression. The EcCPFAS-encoding fragment was cloned into the EcoRI site of pCW391, generating pCW392, a binary T-DNA construct useful for leaf assays (35S-EcCPFAS).
GhCPFAS*

The first plant CPFAS gene to be isolated and characterised in heterologous expression systems, namely SfCPFAS from *Sterculia foetida*, was found to possess a C-terminal portion of the enzyme with excellent homology to known bacterial CPFAS enzymes and an N-terminal region with motifs with homology to FAD-binding oxidases (Bao et al., 2002). A study has found that SfCPFAS is unusual and different to other plant fatty acid modifying enzymes by acting upon the 18:1 esterified to the sn1 position of phosphatidylcholine (PC) (Bao et al., 2003).

The cotton CPFAS-1 gene shows some homology to the SfCPFAS gene and the expression of full-length GhCPFAS-1 in tobacco BY2 cell cultures likewise resulted in about 1% DHS (Yu et al., 2011). The expression of full-length GhCPFAS-1 in seeds of fad2 fae1 mutant backgrounds of *Arabidopsis*, having elevated levels of oleic acid in seeds, also generated about 1% DHS (Yu et al., 2011). A comparison of the full-length GhCPFAS to produce DHS and a protein truncated by the first 409 amino acids, thus removing the FAD-binding oxidase domain, found that removal of the first 409 amino acids reduced DHS production in yeast by about 70% (Yu et al., 2011). Overall, these results indicated that plant CPFAS enzymes were capable of producing a low level of DHS in transgenic expression systems but that the first 409 amino acids were required for maximal activity. However, as described below the present inventors were surprised to find that in plant cells the truncated enzymes had enhanced CPFAS activity.

A DNA fragment encoding the C-terminal 469 amino acids of the full-length GhCPFAS-1 enzyme, starting at nucleotide position 1248 relative to the sequence in Accession No. AY574036 and using an internal in-frame ATG as the new start codon, was generated in RT-PCR reactions using total RNA isolated from cotton, to generate a nucleotide sequence encoding (SEQ ID NO: 23) the modified protein GhCPFAS* (SEQ ID NO: 21). The predicted length of the protein was 469 amino acids and therefore including only the region with homology to the bacterial CPFAS gene, without the N-terminal region having homology to FAD-binding oxidases. The PCR primers used to amplify this region of GhCPFAS-1 included SpeI flanking sites (underlined), and were Forward primer: 5'-TT<u>ACTAGT</u>ATGGATGCTGCACATGGTATCT-3' (SEQ ID NO: 19) and Reverse primer: 5'-TT<u>ACTAGT</u>TCAATCATCCATGAAGGAATATGCAGAA-3' (SEQ ID NO: 20). The amplicon was inserted into the SpeI site of 35S-pORE4 to generate pCW618 (35S-GhCPFAS*).

The construct was introduced into *Agrobacterium* and used to infiltrate *N. benthamiana* leaves in transient assays as before, in various combinations with other genes. Analyses of the total lipid content of the infiltrated zones of these leaves indicated that GhCPFAS* efficiently produced DHS in leaves (FIG. 6). The level of DHS produced in the presence of GhCPFAS* was approximately 7% of the total fatty acids in leaf lipids, with an overall pathway conversion efficiency of 47% for conversion of oleic acid to DHS. In comparison, EcCPFAS produced less than 1% DHS in total fatty acids in leaf lipids with a conversion efficiency of 4%. GhCPFAS* was therefore used throughout the remainder of this study.

In a further experiment, the production of DHS by GhCPFAS* was used to directly compare the efficiency of p19 or V2 to aid the simultaneous over-expression of the GhCPFAS* transgene and silencing of the NbFAD2 gene, that is, where silencing of an endogenous gene was required to maximise flux into a novel biosynthetic pathway. Various combinations of GhCPFAS*, DGAT1, Oleosin, V2, p19, and hpNbFAD2 were infiltrated into *N. benthamiana* leaves and the production of DHS determined (FIG. 7). In the absence of hpNbFAD2, a slightly greater level of DHS production was observed in the presence of p19 compared to V2. However, in the presence of the hairpin hpNbFAD2, greater levels of DHS were observed with the use of V2. V2 allowed the greatest levels of substrate (18:1) to be produced and also the greatest levels of DHS production. Overall the use of V2 in the combined overexpression and silencing scenario generated approximately 30% more DHS in the leaf assays compared to the use of p19.

A critical step in TAG synthesis pathways involves the removal of the acyl group from the PC head group into the CoA pool. Once acyl groups enter the CoA pool, they become available for the TAG synthesis pathway termed the 'Kennedy' pathway that includes the last committed step of TAG formation catalysed by the DGAT enzyme. The movement of DHS, produced on the PC fraction of leaves, into leaf TAGs was tested by combining GhCPFAS* with DGAT1, Oleosin and hpNbFAD2 (FIG. 10). DHS produced by GhCPFAS*, DGAT1 and Oleosin was found in leaf TAGs at approximately 7% of the total fatty acid content in TAG, with a conversion efficiency of oleic acid to DHS of 55%. The inclusion of hpNbFAD2 boosted the percentage of DHS in leaf TAG from 7% to 15%, while the conversion efficiency remained unchanged at 55%. These results indicated that the combination of V2 and hpNbFAD2 doubled the flux of DHS into the metabolic pathway, using in addition CPFAS*+AtDGAT1+Oleosin, to produce plant oils having higher concentrations of cyclopropanated fatty acids.

To demonstrate whether the DHS was exchanged readily between the PC and CoA pools, a further experiment was performed which added AtFAE1 to the combination of enzymes. The inventors reasoned that the fatty acid DHS, containing a mid-chain propane ring, was likely to form a structure similar to and intermediate between that of a saturated and a monounsaturated C18 fatty acid and that if DHS was transferred from the PC fraction into the CoA pool, it would be a suitable substrate for AtFAE1 to produce elongated DHS (eDHS). To examine if DHS, produced on PC, was transferred into the CoA pool of leaves, the chimeric 35S:AtFAE1 gene was included in combination with genes encoding V2, GhCPFAS* and hpNbFAD2, each under the control of the 35S promoter. The results of the fatty acid analysis are shown in FIG. 11. Total lipids analysed 5 dpi were enriched for DHS and a new metabolite. The new metabolite was confirmed as eDHS, an elongated product of DHS with an additional 2 carbon atoms, by using standard GC/MS techniques (FIG. 12). The conversion efficiency of DHS to eDHS averaged 15% across 6 samples compared to the conversion of 18:1 to 20:1 which averaged 28%. Collectively, these experiments provided evidence that DHS produced on PC was moved efficiently into the CoA pool and accumulated into leaf oils via expression of a combination of endogenous genes and transgenic genes.

Example 7

Transgenic Plant Studies

EcCPFAS in *Arabidopsis* Seeds

The EcCPFAS fragment (Example 6) was cloned into the EcoRI site of pCW442 generating pCW393 (FP1-EcCPFAS) a seed-specific expression vector using the truncated FP1 promoter to drive expression of EcCPFAS. This promoter is useful for expression of transgenes in oilseeds (Ellerstrom et al., 1996). This vector was transformed into *Agrobacterium tumefaciens* strain AGL1, and used to transform *Arabidopsis* plants of the fad2/fae1 double mutant background via the floral dip method. Transgenic seeds were selected on media containing kanamycin (40 mg/L) and T2 seed of these plants analysed for DHS content as described in Example 1.

Seven independent transformed lines of *Arabidopsis* were analysed and the DHS content ranged from trace levels through to 1% DHS, consistent with the studies described above.

GhCPFAS in Seeds of *Arabidopsis* and Safflower

A plant binary expression vector was designed for the expression of transgenes using a promoter derived from the promoter of the AtOlesoin1 gene (TAR website gene annotation At4g25140). The promoter was modified in that 6 basepairs within the 1192 bp sequence were omitted to delete common restriction enzyme sites. The AtOleosin promoter has been used for the strong seed-specific expression of transgenes in safflower and *Brassica* species (Nykiforuk et al., 2011; Van Rooijen and Moloney, 1995). This promoter is thought to be bi-directional, directing not only strong seed-specific expression of transgenes placed at the 3' end of the promoter, but also generating transcripts in the opposite direction from the 5' end of the promoter in a range of tissues. The *Arabidopsis* oleosin promoter shares features of the *Brassica napus* promoter, characterised to have a bi-functional nature (Sadanandom et al., 1996). The promoter was chemically synthesised and subcloned into pGEMT-Easy and an EcoRI fragment of this vector was blunted via the Klenow enzyme fill-in reaction and ligated into the Klenow-blunted HindIII site of pCW265 (Belide et al., 2011), generating pCW600 (AtOleosinP::empty). A SpeI-flanked fragment of pCW618 encompassing the GhCPFAS* coding region was ligated into pCW600, generating pCW619 (AtOloesin:GhCPFAS*).

This pCW619 vector was introduced into *Agrobacterium tumefaciens* strain AGL1 and used to transform *Arabidopsis* of either the fad2 or fad2fae1 mutant genotypes via the floral dip method. The same construct was also used to transform safflower of the variety S317 (high oleic background) via a method using grafting (Belide et al., 2011). 15 independent transformed lines of the fad2 mutant of *Arabidopsis* transformed with pCW619 were obtained and T2 seeds of these plants are maturing. 20 independent transformed lines of safflower S317 transformed with pCW619 were generated and seeds of these plants are maturing. DHS contents in seeds are analysed and are elevated.

Discussion

These experiments showed that the silencing suppressor protein V2 was advantageous in allowing efficient over-expression of one or more genes together with the silencing of genes, in the same cell. Although p19 allowed excellent over-expression of transgenes and was more effective than V2 as a silencing suppressor, p19 also partially blocked hairpin-based silencing of endogenous genes. It is postulated herein that V2 and its functional homologs block the co-suppression pathway which utilises RNA dependent RNA polymerase and SGS3 and thereby maximises expression of a desired gene, but has little effect on the hairpin-RNA or microRNA silencing pathways and thereby allows concomitant gene silencing. The use of V2 also allowed the efficient expression of numerous additional genes to the cells to form a new metabolic pathway, using either individual (separate) vectors or genes combined on single constructs, and thereby entire transgenic pathways could be assembled and tested within a few days in the transient assays. The inventors used the V2-based leaf assays to determine that GhCPFAS* was much better than EcCPFAS in producing DHS. Finally, the optimised leaf assays demonstrated that the unusual fatty acid DHS, produced on PC, was efficiently unloaded into the CoA pool and accumulated in leaf oil. The accumulation of 15% DHS in leaf oils reported here with GhCPFAS* exceeds levels reported with any CPFAS expressed in any plant cell reported in previous studies. Such efficient movements of DHS between lipid pools in leaf cells indicated that leaves might be an ideal location for the production of DHS rather than or alternative to oilseeds.

Beyond oleochemical engineering, we envision that silencing suppressors such as V2 and its homologs will be useful for a range of basic and applied areas of research. Transient leaf assays are currently being developed for the rapid production of personalised antibodies (Levy et al., 2008), however the plant glycosylation and silylation patterns need to be 'humanised' for full efficacy, which requires silencing of several genes in the plant cells. The use of transient leaf expression systems as described above may provide rapid production of antibodies more suitable for human therapies, or allow gene-replacement surveys to be performed.

Example 8

Combining Silencing Suppressors and MicroRNAs

Effect of V2 or p19 on the Activity of an Artificial miRNA in Stably-Transformed Plants Artificial miRNA (amiRNA) constructs may be processed by eukaryotic silencing pathways including in plants to generate a 21 nt long double stranded RNA with 2 nt 3' overhangs, from which a single RNA strand is loaded into Argonaut proteins to guide targeted silencing of a gene of interest whilst the second strand (passenger strand) is degraded (Schwab et al., 2006). The highly specific sRNA created in amiRNA approaches can be contrasted to hairpin-based silencing designs that generate a large population of siRNA, ranging in size from 20-24 nt that span the length of the hairpin (for example, see FIG. 8). p19 was tested to determine if it would block the activity of artificial miRNAs or at least significantly reduce it, whereas V2 was tested to determine if it would allow silencing when combined with artificial miRNAs.

The influence of V2 and p19 on an example of amiRNA activity was tested in two ways, namely amiRNA silencing of a gene encoding a component of chlorophyll biogenesis (AtPDS) and amiRNA targeting of a gene encoding an enzyme in seed oil biosynthesis (AtFAD2). Silencing of the gene encoding Phytoene Desaturase (PDS) using RNAi generated a bleached leaf phenotype (Helliwell et al., 2002). A pri-amiRNA sequence of 915 bp length targeting AtPDS was chemically synthesised using the mi159b as a template pri-amiRNA (Millar and Gubler, 2005) (SEQ ID NO: 52) and cloned into a 35S expression vector, generating pCW159 (35S-pri-amiRNA-PDS). This 35S-pri-amiRNA-PDS-ocs3' fragment was removed by enzymatic digestion and ligated into the binary vectors expressing 35S-p19 and 35S-V2, generating expression constructs for pCW160 (35S-19+35S-pri-amiRNA-PDS) and pCW161 (35S-V2-ocs+35S-pri-amiRNA-PDS), respectively. These constructs, pCW159, pCW160 and pCW161 were introduced into Agrobacterium and used to stably transform Arabidopsis thaliana of the Col-0 ecotype. Seeds of dipped plants were selected on kanamycin selection media and the numbers of bleached and non-bleached transformed seedlings were counted.

Seedlings transformed with the control 35S-pri-amiRNA-PDS, thereby having only the amiRNA silencing construct in the absence of silencing suppressor, were almost all bleached and survived in tissue culture for only about 3 weeks. Seedlings transformed with 35S-V2+35S-pri-amiRNA-PDS also showed only the bleached phenotype and were indistinguishable from seedling transformed with 35S-pri-amiRNA-PDS. In contrast, seedlings transformed with the 35S-p19+35S-pri-amiRNA-PDS remained green and viable. These results indicate that V2 did not interfere with the biogenesis of amiRNA in a seedling context and allowed the miRNA construct to silence the endogenous gene. In contrast, p19 blocked the action of the miRNA, amiRNA-PDS, presumably by binding the 21 nt dsRNA duplexes generated during the processing of the amiRNA.

As described in the earlier Examples, FAD2 desaturates 18:1-PC to 18:2-PC, and ablation of this gene via a hairpin RNA resulted in elevated levels of 18:1. A pri-amiRNA having a length 913 bp, using the same miRNA195b vector template sequence as for the PDS miRNA construct, was designed to target the AtFAD2 gene (SEQ ID NO: 53) and inserted into a seed specific expression vector, FP1-pORE4, generating pJP1106. This vector was introduced into Agrobacterium and used to transform Arabidopsis of the Col-0 ecotype—this ecotype had an active FAD2 gene and consequently low levels of 18:1 in seed oils. Stably transformed plants of this ecotype were isolated and analysed for oleic acid content in seed oil. One line, HX13, was selected as having greatly increased levels of 18:1 in seeds oils, and this event was made homozygous via self-fertilisation of plants into the T4 generation. Homozygous HX13 plants were then super-transformed with Agrobacterium containing binary vectors expressing either FP1-p19 or FP1-V2 and T1 seeds of these plants (FP1-amiRNA-AtFAD2+FP1-V2) or (Fp1-amiRNA-AtFAD2+FP1-p19) selected and grown into T2 seed before analysis of the oil profile.

HX13 plants expressing Fp1-amiRNA-AtFAD2 exhibited an oleic acid content of 65% as a percentage of the total fatty acids in the seedoil. HX13 plants co-expressing FP1-V2 in addition to the amiRNA construct were indistinguishable to those containing the amiRNA construct alone, indicating that V2 did not interfere with amiRNA function in seeds and allowed the miRNA silencing construct to silence as in the absence of the silencing suppressor. In contrast, HX13 plants co-expressing the FP1-p19 construct exhibited markedly reduced 18:1 levels in seedoil, dropping to levels similar to those in seeds of the untransformed Col-0 ecotype. These results indicated that p19 suppressed amiRNA-based silencing of an endogenous gene in seeds.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from U.S. 61/580,574 filed 27 Dec. 2011, the entire contents of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Abdullah et al. (1986) Biotech. 4:1087.
Al-Mariri et al. (2002) Infect. Immun. 70:1915-1923.

Almeida and Allshire (2005) TRENDS Cell Biol. 15: 251-258.
Alvarez et al. (2000) Theor. Appl. Genet. 100:319-327.
Bakker et al. (2006) Proc. Natl. Acad. Sci. USA 103:7577-7582.
Bao et al. (2002) Proc. Natl. Acad. Sci. USA 99:7172-7177.
Bao et al. (2003) Journal of Biological Chemistry 278: 12846-12853.
Baumlein et al. (1991) Mol. Gen. Genet. 225:459-467.
Baumlein et al. (1992) Plant J. 2:233-239.
Beclin et al. (2002) Current Biology 12:684-688.
Belide et al. (2011) Plant Methods 7:12.
Bligh and Dyer (1959). Canadian Journal of Biochemistry and Physiology 37:911-917.
Bouvier-Nave et al. (2000). European Journal of Biochemistry 267: 85-96.
Broothaerts et al. (2005) Nature 433:629-633.
Brosnan et al. (2007) Proc. Natl. Acad. Sci. USA 104:14741-14746.
Broun et al. (1998) Plant J. 13:201-210.
Cadwell and Joyce (1992) PCR Methods Appl. 2:28-33.
Cheng et al. (1996) Plant Cell Rep. 15:653-657.
Chikwamba et al. (2003) Proc. Natl. Acad. Sci. U.S.A. 100:11127-11132.
Chung et al. (2006) BMC Genomics 7:120.
Clough and Bent (1998) Plant J. 16:735-743.
Coco et al. (2001) Nature Biotechnology 19:354-359.
Coco et al. (2002) Nature Biotechnology 20:1246-1250.
Courvalin et al. (1995) Life Sci. 318:1209-1212.
Crameri et al. (1998) Nature 391:288-291.
Darji et al. (1997) Cell 91:765-775.
Dietrich et al. (1998) Nature Biotech. 18:181-185.
Eggert et al. (2005) Chembiochem 6:1062-1067.
Ellerstrom et al. (1996) Plant Mol. Biol. 32:1019-1027.
Elmayan et al. (1998) Plant Cell 10: 1747-1757.
Fennelly et al. (1999) J. Immunol. 162:1603-1610.
Fujimura et al. (1985) Plant Tissue Culture Lett. 2:74.
Fukunaga and Doudna (2009) EMBO Journal 28:545-555.
Glevin et al. (2003) Microbiol. Mol. Biol. Rev. 67:16-37.
Glick et al. (2008) Proc. Natl. Acad. Sci. USA 105:157-161.
Grant et al. (1995) Plant Cell Rep. 15:254-258.
Grillot-Courvalin et al. (1998) Nature Biotech. 16:862-866.
Grillot-Courvalin (1999) Curr. Opin. Biotech. 10:477-481.
Harayama (1998) Trends Biotechnol. 16:76-82.
Helliwell et al. (2002) Functional Plant Biology 29:1217-1225.
Helliwell et al. (2006) Plant Journal 46:183-192.
Hense et al. (2001) Cell Microbiol. 3:599-609.
Hillman et al. (1989) Virology 169:42-50.
Hinchee et al. (1988) Biotechnology 6:915-922.
Horvath et al. (2000) Proc. Natl. Acad. Sci. U.S.A. 97:1914-1919.
James et al. (1995) Plant Cell 7: 309-319.
Jézéquel et al. (2008) Biotechniques 45:523-532.
Johansen and Carrington (2001) Plant Physiology 126:930-938.
Katavic et al. (1995) Plant Physiology 108: 399-409.
Koziel et al. (1996) Plant Mol. Biol. 32:393-405.
Kunik et al. (2001) Proc. Natl. Acad. Sci. U.S.A. 98:1871-1876.
Lacroix et al. (2008) Proc. Natl. Acad. Sci. U.S.A. 105: 15429-15434.
Levy et al. (2008) Proc. Natl. Acad. Sci. USA 105:10131-10136.
Millar and Waterhouse (2005) Funct. Integr. Genomics 5:129-135.
Millar et al. (1998) Plant Cell 10:1889-1902.
Millar and Gubler (2005) Plant Cell 17(3):705-721.
Mourrain et al. (2000) Cell 101:533-542.
Needleman and Wunsch (1970) J. Mol. Biol. 48:443-453.
Ness et al. (2002) Nature Biotechnology 20:1251-1255.
Niedz et al. (1995) Plant Cell Reports 14:403.
Nykiforuk et al. (2011) Plant Biotechnology Journal 9:250-263.
Ohlrogge and Browse (1995) Plant Cell 7:957-970.
Ostermeier et al. (1999) Nature Biotechnology 17:1205-1209.
Ow et al. (1986) Science 234:856-859.
Pasquinelli et al (2005) Curr. Opin. Genet. Develop. 15:200-205.
Perrin et al. (2000) Mol. Breed. 6:345-352.
Peterson et al. (1997). Plant Molecular Biology Reporter 15:148-153.
Petrie et al. (2010) Plant Methods 6:8.
Potenza et al. (2004) In Vitro Cell Dev. Biol. Plant 40:1-22.
Powell et al. (1996) Vaccines 183, Abstract.
Prasher et al. (1985) Biochem. Biophys. Res. Commun. 127:31-36.
Sadanandom et al. (1996) Plant Journal 10:235-242.
Schaffner et al. (1980) Proc. Natl. Acad. Sci. U.S.A. 77:2163-2167.
Schwab et al. (2006) Plant Cell 18: 1121-1133.
Scott et al. (2010) Plant Biotechnology Journal 8:912-927.
Shiau et al. (2001) Vaccine 19:3947-3956.
Sieber et al. (2001) Nature Biotechnology 19:456-460.
Sizemore et al. (1995) Science 270:299-302.
Smith et al. (2000) Nature 407:319-320.
Stalker et al. (1988) Science 242:419-423.
Stemmer (1994a) Proc. Natl. Acad. Sci. USA 91:10747-10751.
Stemmer (1994b) Nature 370:389-391.
Taylor (1997) The Plant Cell 9:1245-1249.
Thillet et al. (1988) J. Biol. Chem. 263:12500-12508.
Toriyama et al. (1986) Theor. Appl. Genet. 205:34.
Tzen et al. (1992) J. Biol. Chem. 267: 15626-15634.
Tzfira and Citovsky (2006) Curr. Opin. Biotech. 17:147-154.
Van Rooijen and Moloney (1995) Bio-Technology 13:72-77.
Voinnet et al. (2003) Plant Journal 33:949-956.
Volkov et al. (1999) Nucleic acids research 27:e18.
Waterhouse et al (1998) Proc. Natl. Acad. Sci. USA 95:13959-13964.
Weiss et al. (2003) Int. J. Med. Microbiol. 293:95:106.
Wood et al. (2009) Plant Biotechnology Journal 7:914-924.
Yang et al. (2003) Planta 216:597-603.
Ye et al. (2003) Nature 426:874-878.
Yu et al. (2011) BMC Plant Biology 11:97.
Zhao et al. (1998) Nature Biotechnology 16:258-261.

The invention claimed is:

1. A plant cell comprising,
   i) a polynucleotide of interest which encodes a target RNA,
   ii) a first exogenous polynucleotide encoding a double stranded RNA (dsRNA) molecule which comprises a stem-loop and a first nucleotide sequence which is complementary to a region of the target RNA encoded by the polynucleotide of interest,
   iii) a second exogenous polynucleotide encoding a silencing suppressor polypeptide,
   iv) a third exogenous polynucleotide, different to the first and second exogenous polynucleotides and the polynucleotide of interest, which encodes an RNA of interest,
   v) a reduced level of the target RNA encoded by the polynucleotide of interest and/or the amount of a protein encoded by the target RNA when compared to a corresponding cell lacking the first exogenous polynucleotide, and
   vi) an increased level of the RNA of interest and/or the amount of protein encoded by the RNA of interest when compared to a corresponding cell having the third exogenous polynucleotide and lacking the second exogenous polynucleotide,
   wherein each exogenous polynucleotide is operably linked to one or more promoters that are capable of directing expression of the polynucleotide in the cell, wherein the first and second exogenous polynucleotides form part of one DNA construct, and wherein the silencing suppressor comprises amino acids having the sequence set forth in SEQ ID NO: 1, or a sequence which is at least 95% identical to the sequence set forth in SEQ ID NO: 1.

2. The plant cell of claim 1, wherein the polynucleotide of interest is an endogenous gene of the cell or a gene of a pathogen of the cell.

3. The plant cell of claim 1, wherein the first and second exogenous polynucleotides form part of one DNA construct which is integrated into the genome of the cell.

4. The plant cell of claim 1, wherein the first, second and third exogenous polynucleotides form part of one DNA construct which is integrated into the genome of the cell.

5. The plant cell of claim 1, wherein at least the second exogenous polynucleotide is integrated into the genome of the cell.

6. The plant cell of claim 1, wherein the cell comprises at least a 25% reduction in the level of the target RNA encoded by the polynucleotide of interest and/or amount of protein encoded by the target RNA when compared to a corresponding cell lacking the first exogenous polynucleotide.

7. The plant cell of claim 1, wherein the dsRNA molecule, or a processed RNA product thereof, comprises at least 19 consecutive nucleotides which is at least 95% identical to the complement of a region of the target RNA, and wherein the region of the target RNA is i) within a 5' untranslated region of the target RNA, ii) within a 5' half of the target RNA, iii) within a protein-encoding open-reading frame of the target RNA, iv) within a 3' half of the target RNA, or v) within a 3' untranslated region of the target RNA.

8. The plant cell of claim 1, wherein the dsRNA molecule is a microRNA (miRNA) precursor and/or wherein the processed RNA product thereof is a miRNA.

9. The plant cell of claim 1, wherein the third exogenous polynucleotide encodes a protein or microRNA precursor.

10. The plant cell of claim 1, wherein the cell further comprises at least one, at least two, at least three, at least four or at least five additional, different exogenous polynucleotides each encoding different RNAs of interest.

11. The plant cell of claim 10, where the additional, different exogenous polynucleotides form part of one DNA construct.

12. The plant cell of claim 1, wherein the cell further comprises at least one, at least two, at least three, at least four or at least five additional, different exogenous polynucleotides each independently encoding different dsRNA molecules which comprise different nucleotide sequences which are complementary to a region of different target RNAs encoded by different polynucleotides of interest, and/or different nucleotide sequences which are complementary to different regions of the same target RNA.

13. The plant cell of claim 1, wherein the first exogenous polynucleotide encodes more than one miRNA which independently comprise different nucleotide sequences which are complementary to a region of different target RNAs encoded by different polynucleotides of interest, and/or different nucleotide sequences which are complementary to different regions of the same target RNA.

14. The plant cell of claim 1, wherein the exogenous polynucleotides are operably linked to different promoters.

15. The plant cell of claim 1, wherein the second exogenous polynucleotide was introduced into the cell on a vector other than a viral vector.

16. The plant cell of claim 1, wherein the dsRNA molecule is a hairpin RNA.

17. The plant cell of claim 1, wherein the silencing suppressor comprises amino acids having a sequence which is at least 96% identical to the sequence set forth in SEQ ID NO:1.

18. The plant cell of claim 1, wherein the silencing suppressor comprises amino acids having a sequence which is at least 97% identical to the sequence set forth in SEQ ID NO:1.

19. The plant cell of claim 1, wherein the silencing suppressor comprises amino acids having the sequence set forth in SEQ ID NO:1.

20. The plant cell of claim 12, wherein the additional polynucleotides form part of the same DNA construct.

* * * * *